US012559565B2

(12) United States Patent  
Chen et al.

(10) Patent No.: US 12,559,565 B2  
(45) Date of Patent: Feb. 24, 2026

(54) ANTIBODIES BINDING CTLA4 AND USES THEREOF

(71) Applicant: BIOSION INC., Jiangsu (CN)

(72) Inventors: Mingjiu Chen, Nanjing (CN); Shukai Xia, Nanjing (CN)

(73) Assignee: BIOSION INC., Nanjing (CN)

( * ) Notice: Subject to any disclaimer, the term of this patent is extended or adjusted under 35 U.S.C. 154(b) by 711 days.

(21) Appl. No.: 17/907,442

(22) PCT Filed: Apr. 12, 2021

(86) PCT No.: PCT/CN2021/086484  
§ 371 (c)(1),  
(2) Date: Sep. 27, 2022

(87) PCT Pub. No.: WO2021/208838  
PCT Pub. Date: Oct. 21, 2021

(65) Prior Publication Data  
US 2023/0212304 A1 Jul. 6, 2023

Related U.S. Application Data

(60) Provisional application No. 63/008,931, filed on Apr. 13, 2020.

(51) Int. Cl.  
*C07K 16/28* (2006.01)  
*C12N 15/63* (2006.01)

(52) U.S. Cl.  
CPC .......... *C07K 16/2896* (2013.01); *C12N 15/63* (2013.01); *C07K 2317/24* (2013.01); *C07K 2317/33* (2013.01); *C07K 2317/565* (2013.01)

(58) Field of Classification Search  
None  
See application file for complete search history.

(56) References Cited

U.S. PATENT DOCUMENTS

| | | | |
|---|---|---|---|
| 2017/0216433 A1 | 8/2017 | Li et al. | |
| 2017/0240644 A1* | 8/2017 | Zhou .................... G01N 33/577 |
| 2019/0127468 A1 | 5/2019 | Liu et al. | |
| 2019/0177414 A1 | 6/2019 | Li et al. | |

FOREIGN PATENT DOCUMENTS

| | | | |
|---|---|---|---|
| CN | 105296433 A | 2/2016 | |
| CN | 108430499 A | 8/2018 | |
| CN | 109963588 A | 7/2019 | |
| WO | 2018183408 A1 | 10/2018 | |
| WO | WO-2019056281 A1 * | 3/2019 | ......... C07K 16/2818 |

OTHER PUBLICATIONS

Almagro et al., Frontiers in Immunology, 2018, 8: 1751 (Year: 2018).*  
Sela-Culang et al., Frontiers in Immunology, 2013, 4:302 (Year: 2013).*  
Ni et al., The Protein Journal, 2024, 43: 683-696 (Year: 2025).*  
Sahin et al., Clinical Review, 2020, 16:319-326 (Year: 2020).*  
Randi B. Gombos, et al., Toxicological and pharmacological assessment of AGEN1884, a novel human IgGI anti-CTLA-4 antibody, PLOS ONE, (Apr. 4, 2018) vol. 13. No. 4.  
International Search Report and Written Opinion dated Jul. 15, 2021 issued in Int'l Appl. No. PCT/CN2021/086484.

\* cited by examiner

*Primary Examiner* — Julie Wu  
(74) *Attorney, Agent, or Firm* — Duane Morris LLP; Thomas J. Kowalski

(57) ABSTRACT  
An isolated monoclonal antibody that specifically binds human CTLA4, or the antigen-binding portion thereof. A nucleic acid molecule encoding the antibody or the antigen-binding portion thereof, an expression vector, a host cell and a method for expressing the antibody or the antigen-binding portion thereof are also provided. The present disclosure further provides an immunoconjugate, a bispecific molecule, a chimeric antigen receptor, an oncolytic virus and a pharmaceutical composition comprising the antibody or the antigen-binding portion thereof, as well as a treatment method using the anti-CTLA4 antibody or the antigen-binding portion thereof.

19 Claims, 11 Drawing Sheets

Specification includes a Sequence Listing.

| | mouse D1H4 | mouse D1A7 | mouse D1B6 |
|---|---|---|---|
| EC50 | 0.1076 | 0.1339 | 0.1159 |

| | mouse C1G4 | mouse D1H3 | mouse D1B8 |
|---|---|---|---|
| EC50 | 0.1335 | 0.2058 | 1.106 |

| mouse D1D5 | mouse D2A4 | mouse C1D1 | mouse D1G6 |
|---|---|---|---|
| 0.1034 | 0.2446 | 0.04791 | 0.09787 |

| | mouse D2A4 | mouse C1D1 | mouse C1G4 |
|---|---|---|---|
| IC50 | 3.85 | 0.3376 | 0.8646 |

| mouse D1B6 | mouse D1D5 | Yervoy |
|---|---|---|
| 0.6176 | 0.6464 | 0.7094 |

| | mouse D1H3 | mouse D1A7 | mouse D1G6 | Yervoy |
|---|---|---|---|---|
| IC50 | 1.858 | 0.4447 | 0.4449 | 1.151 |

| | mouse D1H4 | mouse D1A7 | mouse D1B6 | Yerovy |
|---|---|---|---|---|
| IC50 | ~ 8.845 | 6.808 | ~ 4.6 | 3.476 |

| | mouse C1G4 | mouse D1H3 | mouse D1D5 |
|---|---|---|---|
| IC50 | 10.97 | 9.268 | 4.767 |

| mouse D2A4 | mouse C1D1 | Yervoy |
|---|---|---|
| 7.115 | 6.22 | 6.218 |

| | mouse D2A4 | mouse C1D1 | mouse C1G4 | mouse D1B6 | mouse D1D5 |
|---|---|---|---|---|---|
| EC50 | 38.29 | 35.14 | 35.33 | 36.57 | 37.49 |

| mouse D1H3 | mouse D1H4 | mouse D1G6 | mouse D1B8 | mouse D1A7 | Yervoy |
|---|---|---|---|---|---|
| 37.77 | ~ 40.79 | 41.5 | 43.56 | 45.92 | 23.69 |

|  | chimeric C1G4 | mouse C1G4 | Yervoy |
|---|---|---|---|
| EC50 | 0.8686 | 0.8318 | 0.4233 |

|  | chimeric D1B6 | mouse D1B6 | Yervoy |
|---|---|---|---|
| EC50 | 0.514 | 0.4184 | 0.486 |

|  | chimeric C1D1 | mouse C1D1 | Yervoy |
|---|---|---|---|
| EC50 | 0.5048 | 0.4446 | 0.5223 |

|  | chimeric D1D5 | mouse D1D5 | Yervoy |
|---|---|---|---|
| EC50 | 0.9915 | 0.6321 | 0.6786 |

|  | chimeric D1B8 | mouse D1B8 | Yervoy |
|---|---|---|---|
| EC50 | 2.841 | 5.784 | 0.5734 |

| | mouse C1G4 | chimeric C1G4 | mouse D1B6 |
|---|---|---|---|
| IC50 | 10.58 | 10.23 | 8.093 |

| chimeric D1B6 | mouse C1D1 | chimeric C1D1 | Yervoy |
|---|---|---|---|
| ~ 6.604 | ~ 11.62 | 8.559 | 9.325 |

| | mouse D1D5 | chimeric D1D5 | Yervoy |
|---|---|---|---|
| IC50 | 9.673 | 12.61 | 31.66 |

| | mouse C1D1 | chimeric C1D1 | huC1D1-V8 | Yervoy |
|---|---|---|---|---|
| EC50 | 0.1206 | 0.1561 | 0.7461 | 0.7556 |

| | mouse D1D5 | chimeric D1D5 | huD1D5-V9 | Yervoy |
|---|---|---|---|---|
| EC50 | 0.7785 | 0.5749 | 0.5165 | 0.8918 |

| | mouse C1D1 | chimeric C1D1 | huC1D1-V8 | Yervoy |
|---|---|---|---|---|
| IC50 | 0.7997 | 2.11 | 1.712 | 0.9092 |

| | mouse D1D5 | chimeric D1D5 | huD1D5-V9 | Yervoy |
|---|---|---|---|---|
| IC50 | 5.746 | 0.7852 | 0.6419 | 0.9735 |

| | mouse C1D1 | chimeric C1D1 | huC1D1-V8 | Yervoy |
|---|---|---|---|---|
| IC50 | ~ 9.72 | ~ 9.958 | 5.735 | 6.397 |

| | mouse D1D5 | chimeric D1D5 | huD1D5-V9 | Yervoy |
|---|---|---|---|---|
| IC50 | 5.815 | 5.999 | 5.526 | 6.532 |

| | mouse C1D1 | mouse D1D5 | chimeric C1D1 |
|---|---|---|---|
| EC50 | 0.03002 | 0.04231 | 0.034 |

| chimeric D1D5 | huC1D1-V8 | huD1D5-V9 | Yervoy |
|---|---|---|---|
| 0.08211 | 0.02868 | 0.02734 | 0.02716 |

SEQUENCE LISTING

<160> NUMBER OF SEQ ID NOS: 93

<210> SEQ ID NO 1
<211> LENGTH: 5
<212> TYPE: PRT
<213> ORGANISM: Artificial Sequence
<220> FEATURE:
<223> OTHER INFORMATION: VH CDR1 for mouse, chimeric and humanized C1D1,
      mouse and chimeric C1G4

<400> SEQUENCE: 1

Asp Asn Trp Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: VH CDR2 for mouse, chimeric and humanized C1D1,
      mouse and chimeric C1G4

<400> SEQUENCE: 2

Gln Ile Arg Asn Lys Pro Tyr Asn Tyr Glu Thr Tyr Tyr Ser Asp Ser
1               5                   10                  15

Val Lys Gly

<210> SEQ ID NO 3
<211> LENGTH: 4
<212> TYPE: PRT
<213> ORGANISM: Artificial Sequence
<220> FEATURE:
<223> OTHER INFORMATION: VH CDR3 for mouse, chimeric and humanized C1D1

<400> SEQUENCE: 3

Gly Met Asp Tyr
1

<210> SEQ ID NO 4
<211> LENGTH: 11
<212> TYPE: PRT
<213> ORGANISM: Artificial Sequence
<220> FEATURE:
<223> OTHER INFORMATION: VL CDR1 for mouse, chimeric and humanized C1D1

<400> SEQUENCE: 4

Gly Ala Ser Glu Ile Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR2 for mouse, chimeric and humanized C1D1,
      mouse and chimeric C1G4

<400> SEQUENCE: 5

Gly Ala Thr Asn Leu Ala Asp
1               5

<210> SEQ ID NO 6
<211> LENGTH: 10
<212> TYPE: PRT
<213> ORGANISM: Artificial Sequence
<220> FEATURE:
<223> OTHER INFORMATION: VL CDR3 for mouse, chimeric and humanized C1D1

<400> SEQUENCE: 6

Gln Lys Ile Leu Ser Pro Pro Pro Trp Thr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: VH CDR1 for mouse, chimeric and humanized D1D5

<400> SEQUENCE: 7

Asp Tyr Gly Met Ala
1               5

<210> SEQ ID NO 8
<211> LENGTH: 17
<212> TYPE: PRT
<213> ORGANISM: Artificial Sequence
<220> FEATURE:
<223> OTHER INFORMATION: VH CDR2 for mouse, chimeric and humanized D1D5

<400> SEQUENCE: 8

Phe Ile Ser Asn Leu Ala Tyr Ser Val Tyr Tyr Ala Asp Thr Glu Thr
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: VH CDR3 for mouse, chimeric and humanized D1D5

<400> SEQUENCE: 9

Ser Gly Leu Pro Tyr Ala Met Asp Tyr
1               5

<210> SEQ ID NO 10
<211> LENGTH: 11
<212> TYPE: PRT
<213> ORGANISM: Artificial Sequence

```
<220> FEATURE:
<223> OTHER INFORMATION: VL CDR1 for mouse, chimeric and humanized D1D5

<400> SEQUENCE: 10

Arg Ala Ser Gln Asp Ile Ser Asn Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: VL CDR2 for mouse, chimeric and humanized D1D5

<400> SEQUENCE: 11

Tyr Ile Ser Arg Leu His Ser
1               5

<210> SEQ ID NO 12
<211> LENGTH: 9
<212> TYPE: PRT
<213> ORGANISM: Artificial Sequence
<220> FEATURE:
<223> OTHER INFORMATION: VL CDR3 for mouse, chimeric and humanized D1D5

<400> SEQUENCE: 12

Gln Gln Gly Arg Met Leu Pro Trp Thr
1               5

<210> SEQ ID NO 13
<211> LENGTH: 4
<212> TYPE: PRT
<213> ORGANISM: Artificial Sequence
<220> FEATURE:
<223> OTHER INFORMATION: VH CDR3 for mouse C1G4

<400> SEQUENCE: 13

Gly Phe Thr Tyr
1

<210> SEQ ID NO 14
<211> LENGTH: 11
<212> TYPE: PRT
<213> ORGANISM: Artificial Sequence
<220> FEATURE:
<223> OTHER INFORMATION: VL CDR1 for mouse C1G4

<400> SEQUENCE: 14

Gly Ala Ser Glu Asn Ile Tyr Gly Gly Leu Asn
1               5                   10

<210> SEQ ID NO 15
<211> LENGTH: 9
<212> TYPE: PRT
<213> ORGANISM: Artificial Sequence
<220> FEATURE:
<223> OTHER INFORMATION: VL CDR3 for mouse C1G4

<400> SEQUENCE: 15

Gln Asn Val Leu Asn Thr Pro Tyr Thr
1               5

<210> SEQ ID NO 16
<211> LENGTH: 7
<212> TYPE: PRT
<213> ORGANISM: Artificial Sequence
<220> FEATURE:
```

<223> OTHER INFORMATION: VH CDR1 for mouse D1A7

<400> SEQUENCE: 16

Ser Ser Lys Leu Gly Val Gly
1               5

<210> SEQ ID NO 17
<211> LENGTH: 16
<212> TYPE: PRT
<213> ORGANISM: Artificial Sequence
<220> FEATURE:
<223> OTHER INFORMATION: VH CDR2 for mouse D1A7

<400> SEQUENCE: 17

His Ile Trp Trp Asn Asp Asp Asn Tyr Tyr Val Pro Ser Leu Lys Ser
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: VH CDR3 for mouse D1A7

<400> SEQUENCE: 18

Val Pro Tyr Tyr Thr Thr Gln Pro Trp Phe Ala Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: VL CDR1 for mouse D1A7

<400> SEQUENCE: 19

Arg Ala Ser Gly Asn Ile His Asn Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VL CDR2 for mouse D1A7

<400> SEQUENCE: 20

Asn Thr Glu Thr Leu Ala Asp
1               5

<210> SEQ ID NO 21
<211> LENGTH: 9
<212> TYPE: PRT
<213> ORGANISM: Artificial Sequence
<220> FEATURE:
<223> OTHER INFORMATION: VL CDR3 for mouse D1A7

<400> SEQUENCE: 21

Gln His Leu Trp Ser Thr Pro Trp Thr
1               5

<210> SEQ ID NO 22
<211> LENGTH: 5
<212> TYPE: PRT
<213> ORGANISM: Artificial Sequence
<220> FEATURE:
<223> OTHER INFORMATION: VH CDR1 for mouse D1B6, and mouse D1G6

-continued

```
<400> SEQUENCE: 22

Thr Tyr Val Leu Asn
1               5

<210> SEQ ID NO 23
<211> LENGTH: 17
<212> TYPE: PRT
<213> ORGANISM: Artificial Sequence
<220> FEATURE:
<223> OTHER INFORMATION: VH CDR2 for mouse D1B6

<400> SEQUENCE: 23

Tyr Phe Asn Pro Tyr Asn Asp Gly Ile Lys Tyr Asn Glu Lys Phe Lys
1               5                   10                  15

Gly

<210> SEQ ID NO 24
<211> LENGTH: 10
<212> TYPE: PRT
<213> ORGANISM: Artificial Sequence
<220> FEATURE:
<223> OTHER INFORMATION: VH CDR3 for mouse D1B6 and mouse D1G6

<400> SEQUENCE: 24

Phe Glu Gly Gly Gly Tyr Ala Met Asp Tyr
1               5                   10

<210> SEQ ID NO 25
<211> LENGTH: 15
<212> TYPE: PRT
<213> ORGANISM: Artificial Sequence
<220> FEATURE:
<223> OTHER INFORMATION: VL CDR1 for mouse D1B6

<400> SEQUENCE: 25

Arg Ala Ser Gln Ser Val Gly Thr Ser Arg Asn Thr Tyr Ile His
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: VL CDR2 for mouse D1B6 and mouse D1G6

<400> SEQUENCE: 26

Tyr Ala Ser Asp Leu Glu Ser
1               5

<210> SEQ ID NO 27
<211> LENGTH: 9
<212> TYPE: PRT
<213> ORGANISM: Artificial Sequence
<220> FEATURE:
<223> OTHER INFORMATION: VL CDR3 for mouse D1B6 and mouse D1G6

<400> SEQUENCE: 27

Gln His Ser Trp Glu Ile Pro Tyr Thr
1               5

<210> SEQ ID NO 28
<211> LENGTH: 5
<212> TYPE: PRT
<213> ORGANISM: Artificial Sequence
<220> FEATURE:
```

<223> OTHER INFORMATION: VH CDR1 for mouse D1B8

<400> SEQUENCE: 28

Asp Tyr Tyr Ile Asn
1               5

<210> SEQ ID NO 29
<211> LENGTH: 17
<212> TYPE: PRT
<213> ORGANISM: Artificial Sequence
<220> FEATURE:
<223> OTHER INFORMATION: VH CDR2 for mouse D1B8

<400> SEQUENCE: 29

Trp Ile Tyr Pro Gly Asn Asn Asn Thr Arg Tyr Asn Glu Lys Phe Lys
1               5                   10                  15

Gly

<210> SEQ ID NO 30
<211> LENGTH: 5
<212> TYPE: PRT
<213> ORGANISM: Artificial Sequence
<220> FEATURE:
<223> OTHER INFORMATION: VH CDR3 for mouse D1B8

<400> SEQUENCE: 30

Tyr Tyr Phe Asp Tyr
1               5

<210> SEQ ID NO 31
<211> LENGTH: 11
<212> TYPE: PRT
<213> ORGANISM: Artificial Sequence
<220> FEATURE:
<223> OTHER INFORMATION: VL CDR1 for mouse D1B8

<400> SEQUENCE: 31

Arg Ala Ser Gln Glu Ile Thr Gly Tyr Leu Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: VL CDR2 for mouse D1B8

<400> SEQUENCE: 32

Ala Ala Ser Thr Leu Asp Ser
1               5

<210> SEQ ID NO 33
<211> LENGTH: 9
<212> TYPE: PRT
<213> ORGANISM: Artificial Sequence
<220> FEATURE:
<223> OTHER INFORMATION: VL CDR3 for mouse D1B8

<400> SEQUENCE: 33

Leu Gln Tyr Ala Ser Tyr Pro Arg Thr
1               5

<210> SEQ ID NO 34
<211> LENGTH: 17
<212> TYPE: PRT
<213> ORGANISM: Artificial Sequence

```
<220> FEATURE:
<223> OTHER INFORMATION: VH CDR2 for mouse D1G6

<400> SEQUENCE: 34

Tyr Phe Asn Pro Tyr Asn Asp Ala Ile Lys Tyr Asn Glu Lys Phe Lys
1               5                   10                  15

Gly

<210> SEQ ID NO 35
<211> LENGTH: 15
<212> TYPE: PRT
<213> ORGANISM: Artificial Sequence
<220> FEATURE:
<223> OTHER INFORMATION: VL CDR1 for mouse D1G6

<400> SEQUENCE: 35

Arg Ala Ser Gln Ser Val Gly Thr Ser Ser Tyr Ser Tyr Ile His
1               5                   10                  15

<210> SEQ ID NO 36
<211> LENGTH: 5
<212> TYPE: PRT
<213> ORGANISM: Artificial Sequence
<220> FEATURE:
<223> OTHER INFORMATION: VH CDR1 for mouse D1H3

<400> SEQUENCE: 36

Ser Tyr Trp Leu His
1               5

<210> SEQ ID NO 37
<211> LENGTH: 17
<212> TYPE: PRT
<213> ORGANISM: Artificial Sequence
<220> FEATURE:
<223> OTHER INFORMATION: VH CDR2 for mouse D1H3

<400> SEQUENCE: 37

Arg Ile Asp Pro Asn Arg Gly Thr Ile Tyr Tyr Asn Glu Lys Phe Asn
1               5                   10                  15

Asn

<210> SEQ ID NO 38
<211> LENGTH: 10
<212> TYPE: PRT
<213> ORGANISM: Artificial Sequence
<220> FEATURE:
<223> OTHER INFORMATION: VH CDR3 for mouse D1H3

<400> SEQUENCE: 38

Gly Gly Ser Asn Phe Tyr Ala Met Asp Tyr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: VL CDR1 for mouse D1H3

<400> SEQUENCE: 39

Arg Thr Ser Glu Asn Ile Tyr Ser Tyr Leu Ala
1               5                   10

<210> SEQ ID NO 40
```

```
<211> LENGTH: 7
<212> TYPE: PRT
<213> ORGANISM: Artificial Sequence
<220> FEATURE:
<223> OTHER INFORMATION: VL CDR2 for mouse D1H3

<400> SEQUENCE: 40

Asn Ala Lys Thr Leu Ala Glu
1               5

<210> SEQ ID NO 41
<211> LENGTH: 9
<212> TYPE: PRT
<213> ORGANISM: Artificial Sequence
<220> FEATURE:
<223> OTHER INFORMATION: VL CDR3 for mouse D1H3

<400> SEQUENCE: 41

Gln Asn His Asp Gly Ile Pro Phe Thr
1               5

<210> SEQ ID NO 42
<211> LENGTH: 5
<212> TYPE: PRT
<213> ORGANISM: Artificial Sequence
<220> FEATURE:
<223> OTHER INFORMATION: VH CDR1 for mouse D1H4

<400> SEQUENCE: 42

Asp Tyr Tyr Met Asn
1               5

<210> SEQ ID NO 43
<211> LENGTH: 17
<212> TYPE: PRT
<213> ORGANISM: Artificial Sequence
<220> FEATURE:
<223> OTHER INFORMATION: VH CDR2 for mouse D1H4

<400> SEQUENCE: 43

Ala Ile Asn Pro Asp His Gly Gly Ser Ser Tyr Asn Gln Lys Phe Lys
1               5                   10                  15

Gly

<210> SEQ ID NO 44
<211> LENGTH: 10
<212> TYPE: PRT
<213> ORGANISM: Artificial Sequence
<220> FEATURE:
<223> OTHER INFORMATION: VH CDR3 for mouse D1H4

<400> SEQUENCE: 44

Asp Gly Ser Ile His Tyr Val Met Asp Asp
1               5                   10

<210> SEQ ID NO 45
<211> LENGTH: 17
<212> TYPE: PRT
<213> ORGANISM: Artificial Sequence
<220> FEATURE:
<223> OTHER INFORMATION: VL CDR1 for mouse D1H4

<400> SEQUENCE: 45

Lys Ser Ser Gln Ser Leu Leu His Ser Gly Asn Gln Lys Asn Tyr Leu
1               5                   10                  15

Ala
```

```
<210> SEQ ID NO 46
<211> LENGTH: 7
<212> TYPE: PRT
<213> ORGANISM: Artificial Sequence
<220> FEATURE:
<223> OTHER INFORMATION: VL CDR2 for mouse D1H4

<400> SEQUENCE: 46

Gly Ala Ser Thr Arg Glu Ser
1               5

<210> SEQ ID NO 47
<211> LENGTH: 9
<212> TYPE: PRT
<213> ORGANISM: Artificial Sequence
<220> FEATURE:
<223> OTHER INFORMATION: VL CDR3 for mouse D1H4

<400> SEQUENCE: 47

Gln Asn Asp Tyr Gly Tyr Pro Tyr Thr
1               5

<210> SEQ ID NO 48
<211> LENGTH: 5
<212> TYPE: PRT
<213> ORGANISM: Artificial Sequence
<220> FEATURE:
<223> OTHER INFORMATION: VH CDR1 for mouse D2A4

<400> SEQUENCE: 48

Ser Tyr Trp Val His
1               5

<210> SEQ ID NO 49
<211> LENGTH: 17
<212> TYPE: PRT
<213> ORGANISM: Artificial Sequence
<220> FEATURE:
<223> OTHER INFORMATION: VH CDR2 for mouse D2A4

<400> SEQUENCE: 49

Arg Ile Asp Pro Asn Arg Gly Gly Thr Tyr Tyr Asn Glu Asn Phe Lys
1               5                   10                  15

Thr

<210> SEQ ID NO 50
<211> LENGTH: 10
<212> TYPE: PRT
<213> ORGANISM: Artificial Sequence
<220> FEATURE:
<223> OTHER INFORMATION: VH CDR3 for mouse D2A4

<400> SEQUENCE: 50

Gly Gly Leu Asn Tyr Tyr Ala Leu Asp Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: VL CDR1 for mouse D2A4

<400> SEQUENCE: 51

Arg Ala Ser Glu Asn Ile Tyr Ser Tyr Leu Ala
```

```
1               5                10

<210> SEQ ID NO 52
<211> LENGTH: 7
<212> TYPE: PRT
<213> ORGANISM: Artificial Sequence
<220> FEATURE:
<223> OTHER INFORMATION: VL CDR2 for mouse D2A4

<400> SEQUENCE: 52

Asn Ala Asn Thr Leu Thr Glu
1               5

<210> SEQ ID NO 53
<211> LENGTH: 9
<212> TYPE: PRT
<213> ORGANISM: Artificial Sequence
<220> FEATURE:
<223> OTHER INFORMATION: VL CDR3 for mouse D2A4

<400> SEQUENCE: 53

Gln His His Tyr Gly Ile Pro Phe Thr
1               5

<210> SEQ ID NO 54
<211> LENGTH: 115
<212> TYPE: PRT
<213> ORGANISM: Artificial Sequence
<220> FEATURE:
<223> OTHER INFORMATION: VH for mouse and chimeric C1D1

<400> SEQUENCE: 54

Glu Val Lys Leu Asp Glu Thr Gly Gly Gly Leu Val Gln Pro Gly Arg
1               5                10               15

Pro Leu Lys Leu Ser Cys Val Ala Ser Gly Phe Thr Phe Ser Asp Asn
            20               25               30

Trp Met Asn Trp Val Arg Gln Ser Pro Glu Lys Gly Leu Glu Trp Val
        35               40               45

Ala Gln Ile Arg Asn Lys Pro Tyr Asn Tyr Glu Thr Tyr Tyr Ser Asp
    50               55               60

Ser Val Lys Gly Arg Phe Thr Ile Ser Arg Asp Asp Ser Lys Ser Ser
65               70               75               80

Val Tyr Leu Gln Met Asn Asn Leu Arg Val Glu Asp Met Gly Ile Tyr
                85               90               95

Tyr Cys Thr Gly Gly Met Asp Tyr Trp Gly Gln Gly Thr Ser Val Thr
            100              105              110

Val Ser Ser
        115

<210> SEQ ID NO 55
<211> LENGTH: 115
<212> TYPE: PRT
<213> ORGANISM: Artificial Sequence
<220> FEATURE:
<223> OTHER INFORMATION: VH for huC1D1-V1 - huC1D1-V12
<220> FEATURE:
<221> NAME/KEY: misc_feature
<222> LOCATION: (49)..(49)
<223> OTHER INFORMATION: Xaa can be Ala or Gly
<220> FEATURE:
<221> NAME/KEY: misc_feature
<222> LOCATION: (81)..(81)
<223> OTHER INFORMATION: Xaa can be Ala or Val

<400> SEQUENCE: 55
```

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Asp Asn
            20                  25                  30

Trp Met Asn Trp Val Arg Gln Ala Pro Gly Lys Gly Leu Glu Trp Val
            35                  40                  45

Xaa Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ile
65                  70                  75                  80

Xaa Tyr Leu Gln Met Asn Ser Leu Lys Thr Glu Asp Thr Ala Val Tyr
                85                  90                  95

Tyr Cys Thr Gly Gly Met Asp Tyr Trp Gly Gln Gly Thr Thr Val Thr
            100                 105                 110

Val Ser Ser
        115
```

```
<210> SEQ ID NO 56
<211> LENGTH: 108
<212> TYPE: PRT
<213> ORGANISM: Artificial Sequence
<220> FEATURE:
<223> OTHER INFORMATION: VL for mouse and chimeric C1D1

<400> SEQUENCE: 56
```

```
Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Ile Ile Tyr Gly Ala
            20                  25                  30

Leu Asn Trp Tyr Gln Gln Lys Gln Gly Lys Ser Pro Gln Leu Leu Ile
            35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Ala Ala Thr Tyr Tyr Cys Gln Lys Ile Leu Ser Pro Pro Pro
                85                  90                  95

Trp Thr Phe Gly Gly Gly Thr Lys Leu Glu Ile Lys
            100                 105
```

```
<210> SEQ ID NO 57
<211> LENGTH: 108
<212> TYPE: PRT
<213> ORGANISM: Artificial Sequence
<220> FEATURE:
<223> OTHER INFORMATION: VL for huC1D1-V1 - huC1D1-V12
<220> FEATURE:
<221> NAME/KEY: misc_feature
<222> LOCATION: (43)..(43)
<223> OTHER INFORMATION: Xaa can be Ser or Val
<220> FEATURE:
<221> NAME/KEY: misc_feature
<222> LOCATION: (58)..(58)
<223> OTHER INFORMATION: Xaa can be Met or Val
<220> FEATURE:
<221> NAME/KEY: misc_feature
<222> LOCATION: (69)..(69)
<223> OTHER INFORMATION: Xaa can be Arg or Thr
<220> FEATURE:
<221> NAME/KEY: misc_feature
<222> LOCATION: (71)..(71)
<223> OTHER INFORMATION: Xaa can be Tyr or Phe
```

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Ile Ile Tyr Gly Ala
            20                  25                  30

Leu Asn Trp Tyr Gln Gln Lys Pro Gly Lys Xaa Pro Lys Leu Leu Ile
        35                  40                  45

Tyr Gly Ala Thr Asn Leu Ala Asp Gly Xaa Pro Ser Arg Phe Ser Gly
    50                  55                  60

Ser Gly Ser Gly Xaa Asp Xaa Thr Leu Thr Ile Ser Ser Leu Gln Pro
65                  70                  75                  80

Glu Asp Val Ala Thr Tyr Tyr Cys Gln Lys Ile Leu Ser Pro Pro Pro
                85                  90                  95

Trp Thr Phe Gly Gly Gly Thr Lys Val Glu Ile Lys
            100                 105

<210> SEQ ID NO 58
<211> LENGTH: 118
<212> TYPE: PRT
<213> ORGANISM: Artificial Sequence
<220> FEATURE:
<223> OTHER INFORMATION: VH for mouse and chimeric D1D5

<400> SEQUENCE: 58

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Ser Val Tyr Tyr Ala Asp Thr Glu
    50                  55                  60

Thr Gly Arg Phe Thr Ile Ser Arg Glu Asp Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Ser Gly Leu Pro Tyr Ala Met Asp Tyr Trp Gly Gln Gly Thr
            100                 105                 110

Ser Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: VH for huD1D5-V1 - huD1D5-V12
<220> FEATURE:
<221> NAME/KEY: misc_feature
<222> LOCATION: (45)..(45)
<223> OTHER INFORMATION: Xaa can be Pro or Leu
<220> FEATURE:
<221> NAME/KEY: misc_feature
<222> LOCATION: (49)..(49)
<223> OTHER INFORMATION: Xaa can be Ala or Ser
<220> FEATURE:
<221> NAME/KEY: misc_feature
<222> LOCATION: (74)..(74)
<223> OTHER INFORMATION: Xaa can be Asp or Asn

<400> SEQUENCE: 59

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Ala Trp Val Arg Gln Ala Pro Gly Lys Gly Xaa Glu Trp Val
        35                  40                  45

Xaa Phe Ile Ser Asn Leu Ala Tyr Ser Val Tyr Tyr Ala Asp Thr Glu
    50                  55                  60

Thr Gly Arg Phe Thr Ile Ser Arg Asp Xaa Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Leu Pro Tyr Ala Met Asp Tyr Trp Gly Gln Gly Thr
        100                 105                 110

Thr Val Thr Val Ser Ser
        115
```

```
<210> SEQ ID NO 60
<211> LENGTH: 107
<212> TYPE: PRT
<213> ORGANISM: Artificial Sequence
<220> FEATURE:
<223> OTHER INFORMATION: VL for mouse and chimeric D1D5

<400> SEQUENCE: 60
```

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Ile Ser Arg Leu His Ser Gly Val Pro Ser Arg Phe Ser Gly
    50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly Arg Met Leu Pro Trp
                85                  90                  95

Thr Phe Gly Gly Gly Thr Arg Leu Glu Ile Lys
        100                 105
```

```
<210> SEQ ID NO 61
<211> LENGTH: 107
<212> TYPE: PRT
<213> ORGANISM: Artificial Sequence
<220> FEATURE:
<223> OTHER INFORMATION: VL for huD1D5-V1 - huD1D5-V12
<220> FEATURE:
<221> NAME/KEY: misc_feature
<222> LOCATION: (43)..(43)
<223> OTHER INFORMATION: Xaa can be Thr or Val
<220> FEATURE:
<221> NAME/KEY: misc_feature
<222> LOCATION: (44)..(44)
<223> OTHER INFORMATION: Xaa can be Val or Pro
<220> FEATURE:
<221> NAME/KEY: misc_feature
<222> LOCATION: (87)..(87)
<223> OTHER INFORMATION: Xaa can be Phe or Tyr

<400> SEQUENCE: 61
```

```
Asp Ile Gln Met Thr Gln Ser Pro Ser Ser Leu Ser Ala Ser Val Gly
```

```
1               5               10              15

Asp Arg Val Thr Ile Thr Cys Arg Ala Ser Gln Asp Ile Ser Asn Tyr
            20              25              30

Leu Asn Trp Tyr Gln Gln Lys Pro Gly Lys Xaa Xaa Lys Leu Leu Ile
        35              40              45

Tyr Tyr Ile Ser Arg Leu His Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Val Ala Thr Tyr Xaa Cys Gln Gln Gly Arg Met Leu Pro Trp
            85              90              95

Thr Phe Gly Gly Gly Thr Lys Val Glu Ile Lys
            100             105
```

<210> SEQ ID NO 62
<211> LENGTH: 115
<212> TYPE: PRT
<213> ORGANISM: Artificial Sequence
<220> FEATURE:
<223> OTHER INFORMATION: VH for mouse C1G4

<400> SEQUENCE: 62

```
Glu Val Lys Leu Asp Glu Thr Gly Gly Gly Leu Val Gln Pro Gly Arg
1               5               10              15

Pro Ile Lys Leu Ser Cys Val Ala Ser Gly Phe Thr Phe Ser Asp Asn
            20              25              30

Trp Met Asn Trp Val Arg Gln Ser Pro Glu Lys Gly Leu Glu Trp Val
        35              40              45

Ala Gln Ile Arg Asn Lys Pro Tyr Asn Tyr Glu Thr Tyr Tyr Ser Asp
    50              55              60

Ser Val Lys Gly Arg Phe Thr Ile Ser Arg Asp Asp Ser Lys Ser Ser
65              70              75              80

Val Tyr Leu Gln Met Asn Asn Leu Arg Thr Lys Asp Met Gly Ile Tyr
            85              90              95

Tyr Cys Thr Gly Gly Phe Thr Tyr Trp Gly Gln Gly Thr Leu Val Thr
            100             105             110

Val Ser Ala
        115
```

<210> SEQ ID NO 63
<211> LENGTH: 107
<212> TYPE: PRT
<213> ORGANISM: Artificial Sequence
<220> FEATURE:
<223> OTHER INFORMATION: VL for mouse C1G4

<400> SEQUENCE: 63

```
Asp Ile Gln Met Thr Gln Ser Pro Pro Ser Leu Ser Ala Ser Val Gly
1               5               10              15

Glu Thr Val Thr Ile Thr Cys Gly Ala Ser Glu Asn Ile Tyr Gly Gly
            20              25              30

Leu Asn Trp Tyr Gln Arg Lys Gln Gly Lys Ser Pro Gln Leu Leu Ile
        35              40              45

Tyr Gly Ala Thr Asn Leu Ala Asp Gly Met Ser Ser Arg Phe Ser Gly
    50              55              60

Ser Gly Ser Gly Arg Gln Tyr Ser Leu Lys Ile Ser Arg Leu His Pro
65              70              75              80
```

-continued

```
Asp Asp Val Ala Thr Tyr Tyr Cys Gln Asn Val Leu Asn Thr Pro Tyr
                85                  90                  95

Thr Phe Gly Gly Gly Thr Lys Leu Glu Ile Lys
            100                 105

<210> SEQ ID NO 64
<211> LENGTH: 122
<212> TYPE: PRT
<213> ORGANISM: Artificial Sequence
<220> FEATURE:
<223> OTHER INFORMATION: VH for mouse D1A7

<400> SEQUENCE: 64

Gln Val Thr Leu Lys Glu Ser Gly Pro Gly Met Leu Gln Pro Ser Gln
1               5                   10                  15

Thr Leu Ser Leu Thr Cys Ser Phe Ser Gly Phe Ser Leu Ser Ser Ser
                20                  25                  30

Lys Leu Gly Val Gly Trp Ile Arg Gln Pro Ala Gly Lys Gly Leu Glu
            35                  40                  45

Trp Leu Ala His Ile Trp Trp Asn Asp Asp Asn Tyr Tyr Val Pro Ser
        50                  55                  60

Leu Lys Ser Arg Leu Thr Ile Ser Lys Asp Thr Ser Asn Asn Gln Val
65                  70                  75                  80

Phe Leu Lys Ile Thr Asn Val Asp Ala Ala Asp Thr Ala Thr Tyr Tyr
                85                  90                  95

Cys Val Gln Val Pro Tyr Tyr Thr Thr Gln Pro Trp Phe Ala Tyr Trp
                100                 105                 110

Gly Gln Gly Thr Leu Val Thr Val Ser Ala
        115                 120

<210> SEQ ID NO 65
<211> LENGTH: 107
<212> TYPE: PRT
<213> ORGANISM: Artificial Sequence
<220> FEATURE:
<223> OTHER INFORMATION: VL for mouse D1A7

<400> SEQUENCE: 65

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Leu Gln Asn Gln Gly Arg Ser Pro Gln Leu Leu Val
            35                  40                  45

Tyr Asn Thr Glu Thr Leu Ala Asp Gly Val Ser Ser Arg Phe Ser Gly
        50                  55                  60

Ser Gly Ser Gly Thr Gln Tyr Phe Leu Lys Ile Ser Ser Leu Gln Pro
65                  70                  75                  80

Glu Asp Phe Gly Thr Tyr Tyr Cys Gln His Leu Trp Ser Thr Pro Trp
                85                  90                  95

Thr Phe Gly Gly Gly Thr Lys Leu Glu Ile Lys
            100                 105

<210> SEQ ID NO 66
<211> LENGTH: 119
<212> TYPE: PRT
<213> ORGANISM: Artificial Sequence
<220> FEATURE:
<223> OTHER INFORMATION: VH for mouse D1B6
```

<400> SEQUENCE: 66

Glu Val Gln Leu Gln Gln Ser Gly Pro Glu Leu Val Lys Pro Gly Ala
1               5                   10                  15

Ser Val Lys Leu Ser Cys Lys Ala Ser Gly Asn Thr Phe Thr Thr Tyr
            20                  25                  30

Val Leu Asn Trp Val Lys Gln Lys Pro Gly Gln Gly Leu Glu Trp Ile
        35                  40                  45

Gly Tyr Phe Asn Pro Tyr Asn Asp Gly Ile Lys Tyr Asn Glu Lys Phe
    50                  55                  60

Lys Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Phe Glu Gly Gly Gly Tyr Ala Met Asp Tyr Trp Gly Gln Gly
            100                 105                 110

Thr Ser Val Thr Val Ser Ser
        115

<210> SEQ ID NO 67
<211> LENGTH: 111
<212> TYPE: PRT
<213> ORGANISM: Artificial Sequence
<220> FEATURE:
<223> OTHER INFORMATION: VL for mouse D1B6

<400> SEQUENCE: 67

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Gly Thr Ser
            20                  25                  30

Arg Asn Thr Tyr Ile His Trp Tyr Gln Gln Lys Leu Gly Gln Pro Pro
        35                  40                  45

Lys Leu Leu Ile Lys Tyr Ala Ser Asp Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 68
<211> LENGTH: 114
<212> TYPE: PRT
<213> ORGANISM: Artificial Sequence
<220> FEATURE:
<223> OTHER INFORMATION: VH for mouse D1B8

<400> SEQUENCE: 68

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Asn Asn Asn Thr Arg Tyr Asn Glu Lys Phe
    50                  55                  60

-continued

```
Lys Gly Lys Ala Thr Leu Thr Ile Asp Thr Ser Ser Ser Thr Ala Phe
65                  70                  75                  80

Met His Leu Ser Ser Leu Thr Ser Glu Asp Ser Ala Val Tyr Phe Cys
                85                  90                  95

Ala Arg Tyr Tyr Phe Asp Tyr Trp Gly Gln Gly Thr Thr Leu Thr Val
            100                 105                 110

Ser Ser

<210> SEQ ID NO 69
<211> LENGTH: 107
<212> TYPE: PRT
<213> ORGANISM: Artificial Sequence
<220> FEATURE:
<223> OTHER INFORMATION: VL for mouse D1B8

<400> SEQUENCE: 69

Asp Ile Gln Met Thr Gln Ser Pro Ser Ser Leu Ser Ala Ser Leu Gly
1               5                   10                  15

Glu Arg Ile Ser Leu Thr Cys Arg Ala Ser Gln Glu Ile Thr Gly Tyr
                20                  25                  30

Leu Ser Trp Leu Gln Gln Lys Pro Asp Gly Thr Ile Lys Arg Leu Ile
            35                  40                  45

Tyr Ala Ala Ser Thr Leu Asp Ser Gly Val Pro Gln Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 70
<211> LENGTH: 119
<212> TYPE: PRT
<213> ORGANISM: Artificial Sequence
<220> FEATURE:
<223> OTHER INFORMATION: VH for mouse D1G6

<400> SEQUENCE: 70

Glu Val Gln Leu Gln Gln Ser Gly Pro Glu Leu Val Lys Pro Gly Ala
1               5                   10                  15

Ser Val Lys Leu Ser Cys Lys Ala Ser Gly Asn Thr Phe Thr Thr Tyr
                20                  25                  30

Val Leu Asn Trp Val Lys Gln Lys Pro Gly Gln Gly Leu Glu Trp Ile
            35                  40                  45

Gly Tyr Phe Asn Pro Tyr Asn Asp Ala Ile Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Phe Glu Gly Gly Gly Tyr Ala Met Asp Tyr Trp Gly Gln Gly
            100                 105                 110

Thr Ser Val Thr Val Ser Ser
            115

<210> SEQ ID NO 71
<211> LENGTH: 111
```

-continued

```
<212> TYPE: PRT
<213> ORGANISM: Artificial Sequence
<220> FEATURE:
<223> OTHER INFORMATION: VL for mouse D1G6

<400> SEQUENCE: 71

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Gly Thr Ser
            20                  25                  30

Ser Tyr Ser Tyr Ile His Trp Tyr Gln Gln Lys Pro Gly Gln Pro Pro
        35                  40                  45

Lys Leu Leu Ile Lys Tyr Ala Ser Asp Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 72
<211> LENGTH: 119
<212> TYPE: PRT
<213> ORGANISM: Artificial Sequence
<220> FEATURE:
<223> OTHER INFORMATION: VH for mouse D1H3

<400> SEQUENCE: 72

Gln Val Gln Leu Gln Gln Pro Gly Ala Glu Leu Val Asn Pro Gly Ala
1               5                   10                  15

Ser Val Lys Leu Ser Cys Lys Ala Ser Gly Tyr Thr Phe Thr Ser Tyr
            20                  25                  30

Trp Leu His Trp Val Lys Gln Arg Pro Gly Arg Gly Leu Glu Trp Ile
        35                  40                  45

Gly Arg Ile Asp Pro Asn Arg Gly Thr Ile Tyr Tyr Asn Glu Lys Phe
    50                  55                  60

Asn Asn Lys Ala Thr Val Thr Val Asp Lys Pro Ser Asn Thr Ala Tyr
65                  70                  75                  80

Met Gln Leu Ser Arg Leu Thr Leu Glu Asp Ser Ala Val Tyr Tyr Cys
                85                  90                  95

Ala Arg Gly Gly Ser Asn Phe Tyr Ala Met Asp Tyr Trp Gly Gln Gly
            100                 105                 110

Thr Ser Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: VL for mouse D1H3

<400> SEQUENCE: 73

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Gly Glu Ser Pro Gln Leu Leu Val
```

```
        35              40              45
Tyr Asn Ala Lys Thr Leu Ala Glu Gly Val Pro Ser Arg Phe Ser Gly
    50              55              60

Ser Gly Ser Gly Thr Gln Phe Ser Leu Lys Ile Asn Ser Leu Gln Pro
65              70              75              80

Glu Asp Phe Gly Ser Tyr Tyr Cys Gln Asn His Asp Gly Ile Pro Phe
                85              90              95

Thr Phe Gly Ser Gly Thr Lys Leu Glu Ile Lys
            100             105

<210> SEQ ID NO 74
<211> LENGTH: 119
<212> TYPE: PRT
<213> ORGANISM: Artificial Sequence
<220> FEATURE:
<223> OTHER INFORMATION: VH for mouse D1H4

<400> SEQUENCE: 74

Glu Val Gln Leu Gln Gln Ser Gly Pro Val Leu Val Lys Pro Gly Ala
1               5               10              15

Ser Val Lys Met Ser Cys Lys Ala Ser Gly Tyr Thr Phe Thr Asp Tyr
            20              25              30

Tyr Met Asn Trp Val Lys Gln Ser His Gly Lys Ser Leu Glu Trp Ile
        35              40              45

Gly Ala Ile Asn Pro Asp His Gly Gly Ser Ser Tyr Asn Gln Lys Phe
    50              55              60

Lys Gly Lys Ala Thr Leu Thr Val Asp Lys Ser Ser Ser Thr Ala Tyr
65              70              75              80

Met Glu Leu Asn Ser Leu Thr Ser Glu Asp Ser Ala Val Tyr Tyr Cys
                85              90              95

Ala Arg Asp Gly Ser Ile His Tyr Val Met Asp Asp Trp Gly Gln Gly
            100             105             110

Thr Ser Val Thr Val Ser Ser
        115

<210> SEQ ID NO 75
<211> LENGTH: 113
<212> TYPE: PRT
<213> ORGANISM: Artificial Sequence
<220> FEATURE:
<223> OTHER INFORMATION: VL for mouse D1H4

<400> SEQUENCE: 75

Asp Ile Val Met Ser Gln Ser Pro Ser Ser Leu Thr Val Ser Ala Gly
1               5               10              15

Asp Lys Val Thr Met Ser Cys Lys Ser Ser Gln Ser Leu Leu His Ser
            20              25              30

Gly Asn Gln Lys Asn Tyr Leu Ala Trp Tyr Gln Gln Lys Pro Trp Gln
        35              40              45

Pro Pro Lys Leu Leu Ile Tyr Gly Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Tyr Cys Gln Asn
                85              90              95

Asp Tyr Gly Tyr Pro Tyr Thr Phe Gly Gly Gly Thr Lys Leu Glu Ile
            100             105             110
```

Lys

```
<210> SEQ ID NO 76
<211> LENGTH: 119
<212> TYPE: PRT
<213> ORGANISM: Artificial Sequence
<220> FEATURE:
<223> OTHER INFORMATION: VH for mouse D2A4

<400> SEQUENCE: 76

Gln Val Gln Leu Gln Gln Pro Gly Ala Glu Leu Val Lys Pro Gly Ser
1               5                   10                  15

Ser Val Asn Leu Ser Cys Lys Ala Ser Gly Tyr Thr Phe Thr Ser Tyr
            20                  25                  30

Trp Val His Trp Val Lys Gln Gly Pro Gly Arg Gly Leu Glu Trp Ile
        35                  40                  45

Gly Arg Ile Asp Pro Asn Arg Gly Gly Thr Tyr Tyr Asn Glu Asn Phe
    50                  55                  60

Lys Thr Lys Ala Ala Leu Thr Val Asp Ser Pro Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Gly Leu Asn Tyr Tyr Ala Leu Asp Tyr Trp Gly Gln Gly
            100                 105                 110

Thr Ser Val Thr Val Ser Ser
        115

<210> SEQ ID NO 77
<211> LENGTH: 107
<212> TYPE: PRT
<213> ORGANISM: Artificial Sequence
<220> FEATURE:
<223> OTHER INFORMATION: VL for mouse D2A4

<400> SEQUENCE: 77

Asp Ile Gln Met Thr Gln Ser Pro Ala Ser Leu Phe Ala Ser Leu Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Asn Thr Leu Thr Glu Gly Val Pro Ser Ser Phe Ser Gly
    50                  55                  60

Ser Gly Ser Gly Thr Gln Phe Ser Leu Lys Ile Asn Thr Leu Gln Pro
65                  70                  75                  80

Glu Asp Phe Gly Thr Tyr Tyr Cys Gln His His Tyr Gly Ile Pro Phe
                85                  90                  95

Thr Phe Gly Ser Gly Thr Lys Leu Glu Ile Lys
            100                 105

<210> SEQ ID NO 78
<211> LENGTH: 327
<212> TYPE: PRT
<213> ORGANISM: Artificial Sequence
<220> FEATURE:
<223> OTHER INFORMATION: Heavy chain constant region

<400> SEQUENCE: 78

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                    165                 170                 175

Asn Ser Thr Tyr Arg Val Val Ser Val Leu Thr Val Leu His Gln Asp
                    180                 185                 190

Trp Leu Asn Gly Lys Glu Tyr Lys Cys Lys Val Ser Asn Lys Gly Leu
                    195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
                    260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                    325
```

```
<210> SEQ ID NO 79
<211> LENGTH: 107
<212> TYPE: PRT
<213> ORGANISM: Artificial Sequence
<220> FEATURE:
<223> OTHER INFORMATION: Light chain constant region

<400> SEQUENCE: 79
```

```
Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 80
<211> LENGTH: 345
<212> TYPE: DNA
<213> ORGANISM: Artificial Sequence
<220> FEATURE:
<223> OTHER INFORMATION: VH for mouse and chimeric C1D1

<400> SEQUENCE: 80

```
gaggtgaagc tggatgagac tggaggaggc ttggtgcaac ctgggaggcc cctgaaactc    60
tcctgtgttg cctctggatt cacttttagt gacaactgga tgaactgggt ccgccagtct   120
ccagagaaag gactggagtg ggtagcacaa attagaaaca aaccttataa ttatgaaaca   180
tattattcag attctgtgaa aggcagattc accatctcaa gagatgattc caaaagtagt   240
gtctacctgc aaatgaacaa cttaagagtt gaagacatgg gtatctatta ctgtacaggc   300
gggatggact actggggtca aggaacctca gtcaccgtct cctca                   345
```

<210> SEQ ID NO 81
<211> LENGTH: 345
<212> TYPE: DNA
<213> ORGANISM: Artificial Sequence
<220> FEATURE:
<223> OTHER INFORMATION: VH for mouse and chimeric C1D1

<400> SEQUENCE: 81

```
gaggtgaagc tggacgagac cggcggcggc ctggtgcaac aggaagacc cctgaagctg     60 tcctgcgtgg ccagcggctt cacattcagc gacaattgga tgaactgggt gaggcagagc   120
cctgagaagg gcctggagtg ggtggcccag atcagaaata gccttacaa ctacgagacc    180 tactacagcg actccgtgaa gggcaggttc acaatcagca gagacgacag caagtccagc   240
gtgtacctgc agatgaacaa tctgagagtg gaggacatgg gcatctacta ctgtaccggc   300
ggcatggatt actggggcca gggcacaagc gtgaccgtgt ccagc                   345
```

<210> SEQ ID NO 82
<211> LENGTH: 345
<212> TYPE: DNA
<213> ORGANISM: Artificial Sequence
<220> FEATURE:
<223> OTHER INFORMATION: VH for huC1D1-V4, huC1D1-V8 and huC1D1-V12

<400> SEQUENCE: 82

```
gaggtgcagc tggtggagtc cggcggcgga ctggtgcagc ctggaagaag cctgagactg     60
tcctgtaccg ccagcggctt caccttctcc gacaactgga tgaattgggt gaggcaggcc   120
cctggcaagg gcctggagtg ggtgggacag atcagaaata gccctacaa ttacgagaca    180 tactactccg attccgtgaa gggcagattc accatctcca gggatgatag caagagcatc   240
gcctacctgc agatgaattc cctgaagacc gaggacaccg ccgtgtacta ctgtaccggc   300
ggcatggact actggggcca gggcaccaca gtgacagtgt ccagc                   345
```

```
<210> SEQ ID NO 83
<211> LENGTH: 324
<212> TYPE: DNA
<213> ORGANISM: Artificial Sequence
<220> FEATURE:
<223> OTHER INFORMATION: VL for mouse and chimeric C1D1

<400> SEQUENCE: 83
gacattcaga tgactcagtc tccagcttca ctgtctgcat ctgtgggaga aactgtcacc      60
atcacatgtg gagcaagtga gattatttac ggtgctttaa attggtatca gcagaaacag     120
ggaaaatctc ctcagctcct gatctatggt gcaaccaact ggcagatggg catgtcatcg     180
aggttcagtg gcagtggatc tggtagacaa tattctctca agatcagtag cctgcatcct     240
gacgatgctg caacatatta ctgtcaaaaa atattaagtc ctcctccgtg gacgttcggt     300
ggaggcacca agctggagat caaa                                            324

<210> SEQ ID NO 84
<211> LENGTH: 324
<212> TYPE: DNA
<213> ORGANISM: Artificial Sequence
<220> FEATURE:
<223> OTHER INFORMATION: VL for mouse and chimeric C1D1

<400> SEQUENCE: 84
gacatccaga tgacacagag ccccgccagc ctgtccgcca gcgttggaga gaccgtgaca      60
atcacatgtg gcgcctccga gatcatctac ggcgccctga attggtatca acagaagcag     120
ggcaagagcc cccagctgct gatctacggc gctaccaatc tggccgacgg catgagctcc     180
aggttctccg gcagcggcag cggcaggcag tacagcctga agatctccag cctgcacccc     240
gacgacgccg ccacatacta ctgccagaag atcctgtccc cccctccttg gacattcggc     300
ggcggcacca agctggagat caag                                            324

<210> SEQ ID NO 85
<211> LENGTH: 324
<212> TYPE: DNA
<213> ORGANISM: Artificial Sequence
<220> FEATURE:
<223> OTHER INFORMATION: VL for huC1D1-V5 - huC1D1-V8

<400> SEQUENCE: 85
gatatccaga tgacacagtc cccctcctcc ctgagcgcct ccgtgggaga cagagtgacc      60
atcacctgtg gcgcctccga gatcatctac ggcgccctga attggtatca acagaagccc     120
ggcaagagcc ccaagctgct gatctacggc gctacaaacc tggccgatgg cgtgccttcc     180
aggtttagcg gctccggctc cggcaccgac ttcaccctga ccatctcctc cctgcagccc     240
gaggatgtgg ccacatacta ctgtcagaag atcctgagcc cccccccttg gaccttcggc     300
ggaggaacaa aggtggagat caag                                            324

<210> SEQ ID NO 86
<211> LENGTH: 354
<212> TYPE: DNA
<213> ORGANISM: Artificial Sequence
<220> FEATURE:
<223> OTHER INFORMATION: VH for mouse and chimeric D1D5

<400> SEQUENCE: 86
gaggtgaagc tggtggagtc tgggggaggc ttagtgaagc ctggagggtc cctgaaactc      60
tcctgtgcag cctctggatt cactttcagt gactacggaa tggcgtgggt tcgacaggct     120
```

```
ccagggaagg ggcctgagtg ggtagcattc attagtaatt tggcatatag tgtctactat      180
gcagacactg agacgggccg attcaccatc tctagagagg atgccaagaa caccctgtac      240
ttggaaatga gcagtctgag gtctgaggac acagccatgt attactgtgc aagaagtgga      300
ctaccctatg ctatggacta ctggggtcaa ggaacctcag tcaccgtctc ctca           354

<210> SEQ ID NO 87
<211> LENGTH: 354
<212> TYPE: DNA
<213> ORGANISM: Artificial Sequence
<220> FEATURE:
<223> OTHER INFORMATION: VH for mouse and chimeric D1D5

<400> SEQUENCE: 87
gaggtgaagc tggtggagtc cggcggcggc ctggtgaagc caggaggaag cctgaagctg       60
tcctgcgccg cctccggctt cacattctcc gactacggca tggcctgggt gaggcaggcc      120
cctggaaagg gccctgagtg ggtggccttc atctccaatc tggcctacag cgtgtactac      180
gccgataccg agacaggcag gttcaccatc tccagagagg acgccaagaa tacactgtac      240
ctggagatga gcagcctgag atccgaggac acagccatgt actactgcgc caggagcggc      300
ctgccttacg ccatggatta ctggggccag ggcacaagcg tgaccgtgag ctcc           354

<210> SEQ ID NO 88
<211> LENGTH: 354
<212> TYPE: DNA
<213> ORGANISM: Artificial Sequence
<220> FEATURE:
<223> OTHER INFORMATION: VH for huD1D5-V1, huD1D5-V5 and huD1D5-V9

<400> SEQUENCE: 88
gaggtgcagc tggtggagtc cggcggcgga ctggtgaagc ctggcggatc cctgaggctg       60
tcctgtgccg cctccggctt caccttctcc gactacggca tggcctgggt gaggcaggcc      120
cctggaaagg gccccgagtg ggtggctttc atctccaatc tggcctacag cgtgtactac      180
gccgatacag agacaggcag gttcacaatc agcagggatg acgccaagaa cagcctgtac      240
ctgcagatga actccctgag ggccgaggat accgccgtgt actactgtgc caggtccggc      300
ctgccctacg ccatggatta ctggggccag ggcacaacag tgacagtgag cagc           354

<210> SEQ ID NO 89
<211> LENGTH: 321
<212> TYPE: DNA
<213> ORGANISM: Artificial Sequence
<220> FEATURE:
<223> OTHER INFORMATION: VL for mouse and chimeric D1D5

<400> SEQUENCE: 89
gatatccaga tgacacagac tacatcctcc ctgtctgcct cgctgggaga cagagtcacc       60
atcagttgca gggccagtca ggacattagc aattatttaa actggtatca gcagaaacca      120
gatggaactg ttaaactcct gatctactac atatcaagat tacactcagg agtcccatca      180
aggttcagtg gcagtgggtc tgggacagat ttttctctca ccattagcaa cctggaacaa      240
gaagatattg ccacttactt ttgccaacag ggtcgtatgc ttccgtggac gttcggtgga      300
ggcaccaggc tggaaatcaa a                                               321

<210> SEQ ID NO 90
<211> LENGTH: 321
<212> TYPE: DNA
```

```
<213> ORGANISM: Artificial Sequence
<220> FEATURE:
<223> OTHER INFORMATION: VL for mouse and chimeric D1D5

<400> SEQUENCE: 90
gatatccaga tgacccagac aacaagcagc ctgagcgcct ccctgggcga tagagtgaca      60
atctcctgca gggccagcca ggatatcagc aactacctga attggtatca acagaagcct     120
gatggcaccg tgaagctgct gatctactac atctccagac tgcacagcgg cgtgcccagc     180
agattctccg gcagcggcag cggcaccgac ttctccctga ccatctccaa tctggagcag     240
gaggatatcg ccacatactt ctgccagcag ggcagaatgc tgccttggac attcggcggc     300
ggcaccagac tggagatcaa g                                               321

<210> SEQ ID NO 91
<211> LENGTH: 321
<212> TYPE: DNA
<213> ORGANISM: Artificial Sequence
<220> FEATURE:
<223> OTHER INFORMATION: VL for huD1D5-V9 - huD1D5-V12

<400> SEQUENCE: 91
gacatccaga tgacacagtc ccctagcagc ctgagcgcca gcgtgggcga cagggtgacc      60
atcacatgta gagccagcca ggacatctcc aattacctga attggtatca acagaagccc     120
ggcaaggtgc ctaagctgct gatctactac atcagcaggc tgcactccgg cgtgccctcc     180
agattcagcg gcagcggctc cggcaccgat tttaccctga caatctccag cctgcagcct     240
gaggacgtgg ccacatacta ctgccagcag ggcaggatgc tgccttggac attcggcggc     300
ggcacaaagg tggagatcaa g                                               321

<210> SEQ ID NO 92
<211> LENGTH: 984
<212> TYPE: DNA
<213> ORGANISM: Artificial Sequence
<220> FEATURE:
<223> OTHER INFORMATION: Heavy chain constant region

<400> SEQUENCE: 92
gccagcacaa agggcccttc cgtgtttccc ctggccccct gcagcaggag cacctctgag      60
tccaccgccg ccctgggctg tctggtgaag gactactttc ccgagcccgt gaccgtgagc     120
tggaattccg gcgccctgac atccggcgtg cacaccttcc ccgccgtgct gcagtcctcc     180
ggcctgtaca gcctgagctc cgtggtgaca gtgccttcct cctccctggg caccaagacc     240
tacacatgta atgtggatca caagcccagc aacacaaagg tggataagag agtggagtcc     300
aagtacggcc ctccttgccc tccctgtcct gccccagagt tcctgggcggc ccctctgtg      360 ttcctgttcc cccctaagcc caaggacaca ctgatgatct ccaggacccc tgaggtgacc     420
tgcgtggtgg tggacgtgag ccaggaggac cctgaggtgc agttcaattg gtacgtggat     480
ggcgtggagg tgcacaatgc caagacaaag cccagagagg agcagtttaa ttccacatac     540
agggtggtgt ccgtgctgac cgtgctgcac caggattggc tgaacggcaa ggagtacaag     600
tgtaaggtga gcaacaaggg cctgccttcc tccatcgaga gacaatcag caaggccaag      660 ggccagccta gggagcccca ggtgtacaca ctgcctccca gccaggagga gatgaccaag     720
aaccaggtga gcctgacctg cctggtgaag ggcttctacc ctagcgacat cgccgtggag     780
tgggagtcca acggcagcc cgagaataac tacaagacaa cacccccgt gctggattcc      840 gatggcagct ctttctgta ctccaggctg accgtggata gagcaggtg gcaggagggc      900
```

-continued

```
aatgtgttca gctgctccgt gatgcacgag gccctgcaca atcactacac ccagaagagc      960
ctgtccctga gcctgggcaa gtga                                            984

<210> SEQ ID NO 93
<211> LENGTH: 324
<212> TYPE: DNA
<213> ORGANISM: Artificial Sequence
<220> FEATURE:
<223> OTHER INFORMATION: Light chain constant region

<400> SEQUENCE: 93
cgtacggtgg cggcgccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttga                                            324
```

ANTIBODIES BINDING CTLA4 AND USES THEREOF

RELATED APPLICATIONS AND INCORPORATION BY REFERENCE

This application claims priority to U.S. provisional patent application Ser. No. 63/008,931 filed Apr. 13, 2020.

The foregoing application, and all documents cited therein or during their prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Apr. 12, 2021, is named 55532_00077SL.txt and is 51,634 bytes in size.

FIELD OF THE INVENTION

The present disclosure relates generally to an isolated monoclonal antibody, particularly a mouse, chimeric or humanized monoclonal antibody, or an antigen-binding portion thereof, that specifically binds to human CTLA4 with high affinity and functionality. A nucleic acid molecule encoding the antibody or the antigen-binding portion thereof, an expression vector, a host cell and a method for expressing the antibody or the antigen-binding portion thereof are also provided. The present disclosure further provides an immunoconjugate, a bispecific molecule, a chimeric antigen receptor, an oncolytic virus, and a pharmaceutical composition comprising the antibody or the antigen-binding portion thereof, as well as a diagnostic or treatment method using an anti-CTLA4 antibody or antigen-binding portion thereof of the disclosure.

BACKGROUND OF THE INVENTION

Immune checkpoints regulate the immune system, preventing the system from attacking cells indiscriminately. Among the immune checkpoints, cytotoxic T-lymphocyte-associated antigen 4 (CTLA4) and programmed death 1 (PD-1) are two important ones, providing inhibitory signals during immune responses. For example, CTLA4 was reported to stop potentially autoreactive T cells at the initial stage of native T-cell activation, and PD-1 has been found to regulate activated T cells at later stages. These two inhibitory immune checkpoint pathways are also manipulated by tumor cells to evade the immune system's attack (Buchbinder E I, and Desai A. (2016) *Am J Clin Oncol.* 39(1): 98-106).

CTLA4 is CD28 homolog and located primarily in the intracellular compartment in resting naïve T cells. It competes CD28 on CD80/CD86 binding with much higher binding affinity to CD80/CD86 (Chambers C A et al., (2001) *Annu Rev Immunol.* 19:565-594). CD28-CD80/CD86 interaction is important to T cell activation following TCR binding to an antigen displayed in the major histocompatibility complex (MHC) on the surface of an antigen-presenting cell (APC), and sufficient CD28-CD80/CD86 binding levels lead to T cell proliferation, survival and differentiation (Buchbinder EI, and Desai A. (2016) *Am J Clin Oncol.* 39(1):98-106). CTLA4 transfers to the cell surface when there are stimulatory signals from TCR-TCR and CD28-CD80/86 interaction (Linsley P S et al., (1996) *Immunity.* 4:535-543), and CTLA4 binding to CD80/CD86 does not produce stimulatory signals, or even generates inhibitory signals that counteract the stimulatory signals from TCR-TCR and CD28-CD80/86 binding (Chambers C A et al., (2001) *Annu Rev Immunol.* 19:565-594; Egen J G et al., (2002) *Nat Immunol.* 3:611-618; Parry R V et al., (2005) *Mol Cell Biol.* 25:9543-9553; Fallarino F et al., (1998) *J Exp Med.* 188:205-210; Masteller E L et al., (2000) 164:5319-5327). Therefore, the relative amount of CD28-CD80/86 binding versus CTLA4-CD80/86 binding determines whether a T cell will undergo activation or anergy (Krummel M F, and Allison J P. (1995) *J Exp Med.* 182: 459-465). CTLA4 may additionally trigger reverse signaling through CD80/CD86 to induce indoleamine-2,3-dioxygenase, resulting in tryptophan catabolism and T cell proliferation inhibition (Boasso A et al., (2005) *Blood* 105: 1574-1581).

CTLA-4 is also expressed on non-T cells, either normal or neoplastic cells (Laurent S et al., (2010) *Hum Immunol* 71:934-941; Contardi E et al., (2005) *Int J Cancer* 117:538-550). Persistent CTLA-4 expression in the neoplastic cells contributes to hematological and solid tumor progression (Pistillo M P et al., (2003) *Blood* 101:202-209; Kosmaczewska A et al., (2005) *Leukemia* 19:301-304), and CTLA4 pathway blockade has been found effective in decreasing tumor growth (Leach D R et al., (1996) 271:1734-1736; Hirano F et al., (2005) Cancer Res. 65:1089-1096). An anti-CTLA4 antibody, Ipilimumab (YERVOY®), has been approved to treat melanoma, colorectal cancer, hepatocellular carcinoma, malignant pleural mesothelioma, non-small cell lung cancer, and renal cell carcinoma. Tremelimumab, another anti-CTLA4 antibody, is under clinical trials for e.g., mesothelioma, melanoma, and colorectal cancer treatment. CTLA-4 antibodies have also been used in combination with anti-PD-1 antibodies and/or other anti-tumor agents. For example, AGEN1884, also an anti-CTLA-4 antibody, was clinically tested in combination with anti-PD-1 antibodies for treating cervical cancer, angiosarcoma, muscle-invasive bladder cancer, and soft tissue sarcoma (including synovial sarcoma, nerve sheath tumor, and phyllodes tumor) (National Cancer Institute).

Studies have further shown that CTLA-4 is upregulated in chronic infections by e.g., human immunodeficiency virus (HIV), and anti-CTLA-4 therapy alone or with anti-PD-1 have been found to perturb HIV persistence in clinical trials (Thomas A Rasmussen et al., (2021) *Clinical Infectious Diseases* ciaa1530; Colston E et al., (2018) *PLoS One* 13(6):e0198158). Ipilimumab and Nivolumab are also under Phase II trial for treating Epstein-Barr virus (HHV-4) infection. Further, preclinical studies are exploring the effects of ipilimumab on graft versus host disease (GVHD), peripheral nerve injury and neurofibromatosis type I (Von Reckling-hausen's disease).

Ongoing efforts are attempting to find more anti-CTLA4 binding moieties that are more potent or with more desirable characteristics.

Citation or identification of any document in this application is not an admission that such document is available as prior art to the present invention.

SUMMARY OF THE INVENTION

The present disclosure provides an isolated monoclonal antibody, for example, a mouse, human, chimeric or human-ized monoclonal antibody, or an antigen-binding portion thereof, that binds to CTLA4 (e.g., the human CTLA4, and monkey CTLA4) and has comparable, if not higher, binding affinity to CTLA4, comparable, if not higher, blocking activity on CTLA4-CD80/CD86 interaction, and compa-rable activity of promoting T cell responses, as compared to prior art anti-CTLA4 antibodies such as Ipilimumab.

The antibody or antigen-binding portion of the disclosure can be used for a variety of applications, including detection of the CTLA4 protein, and treatment and prevention of CTLA4 associated diseases, such as cancers and infectious diseases.

Accordingly, in one aspect, the disclosure pertains to an isolated monoclonal antibody (e.g., a mouse, chimeric or humanized antibody), or an antigen-binding portion thereof, that binds CTLA4, having i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 2 and 3, respectively; (2) SEQ ID NOs: 7, 8 and 9, respectively; (3) SEQ ID NOs: 1, 2 and 13, respectively; (4) SEQ ID NOs: 16, 17 and 18, respectively; (5) SEQ ID NOs: 22, 23 and 24, respectively; (6) SEQ ID NOs: 28, 29 and 30, respectively; (7) SEQ ID NOs: 22, 34 and 24, respectively; (8) SEQ ID NOs: 36, 37 and 38, respectively; (9) SEQ ID NOs: 42, 43 and 44, respectively; or (10) SEQ ID NOs: 48, 49 and 50, respectively; and/or ii) a light chain variable region that may comprise a VL CDR1 region, a VL CDR2 region and a VL CDR3 region, wherein the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 4, 5 and 6, respectively; (2) SEQ ID NOs: 10, 11 and 12, respectively; (3) SEQ ID NOs: 14, 5 and 15, respectively; (4) SEQ ID NOs: 19, 20 and 21, respectively; (5) SEQ ID NOs: 25, 26 and 27, respectively; (6) SEQ ID NOs: 31, 32 and 33, respectively; (7) SEQ ID NOs: 35, 26 and 27, respectively; (8) SEQ ID NOs: 39, 40 and 41, respectively; (9) SEQ ID NOs: 45, 46 and 47, respectively; or (10) SEQ ID NOs: 51, 52 and 53, respectively.

The antibody or antigen-binding portion thereof of the disclosure may comprise a heavy chain variable region that may comprise a VH CDR1 region, a VH CDR2 region and a VH CDR3 region, and a light chain variable region that may comprise a VL CDR1 region, a VL CDR2 region and a VL CDR3 region, wherein the VH CDR1 region, the VH CDR2 region, the VH CDR3 region, the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 2, 3, 4, 5 and 6, respectively; (2) SEQ ID NOs: 7, 8, 9, 10, 11 and 12, respectively; (3) SEQ ID NOs: 1, 2, 13, 14, 5 and 15, respectively; (4) SEQ ID NOs: 16, 17, 18, 19, 20 and 21, respectively; (5) SEQ ID NOs: 22, 23, 24, 25, 26 and 27, respectively; (6) SEQ ID NOs: 28, 29, 30, 31, 32 and 33, respectively; (7) SEQ ID NOs: 22, 34, 24, 35, 26 and 27, respectively; (8) SEQ ID NOs: 36, 37, 38, 39, 40 and 41, respectively; (9) SEQ ID NOs: 42, 43, 44, 45, 46 and 47, respectively; or (10) SEQ ID NOs: 48, 49, 50, 51, 52 and 53, respectively, wherein the antibody or antigen-binding frag-ment thereof binds to CTLA4.

The heavy chain variable region of the antibody or antigen-binding portion thereof of the disclosure may com-prise an amino acid sequence having at least 85%, 86%, 87%, 88%, 89%, 90%, 91%, 92%, 93%, 94%, 95%, 96%, 97%, 98%, 99% or 100% identity to 54, 55 (X1=A, X2=V; X1=A, X2=A; X1=G, X2=V; X1=G, X2=A), 58, 59 (X1=P, X2=A, X3=D; X1=L, X2=A, X3=N; X1=L, X2=A, X3=D; X1=L, X2=S, X3=N), 62, 64, 66, 68, 70, 72, 74 or 76, wherein the antibody or antigen-binding portion thereof binds to CTLA4. The amino acid sequence of SEQ ID NO: 54 may be encoded by the nucleotide sequence of SEQ ID NOs: 80 or 81. The amino acid sequence of SEQ ID NO: 58 may be encoded by the nucleotide sequence of SEQ ID NOs: 86 or 87. The amino acid sequences of SEQ ID NOs: 55 (X1=G, X2=A) and 59 (X1=P, X2=A, X3=D) may be encoded by the nucleotide sequences of SEQ ID NOs: 82 and 88, respectively.

The light chain variable region of the antibody or antigen-binding portion thereof of the disclosure may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 56, 57 (X1=S, X2=M, X3=R, X4=Y; X1=S, X2=V, X3=T, X4=F; X1=V, X2=V, X3=T, X4=F), 60, 61 (X1=T, X2=V, X3=F; X1=V, X2=P, X3=F; X1=V, X2=P, X3=Y), 63, 65, 67, 69, 71, 73, 75 or 77, wherein the antibody or antigen-binding portion thereof binds to CTLA4. The amino acid sequence of SEQ ID NO: 56 may be encoded by the nucleotide sequence of SEQ ID NO: 83 or 84. The amino acid sequence of SEQ ID NO: 60 may be encoded by a nucleotide sequence of SEQ ID NOs: 89 or 90. The amino acid sequences of SEQ ID NO: 57 (X1=S, X2=V, X3=T, X4=F) and 61 (X1=V, X2=P, X3=Y) may be encoded by the nucleotide sequences of SEQ ID NOs: 85 and 91, respectively.

The antibody or antigen-binding portion thereof of the disclosure may comprise a heavy chain variable region and a light chain variable region having amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 54 and 56, respectively; (2) SEQ ID NOs: 55 (X1=A, X2=V) and 57 (X1=S, X2=M, X3=R, X4=Y), respectively; (3) SEQ ID NOs: 55 (X1=A, X2=A) and 57 (X1=S, X2=M, X3=R, X4=Y), respectively; (4) SEQ ID NOs: 55 (X1=G, X2=V) and 57 (X1=S, X2=M, X3=R, X4=Y), respectively; (5) SEQ ID NOs: 55 (X1=G, X2=A) and 57 (X1=S, X2=M, X3=R, X4=Y), respectively; (6) SEQ ID NOs: 55 (X1=A, X2=V) and 57 (X1=S, X2=V, X3=T, X4=F), respectively; (7) SEQ ID NOs: 55 (X1=A, X2=A) and 57 (X1=S, X2=V, X3=T, X4=F), respectively; (8) SEQ ID NOs: 55 (X1=G, X2=V) and 57 (X1=S, X2=V, X3=T, X4=F), respectively; (9) SEQ ID NOs: 55 (X1=G, X2=A) and 57 (X1=S, X2=V, X3=T, X4=F), respectively; (10) SEQ ID NOs: 55 (X1=A, X2=V) and 57 (X1=V, X2=V, X3=T, X4=F), respectively; (11) SEQ ID NOs: 55 (X1=A, X2=A)

and 57 (X1=V, X2=V, X3=T, X4=F), respectively; (12) SEQ ID NOs: 55 (X1=G, X2=V) and 57 (X1=V, X2=V, X3=T, X4=F), respectively; (13) SEQ ID NOs: 55 (X1=G, X2=A) and 57 (X1=V, X2=V, X3=T, X4=F), respectively; (14) SEQ ID NOs: 58 and 60, respectively; (15) SEQ ID NOs: 59 (X1=P, X2=A, X3=D) and 61 (X1=T, X2=V, X3=F), respectively; (16) SEQ ID NOs: 59 (X1=L, X2=A, X3=N) and 61 (X1=T, X2=V, X3=F), respectively; (17) SEQ ID NOs: 59 (X1=L, X2=A, X3=D) and 61 (X1=T, X2=V, X3=F), respectively; (18) SEQ ID NOs: 59 (X1=L, X2=S, X3=N) and 61 (X1=T, X2=V, X3=F), respectively; (19) SEQ ID NOs: 59 (X1=P, X2=A, X3=D) and 61 (X1=V, X2=P, X3=F), respectively; (20) SEQ ID NOs: 59 (X1=L, X2=A, X3=N) and 61 (X1=V, X2=P, X3=F), respectively; (21) SEQ ID NOs: 59 (X1=L, X2=A, X3=D) and 61 (X1=V, X2=P, X3=F), respectively; (22) SEQ ID NOs: 59 (X1=L, X2=S, X3=N) and 61 (X1=V, X2=P, X3=F), respectively; (23) SEQ ID NOs: 59 (X1=P, X2=A, X3=D) and 61 (X1=V, X2=P, X3=Y), respectively; (24) SEQ ID NOs: 59 (X1=L, X2=A, X3=N) and 61 (X1=V, X2=P, X3=Y), respectively; (25) SEQ ID NOs: 59 (X1=L, X2=A, X3=D) and 61 (X1=V, X2=P, X3=Y), respectively; (26) SEQ ID NOs: 59 (X1=L, X2=S, X3=N) and 61 (X1=V, X2=P, X3=Y), respectively; (27) SEQ ID NOs: 62 and 63, respectively; (28) SEQ ID NOs: 64 and 65, respectively; (29) SEQ ID NOs: 66 and 67, respectively; (30) SEQ ID NOs: 68 and 69, respectively; (31) SEQ ID NOs: 70 and 71, respectively; (32) SEQ ID NOs: 72 and 73, respectively; (33) SEQ ID NOs: 74 and 75, respectively; or (34) SEQ ID NOs: 76 and 77, respectively.

The isolated monoclonal antibody, or the antigen-binding portion thereof, of the present disclosure may comprise a heavy chain and a light chain linked by disulfide bonds, the heavy chain may comprise a heavy chain variable region and a heavy chain constant region, the light chain may comprise a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above, and the antibody or antigen-binding portion thereof binds to CTLA4. The heavy chain constant region may be an IgG1, IgG2, or IgG4 heavy chain constant region, e.g., human IgG4 heavy chain constant region having the amino acid sequence set forth in e.g., SEQ ID NO.:78. The heavy chain constant region, such as the Fc fragment, may be engineered to have reduced or enhanced FcR binding affinity. The light chain constant region may be kappa constant region, e.g., human kappa constant region having the amino acid sequences set forth in e.g., SEQ ID NO.: 79. The amino acid sequences of SEQ ID NOs: 78 and 79 may be encoded by the nucleotide sequences of SEQ ID NOs: 92 and 93, respectively.

The antibody of the present disclosure in certain embodiments may comprise or consist of two heavy chains and two light chains, wherein each heavy chain may comprise the heavy chain constant region, heavy chain variable region or CDR sequences mentioned above, and each light chain may comprise the light chain constant region, light chain variable region or CDR sequences mentioned above, wherein the antibody binds to CTLA4. The antibody or antigen-binding portion thereof of the disclosure can be a full-length antibody, for example, of an IgG1, IgG2 or IgG4 isotype. The antibody or the antigen-binding portion thereof of the present disclosure in other embodiments may be a single chain variable fragment (scFv) antibody, or an antibody fragment, such as a Fab or F(ab')$_2$ fragment.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, that may comprise an antibody, or an antigen-binding portion thereof, of the disclosure, linked to a therapeutic agent, such as a cytotoxin. In another aspect, the antibody or the antigen binding portion thereof of the present disclosure can be made into part of a chimeric antigen receptor (CAR). Also provided is an immune cell that may comprise the antigen chimeric receptor, such as a T cell and a NK cell. The antibody or the antigen binding portion thereof of the present disclosure can also be encoded by or used in conjunction with an oncolytic virus.

Nucleic acid molecules encoding the antibody, or the antigen-binding portion thereof, of the disclosure are also encompassed by the disclosure, as well as expression vectors that may comprise such nucleic acids and host cells that may comprise such expression vectors. A method for preparing the anti-CTLA4 antibody or the antigen-binding portion thereof of the disclosure using the host cell is also provided, that may comprise steps of (i) expressing the antibody in the host cell and (ii) isolating the antibody from the host cell or its cell culture.

Compositions that may comprise the antibody, or the antigen-binding portion thereof, the immunoconjugate, the bispecific molecule, the oncolytic virus, the CAR, the CAR-T cell, the nucleic acid molecule, the expression vector or the host cells of the disclosure, and a pharmaceutically acceptable carrier, are also provided. In certain embodiments, the pharmaceutical composition may further contain a therapeutic agent such as an anti-cancer agent.

In yet another aspect, the disclosure provides a method of modulating an immune response in a subject comprising administering to the subject a therapeutically effective amount of the antibody or antigen-binding portion thereof, of the disclosure, or alternatively a nucleic acid molecule capable of expressing the same in the subject, such that the immune response in the subject is modulated. Preferably, the antibody or antigen-binding portion thereof of the disclosure enhances, stimulates or increases the immune response in the subject.

In yet another aspect, the disclosure provides a method of inhibiting tumor growth in a subject in need thereof, comprising administering to a subject a therapeutically effective amount of the antibody or antigen-binding portion thereof, of the disclosure, or alternatively a nucleic acid molecule capable of expressing the same in the subject. In some embodiments, the method comprises administering a bispecific molecule, an immunoconjugate, a CAR-T cell, or an antibody-encoding or antibody-bearing oncolytic virus of the disclosure. The tumor may be a solid or a hematological tumor. In certain embodiments, the tumor is solid tumor, including, but not limited to, melanoma, colorectal cancer, hepatocellular carcinoma, pleural mesothelioma, lung cancer (e.g., non-small cell lung cancer), renal cell carcinoma, cervical cancer, angiosarcoma, malignant pleural mesothelioma, metastatic transitional (urothelial) tract cancer, ureter cancer, urethral cancer, urinary tract cancer, head and neck cancer, squamous cell carcinoma, transitional cell cancer (urothelial cell cancer), esophageal cancer, gastric cancer, gastroesophageal (GE) junction carcinomas, adenocarcinoma of the gastroesophageal junction, anal cancer, bile duct cancer (cholangiocarcinoma), dysgerminoma, endometrial cancer, fallopian tube cancer, germ cell tumors, myelodysplastic syndrome, neuroblastoma, non-hodgkin lymphoma, osteosarcoma, ovarian cancer, peritoneal cancer, prostate cancer, salivary gland cancer, sarcomas, triple-negative breast cancer (TNBC), and muscle-invasive bladder cancer. In some embodiments, at least one additional anti-cancer antibody can be administered with the antibody, or an antigen-binding portion thereof, of the disclosure, such as an anti-VISTA antibody, an anti-PD-1 antibody, an anti-PD-L1 antibody, an anti-LAG-3 antibody, an anti-TIM-3 antibody, an anti-STAT3 antibody, and/or an anti-ROR1 antibody. In yet another embodiment, an antibody, or an antigen-binding portion thereof, of the disclosure is administered with a cytokine (e.g., IL-2, IL-21, GM-CSF and/or IL-4), or a costimulatory antibody (e.g., an anti-CD137 and/or anti-GITR antibody). In another embodiment, an antibody, or an antigen-binding portion thereof, of the disclosure is administered with a chemotherapeutic agent, which may be a cytotoxic agent, such as epirubicin, oxaliplatin, and/or 5-fluorouracil (5-FU). The antibody or antigen-binding portion thereof of the present disclosure may be, for example, mouse, human, chimeric or humanized.

In another aspect, the disclosure provides a method of treating or alleviating an infectious disease in a subject in need thereof, comprising administering to a subject a therapeutically effective amount of the composition of the present disclosure. The infectious disease may be a disease caused by viral, bacterial, fungal or mycoplasma infection. In certain embodiments, the infectious disease is caused by chronic HIV infection or HHV-4 infection. In certain embodiments, the subject may be further administered with at least one anti-infective agent, such as an anti-viral agent, an anti-bacterial agent, an anti-fungal agent, or an anti-mycoplasma agent.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
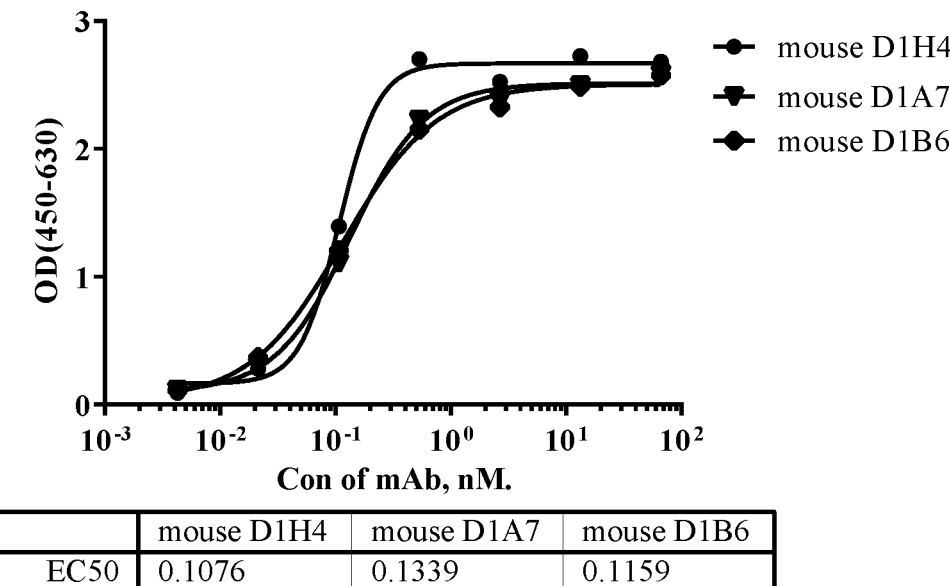
FIGS. 1A and 1B show the binding capacities of mouse antibodies D1H4, D1A7 and D1B6 (A), C1G4, D1H3, D1B8, D1D5, D2A4, C1D1 and D1G6 (B) to human CTLA4 in a capture ELISA.

To ensure that the present disclosure may be more readily understood, certain terms are first defined. Additional definitions are set forth throughout the detailed description.

The term "CTLA4" refers to cytotoxic T-lymphocyte-associated antigen 4. The term "CTLA4" comprises variants, isoforms, homologs, orthologs and paralogs. For example, an antibody specific for a human CTLA4 protein may, in certain cases, cross-react with a CTLA4 protein from a species other than human, such as monkey. In other embodiments, an antibody specific for a human CTLA4 protein may be completely specific for the human CTLA4 protein and exhibit no cross-reactivity to other species or of other types, or may cross-react with CTLA4 from certain other species but not all other species.

The term "human CTLA4" refers to a CTLA4 protein having an amino acid sequence from a human, such as the amino acid sequence of human CTLA4 having a Genbank accession number of NP_005205. The terms "monkey or rhesus CTLA4" and "mouse CTLA4" refer to monkey and mouse CTLA4 sequences, respectively, e.g. those with the amino acid sequences having Genbank Accession Nos. NP_001038204.1 and NP_033973.2, respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as used herein refers to an immunoglobulin molecule that recognizes and specifically binds a target, such as CTLA4, through at least one antigen-binding site wherein the antigen-binding site is usually within the variable region of the immunoglobulin molecule. As used herein, the term encompasses intact polyclonal antibodies, intact monoclonal antibodies, single-chain Fv (scFv) antibodies, heavy chain antibodies (HCAbs), light chain antibodies (LCAbs), multispecific antibodies, bispecific antibodies, monospecific antibodies, monovalent antibodies, fusion proteins comprising an antigen-binding site of an antibody, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes. Unless expressly indicated otherwise, the term "antibody" as used herein include "antigen-binding portion" of the intact antibodies. An IgG is a glycoprotein which may comprise two heavy (H) chains and two light (L) chains inter-connected by disulfide bonds. Each heavy chain may be comprised of a heavy chain variable region (abbreviated herein as $V_H$) and a heavy chain constant region. The heavy chain constant region may be comprised of three domains, $C_{H1}$, $C_{H2}$ and $C_{H3}$. Each light chain may be comprised of a light chain variable region (abbreviated herein as $V_L$) and a light chain constant region. The light chain constant region may be comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a CTLA4 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a CTLA4 protein is substantially free of antibodies that specifically bind antigens other than CTLA4 proteins). An isolated antibody that specifically binds a human CTLA4 protein may, however, have cross-reactivity to other antigens, such as CTLA4 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human CTLA4" is intended to refer to an antibody that binds to human CTLA4 protein (and possibly a CTLA4 protein from one or more non-human species) but does not substantially bind to non-CTLA4 proteins. Preferably, the antibody binds to human CTLA4 protein with "high affinity", namely with a $K_D$ of $5.0\times10^{-8}$ M or less, more preferably $1.0\times10^{-8}$ M or less, and more preferably $7.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $7.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The antibody, or the antigen-binding portion thereof, of the disclosure specifically binds to human CTLA4 with comparable, if not better, binding affinity/capacity as compared to previously described anti-CTLA4 antibodies, such as Ipilimumab.

The antibody, or the antigen-binding portion thereof, of the disclosure blocks CTLA4 binding to CD80/CD86, with comparable or higher activity, as compared to previously described anti-CTLA4 antibodies, such as Ipilimumab. The antibody, or the antigen-binding portion thereof, of the disclosure promotes T cell responses inhibited by CTLA4-CD80/CD86 binding.

Antibodies or antigen-binding portions thereof of the disclosure are mouse, chimeric or humanized.

The antibody or antigen-binding portion thereof of the disclosure is structurally and chemically characterized as described below and in the following Examples. The amino acid sequence ID numbers of the heavy/light chain variable regions of the antibodies are summarized in Table 1 below, some antibodies sharing the same $V_H$ or $V_L$. The heavy chain constant region for the antibodies may be human IgG4 heavy chain constant region having an amino acid sequence set forth in, e.g., SEQ ID NO: 78, and the light chain constant region for the antibodies may be human kappa constant region having an amino acid sequence set forth in, e.g., SEQ ID NO: 79. These antibodies may also contain mouse IgG4 heavy chain constant region, and mouse kappa constant region.

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences.

The $V_H$ and $V_L$ sequences (or CDR sequences) of other anti-CTLA4 antibodies which bind to human CTLA4 can be "mixed and matched" with the $V_H$ and $V_L$ sequences (or CDR sequences) of the anti-CTLA4 antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

TABLE 1

| Antibody ID | VH-CDR1 | VH-CDR2 | VH-CDR3 | VH | VL-CDR1 | VL-CDR2 | VL-CDR3 | VL |
|---|---|---|---|---|---|---|---|---|
| C1D1 | 1 | 2 | 3 | 54 | 4 | 5 | 6 | 56 |
| huC1D1-V1 | 1 | 2 | 3 | 55, X1 = A, X2 = V | 4 | 5 | 6 | 57, X1 = S, X2 = M, X3 = R, X4 = Y |
| huC1D1-V2 | 1 | 2 | 3 | 55, X1 = A, X2 = A | 4 | 5 | 6 | 57, X1 = S, X2 = M, X3 = R, X4 = Y |
| huC1D1-V3 | 1 | 2 | 3 | 55, X1 = G, X2 = V | 4 | 5 | 6 | 57, X1 = S, X2 = M, X3 = R, X4 = Y |
| huC1D1-V4 | 1 | 2 | 3 | 55, X1 = G, X2 = A | 4 | 5 | 6 | 57, X1 = S, X2 = M, X3 = R, X4 = Y |
| huC1D1-V5 | 1 | 2 | 3 | 55, X1 = A, X2 = V | 4 | 5 | 6 | 57, X1 = S, X2 = V, X3 = T, X4 = F |
| huC1D1-V6 | 1 | 2 | 3 | 55, X1 = A, X2 = A | 4 | 5 | 6 | 57, X1 = S, X2 = V, X3 = T, X4 = F |
| huC1D1-V7 | 1 | 2 | 3 | 55, X1 = G, X2 = V | 4 | 5 | 6 | 57, X1 = S, X2 = V, X3 = T, X4 = F |
| huC1D1-V8 | 1 | 2 | 3 | 55, X1 = G, X2 = A | 4 | 5 | 6 | 57, X1 = S, X2 = V, X3 = T, X4 = F |
| huC1D1-V9 | 1 | 2 | 3 | 55, X1 = A, X2 = V | 4 | 5 | 6 | 57, X1 = V, X2 = V, X3 = T, X4 = F |
| huC1D1-V10 | 1 | 2 | 3 | 55, X1 = A, X2 = A | 4 | 5 | 6 | 57, X1 = V, X2 = V, X3 = T, X4 = F |
| huC1D1-V11 | 1 | 2 | 3 | 55, X1 = G, X2 = V | 4 | 5 | 6 | 57, X1 = V, X2 = V, X3 = T, X4 = F |
| huC1D1-V12 | 1 | 2 | 3 | 55, X1 = G, X2 = A | 4 | 5 | 6 | 57, X1 = V, X2 = V, X3 = T, X4 = F |
| D1D5 | 7 | 8 | 9 | 58 | 10 | 11 | 12 | 60 |
| huD1D5-V1 | 7 | 8 | 9 | 59, X1 = P, X2 = A, X3 = D | 10 | 11 | 12 | 61, X1 = T, X2 = V, X3 = F |
| huD1D5-V2 | 7 | 8 | 9 | 59, X1 = L, X2 = A, X3 = N | 10 | 11 | 12 | 61, X1 = T, X2 = V, X3 = F |
| huD1D5-V3 | 7 | 8 | 9 | 59, X1 = L, X2 = A, X3 = D | 10 | 11 | 12 | 61, X1 = T, X2 = V, X3 = F |
| huD1D5-V4 | 7 | 8 | 9 | 59, X1 = L, X2 = S, X3 = N | 10 | 11 | 12 | 61, X1 = T, X2 = V, X3 = F |
| huD1D5-V5 | 7 | 8 | 9 | 59, X1 = P, X2 = A, X3 = D | 10 | 11 | 12 | 61, X1 = V, X2 = P, X3 = F |
| huD1D5-V6 | 7 | 8 | 9 | 59, X1 = L, X2 = A, X3 = N | 10 | 11 | 12 | 61, X1 = V, X2 = P, X3 = F |
| huD1D5-V7 | 7 | 8 | 9 | 59, X1 = L, X2 = A, X3 = D | 10 | 11 | 12 | 61, X1 = V, X2 = P, X3 = F |
| huD1D5-V8 | 7 | 8 | 9 | 59, X1 = L, X2 = S, X3 = N | 10 | 11 | 12 | 61. X1 = V, X2 = P, X3 = F |
| huD1D5-V9 | 7 | 8 | 9 | 59, X1 = P, X2 = A, X3 = D | 10 | 11 | 12 | 61, X1 = V, X2 = P, X3 = Y |
| huD1D5-V10 | 7 | 8 | 9 | 59, X1 = L, X2 = A, X3 = N | 10 | 11 | 12 | 61, X1 = V, X2 = P, X3 = Y |
| huD1D5-V11 | 7 | 8 | 9 | 59, X1 = L, X2 = A, X3 = D | 10 | 11 | 12 | 61, X1 = V, X2 = P, X3 = Y |
| huD1D5-V12 | 7 | 8 | 9 | 59, X1 = L, X2 = S, X3 = N | 10 | 11 | 12 | 61, X1 = V, X2 = P, X3 = Y |
| C1G4 | 1 | 2 | 13 | 62 | 14 | 5 | 15 | 63 |
| D1A7 | 16 | 17 | 18 | 64 | 19 | 20 | 21 | 65 |
| D1B6 | 22 | 23 | 24 | 66 | 25 | 26 | 27 | 67 |
| D1B8 | 28 | 29 | 30 | 68 | 31 | 32 | 33 | 69 |
| D1G6 | 22 | 34 | 24 | 70 | 35 | 26 | 27 | 71 |
| D1H3 | 36 | 37 | 38 | 72 | 39 | 40 | 41 | 73 |
| D1H4 | 42 | 43 | 44 | 74 | 45 | 46 | 47 | 75 |
| D2A4 | 48 | 49 | 50 | 76 | 51 | 52 | 53 | 77 |

Amino acid sequence ID numbers of heavy/light chain variable regions

Accordingly, in one embodiment, an antibody of the disclosure, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another anti-CTLA4 antibody, wherein the antibody specifically binds human CTLA4.

In another embodiment, an antibody of the disclosure, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-CTLA4 antibody, wherein the antibody specifically binds human CTLA4.

In yet another embodiment, the antibody, or antigen binding portion thereof, includes the heavy chain variable CDR2 region of anti-CTLA4 antibody combined with CDRs of other antibodies which bind human CTLA4, e.g., CDR1 and/or CDR3 from the heavy chain variable region, and/or CDR1, CDR2, and/or CDR3 from the light chain variable region of a different anti-CTLA4 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc.*

*Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8. *Scientific Review* 8 (2001); Igarashi et al., *J. Biochem* (Tokyo) 117:452-7 (1995); Bourgeois et al., *J. Virol* 72:807-10 (1998); Levi et al., *Proc. Nadi. Acad. Sci. U.S.A.* 90:4374-8 (1993); Polymenis and Stoller, *J. Immunol.* 152: 5218-5329 (1994) and Xu and Davis, *Immunity* 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-CTLA4 antibody and at least the CDR3 of the heavy and/or light chain variable region of the anti-CTLA4 antibody, or the CDR3 of the heavy and/or light chain variable region of another anti-CTLA4 antibody, wherein the antibody is capable of specifically binding to human CTLA4. These antibodies preferably (a) compete for binding with CTLA4; (b) retain the functional characteristics; (c) bind to the same epitope; and/or (d) have a similar binding affinity as the anti-CTLA4 antibody of the present disclosure. In yet another embodiment, the antibodies further may comprise the CDR2 of the light chain variable region of the anti-CTLA4 antibody, or the CDR2 of the light chain variable region of another anti-CTLA4 antibody, wherein the antibody is capable of specifically binding to human CTLA4. In another embodiment, the antibodies of the disclosure may include the CDR1 of the heavy and/or light chain variable region of the anti-CTLA4 antibody, or the CDR1 of the heavy and/or light chain variable region of another anti-CTLA4 antibody, wherein the antibody is capable of specifically binding to human CTLA4.

In another embodiment, an antibody of the disclosure comprises a heavy and/or light chain variable region sequences of CDR1, CDR2 and CDR3 sequences which differ from those of the anti-CTLA4 antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human CTLA4.

The antibody of the present disclosure possesses one or more of the following functional properties described above, such as high affinity binding to human CTLA4, and blocking activity on CTLA4-CD80/CD86 binding.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-CTLA4 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-CTLA4 monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha$ (1, 6)-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application 60/836, 998, filed on Aug. 11, 2006. The fucose residues of the antibody can be cleaved off using a fucosidase enzyme; e.g., the fucosidase $\alpha$-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-CTLA4 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-CTLA4 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the CTLA4 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol.

8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The antibody or antigen-binding portion thereof of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Also provided herein is an oncolytic virus that preferentially infects and kills cancer cells. Antibodies of the present disclosure can be used in conjunction with oncolytic viruses. Alternatively, oncolytic viruses encoding antibodies of the present disclosure can be introduced into human body.

Also provided herein are a chimeric antigen receptor (CAR) containing an anti-CTLA4 scFv, the anti-CTLA4 scFv comprising CDRs and heavy/light chain variable regions described herein.

The anti-CTLA4 CAR may comprise (a) an extracellular antigen binding domain comprising an anti-CTLA4 scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, comprising the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

In another aspect, the present disclosure provides a pharmaceutical composition which may comprise one or more antibodies or antigen-binding portions thereof, the bispecifics, CAR-T cells, oncolytic viruses, immunoconjugates, nucleic acid molecules, expression vectors, or host cells of the present disclosure formulated together with a pharmaceutically acceptable carrier. The antibodies or antigen-binding portion thereof, the bispecifics, CAR-T cells, oncolytic viruses, immunoconjugates, nucleic acid molecules, expression vectors, or host cells can be dosed separately when the composition contains more than one antibody (or antigen-binding portion thereof, the bispecifics, CAR-T cells, oncolytic viruses, immunoconjugates, nucleic acid molecules, expression vectors, or host cells). The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg.

A "therapeutically effective dosage" of an anti-CTLA4 antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374, 548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The composition of the present disclosure have numerous in vitro and in vivo utilities involving, for example, treatment of cancers and infectious diseases. The compositions can be administered to human subjects, e.g., in vivo, to inhibit tumor growth, or to reduce or eliminate pathogens.

In another aspect, the disclosure provides a method of treating or alleviating an infectious disease in a subject in need thereof, comprising administering to a subject a therapeutically effective amount of the composition of the present disclosure. The infectious disease may be a disease caused by viral, bacterial, fungal or mycoplasma infection. In certain embodiments, the infectious disease is caused by chronic HIV or HHV-4 infection. In certain embodiments, the subject may be further administered with at least one an anti-infective agent, such as an anti-viral agent, an anti-bacterial agent, an anti-fungal agent, or an anti-mycoplasma agent.

Given the ability of anti-CTLA4 antibodies or antigen-binding portions of the disclosure to reverse CTLA4-CD80/CD86 mediated T cell suppression and promote T cell responses, the disclosure provides methods for inhibiting growth of tumor cells in a subject comprising administering to the subject the composition of the disclosure such that growth of the tumor is inhibited in the subject. Non-limiting examples of tumors that can be treated by the composition of the disclosure include, but not limited to, melanoma, colorectal cancer, hepatocellular carcinoma, pleural mesothelioma, lung cancer (e.g., non-small cell lung cancer), renal cell carcinoma, cervical cancer, angiosarcoma, and muscle-invasive bladder cancer. Additionally, refractory or recurrent malignancies whose growth may be inhibited using the antibodies of the disclosure.

In another aspect, the disclosure provides methods of combination therapy in which the anti-CTLA4 antibodies, or antigen-binding portion thereof, or the bispecifics, CAR-T cells, oncolytic viruses, immunoconjugates of the present disclosure are co-administered with one or more additional antibodies that are effective in inhibiting tumor growth in a subject. In one embodiment, the disclosure provides a method for inhibiting tumor growth in a subject comprising administering to the subject an anti-CTLA4 antibody (or antigen-binding portion thereof, or the CAR-T cell, oncolytic virus, immunoconjugate) and one or more additional antibodies, such as an anti-VISTA antibody, an anti-LAG-3 antibody, an anti-PD-L1 antibody, and/or an anti-PD-1 antibody. In certain embodiments, the subject is human.

The CTLA4 signaling blockade can also be further combined with standard cancer treatments. For example, CTLA4 signaling blockade can be combined with LAG-3 and/or PD-1 blockade and also chemotherapeutic regimes. For example, a chemotherapeutic agent can be administered with the anti-CTLA4 antibodies, which may be a cytotoxic agent. For example, epirubicin, oxaliplatin, and 5-FU are administered to patients receiving anti-CTLA4 therapy.

Optionally, the combination of anti-CTLA4 and one or more additional antibodies (e.g., anti-TIM-3 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

Other therapies that may be combined with anti-CTLA4 therapy includes, but not limited to, interleukin-2 (IL-2) administration, radiation, surgery, or hormone deprivation.

In another aspect, the disclosure provides methods of combination therapy in which the anti CTLA4 antibodies, or antigen-binding portion thereof of the present disclosure are co-administered with one or more additional agents effective in reduce or eliminate pathogens. In one embodiment, the disclosure provides a method for treating or alleviating an infectious disease in a subject comprising administering to the subject an anti-CTLA4 antibody or antigen-binding portion thereof and one or more additional agents against pathogens such as an anti-viral agent, an anti-bacterial agent, an anti-fungal agent, or an anti-mycoplasma agent. In certain embodiments, the subject is human.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-CTLA4 Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. Recombinant human CTLA4 protein with human IgG1 Fc tag at the C-terminus (Acro biosystems, Cat #CT4-H5255) was used as the immunogen. Human CTLA4-his protein (Acro biosystems, Cat #CT4-H5229) was used for determining anti-sera titer and for screening hybridomas secreting antigen-specific antibodies. Immunizing dosages contained 25 µg human CTLA4-Fc protein/mouse/injection for both primary and boost immunizations. To increase immune response, the complete Freud's adjuvant and incomplete Freud's adjuvant (Sigma, St. Louis, Mo., USA) were used respectively for primary and boost immunizations. Briefly, adjuvant-antigen mixture was prepared by first gently mixing the adjuvant in a vial using a vortex. The desired amount of adjuvant was transferred to an autoclaved 1.5 mL micro-centrifuge tube. The antigen was prepared in PBS or saline with concentration ranging from 0.25 to 0.5 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into the proper syringe for animal injection. A total of 25 µg of antigen was injected in a volume of 100-200 µl. Each animal was immunized, and then boosted for 4 to 5 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256: 495-497(1975). Fused "hybrid cells" were subsequently dispensed into 96-well plates in DMEM/20% FCS/HAT media. Surviving hybridoma colonies were observed under the microscope seven to ten days post fusion. After two weeks, the supernatant from each well was subject to indirect ELISA using recombinant human CTLA4-his protein. Positive hybridomas secreting antibodies that bound to human CTLA4-his protein were then selected and transferred to 24-well plates. Hybridomas were further tested for the activities of blocking human CTLA4-Fc protein binding to cell surface CD80/CD86 by flow cytometry (FACS). Hybridoma clones producing antibodies that showed high specific human CTLA4 binding and CTLA4-Daudi cell blocking activities were subcloned by limiting dilution to ensure the clonality of the cell line, and then monoclonal antibodies were purified. Briefly, Protein A sepharose columns (from bestchrom (Shanghai) Biosciences, Cat #AA0273) were washed using PBS buffer in 5 to 10 column volumes. Cell supernatants of hybridoma monoclones were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C. Subsequently, the in vitro functional activities of purified monoclonal antibodies were characterized as follows.

Example 2 Binding Affinity Determination of Mouse Anti-CTLA4 Monoclonal Antibodies Using BIACORE Surface Plasmon Resonance The purified anti-CTLA4 mouse monoclonal antibodies (mAbs) generated in Example 1 were characterized for binding affinity and binding kinetics by Biacore T200 system (GE healthcare, Pittsburgh, PA, USA).

Briefly, goat anti-mouse IgG (GE healthcare, Cat #BR100838, Mouse Antibody Capture Kit) was covalently linked to a CM5 chip (carboxy methyl dextran coated chip from GE healthcare #BR100530) via primary amines, using a standard amine coupling kit provided by Biacore (GE healthcare, Pittsburgh, PA, USA), and a Protein G chip (GE healthcare, Cat #29-1793-15) was used for the benchmark's affinity determination. Un-reacted moieties on the biosensor surface were blocked with ethanolamine. Then, purified anti-CTLA4 antibodies of the disclosure and a CTLA4 benchmark (Bristol-Myers Squibb Co, Cat #NDC: 0003-2327-11, also referred to as Yervoy® or BM), at the concentration of 10 µg/ml, were flowed onto the chip at a flow rate of 10 µL/min. Then, serially diluted recombinant human CTLA4-his (Acro biosystems, Cat #CT4-H5229, starting at 80 nM with a 2-fold serial dilution) or cynomolgus monkey CTLA4-his protein (Acro biosystems, Cat #CT4-C5227, starting at 80 nM with a 2-fold serial dilution) in HBS-EP® buffer (provided by Biacore) was flowed onto the chip at a flow rate of 30 µL/min. The antigen-antibody association kinetics was followed for 2 minutes and the dissociation kinetics was followed for 10 minutes. The association and dissociation curves were fit to a 1:1 Langmuir binding model using BIAcore evaluation software. The $K_D$, $K_a$ and $K_d$ values were determined and summarized in Table 2 below.

TABLE 2

| | Kinetics on Biacore | | | | | |
|---|---|---|---|---|---|---|
| Mouse | Human CTLA4-his | | | Cynomolgus CTLA4-his | | |
| mAb ID# | $K_a$ $(M^{-1}s^{-1})$ | $K_d$ $(s^{-1})$ | $K_D$ (M) | $K_a$ $(M^{-1}s^{-1})$ | $K_d$ $(s^{-1})$ | $K_D$ (M) |
| D2A4 | 6.71E+05 | 0.001525 | 2.24E−09 | 3.40E+05 | 7.60E−04 | 2.24E−09 |
| C1D1 | 2.51E+05 | 1.00E−04 | 3.99E−10 | 4.78E+05 | 8.76E−05 | 1.83E−10 |
| C1G4 | 2.90E+05 | 5.13E−04 | 1.77E−09 | 4.51E+05 | 7.70E−04 | 1.71E−09 |
| D1B6 | 6.54E+04 | 4.87E−04 | 7.45E−09 | 1.91E+05 | 7.87E−04 | 4.12E−09 |
| D1D5 | 1.46E+05 | 2.76E−04 | 1.89E−09 | 1.01E+05 | 4.70E−04 | 4.67E−09 |
| D1H3 | 2.24E+05 | 9.31E−04 | 4.15E−09 | 2.90E+05 | 6.01E−04 | 2.07E−09 |
| D1H4 | 3.46E+05 | 3.21E−04 | 9.25E−10 | 5.80E+05 | 4.22E−04 | 7.27E−10 |
| DIG6 | 7.67E+04 | 6.95E−04 | 9.06E−09 | 3.38E+05 | 6.62E−04 | 1.96E−09 |
| D1B8 | 2.21E+05 | 4.95E−04 | 2.24E−09 | 4.51E+05 | 5.32E−04 | 1.18E−09 |
| D1A7 | 2.49E+05 | 6.02E−04 | 2.41E−09 | 8.29E+05 | 0.001374 | 1.66E−09 |
| Yervoy ® | 1.50E+05 | 8.78E−04 | 8.38E−09 | 1.62E+05 | 4.80E−04 | 2.97E−09 |

All the mouse antibodies of the disclosure specifically bound to human and cynomolgus monkey CTLA4 with comparable or higher binding affinities compared to the benchmark. The antibodies C1D1, C1G4, D1D5, D1H4, D1B8 and D1A7 showed the highest binding affinities to human CTLA4.

Example 3 CTLA4 Binding Activity of Mouse Anti-CTLA-4 Antibodies

The binding activities of mouse anti-CTLA4 antibodies of the disclosure to CTLA4 were determined by Capture ELISA.

Briefly, 96-well plates were coated with 2 µg/ml Affi-niPure Goat Anti-Mouse IgG F(ab')$_2$ fragment specific (Jackson Immuno Research, Cat #115-005-072) in PBS, 100 µl/well, and incubated overnight at 4° C. Plates were washed once with wash buffer (PBS+0.05% v/v Tween-20, PBST) and then blocked with 200 µl/well blocking buffer (PBST with 5% w/v non-fatty milk) for 2 hours at 37° C. Plates were washed 4 times and incubated with 100 µl/well serially diluted mouse anti-CTLA4 antibodies of the disclosure, the benchmark, or a negative control hIgG (human immuno-globulin (pH4) for intravenous injection, Hualan Biological Engineering Inc.) (5-fold dilution in PBST with 2.5% w/v non-fatty milk, starting at 10000 ng/ml) for 40 minutes at 37° C., and then washed 4 times again. Plates containing captured anti-CTLA4 antibodies were added with 100 µl/well biotin labeled human CTLA4-Fc protein (Acro bio-systems, Cat #CT4-H5255, 26 ng/ml in PBST with 2.5% w/v non-fatty milk) and incubated for 40 minutes at 37° C., washed 4 times, and incubated with streptavidin conjugated HRP (1:10000 dilution in PBST, Jackson Immuno Research, Cat #016-030-084, 100 µl/well) for 40 minutes at 37° C. After a final wash, plates were incubated with 100 µl/well substrate TMB (Innoreagents, Cat #TMB-S-002). The reaction was stopped in 15 minutes at room temperature with 50 µl/well 1M H$_2$SO$_4$, and the absorbance of the each well was read on a microplate reader using dual wavelength mode with 450 nm for TMB and 630 nm as the reference wave-length, then the OD (450-630) values were plotted against antibody concentration. Data was analyzed using Graphpad Prism software and EC$_{50}$ values were reported. The results were shown in FIGS. 1A and 1B.

Figure 1B:
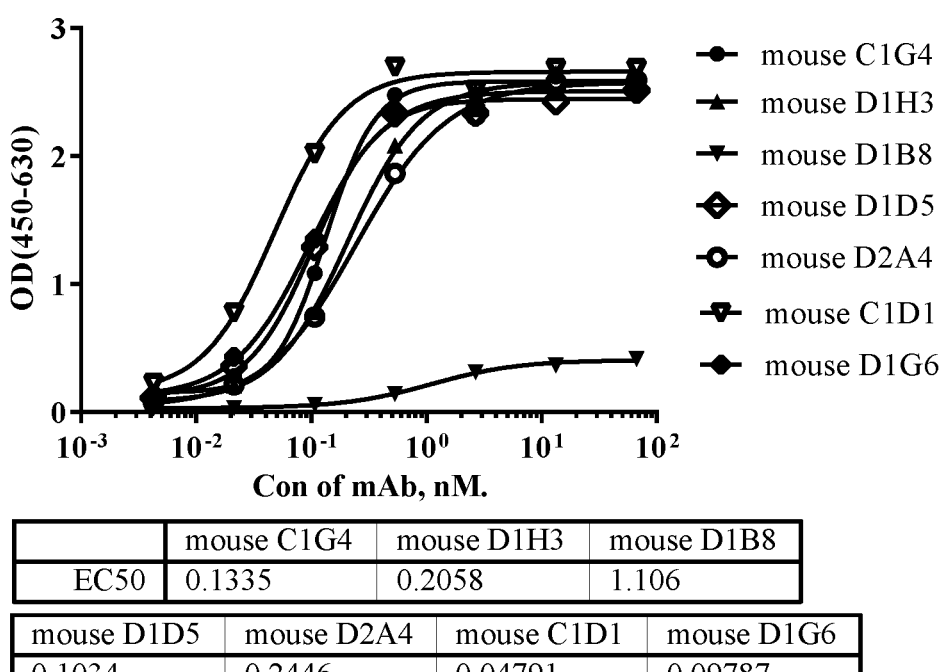

It can be seen from FIGS. 1A-1B that all mouse anti-CTLA4 antibodies of the disclosure, except DIB8, specifi-cally bound human CTLA4 with high binding capacities.

Example 4 Benchmark Blocking Activity and CTLA4-CD80/86 Blocking Activity of Mouse Anti-CTLA-4 Antibodies

4.1 Benchmark Blocking ELISA

The abilities of the anti-CTLA4 antibodies of the present disclosure to block Benchmark-human CTLA4 binding was measured in a competitive ELISA assay. Briefly, the bench-mark was coated on 96-well micro plates at 1.0 µg/mL in PBS, 100 µl/well, and incubated for 2 hours at 37° C. Plates were washed once with wash buffer, blocked with 200 µl PBST with 5% w/v non-fatty milk, incubated for 2 hours at 37° C., and washed 4 times.

The anti-CTLA4 antibodies of the disclosure or controls were diluted with biotin labeled human CTLA4-Fc (Acro biosystems, Cat #CT4-H5255, 65 ng/ml in PBST with 2.5% w/v non-fatty milk), 3-fold serial dilution starting at 133.33 nM, and incubated at room temperature for 40 minutes, and then the antibody/human CTLA4-Fc mixtures were added to the benchmark coated plates, 100 µl/well. After incubation at 37° C. for 40 minutes, plates were washed 4 times again using wash buffer. Then the plates were added and incubated with 100 µl/well streptavidin conjugated HRP (1:10000 dilution in PBST, Jackson Immuno Research, Cat #016-030-084, 100 µl/well) for 40 minutes at 37° C. Plates were finally washed using wash buffer. Finally, TMB was added and the reaction was stopped using 1M H$_2$SO$_4$, and the absorbance of the each well was read on a microplate reader using dual wavelength mode with 450 nm for TMB and 630 nm as the reference wavelength, then the OD (450-630) values were plotted against antibody concentration. Data was analyzed using Graphpad Prism software and IC$_{50}$ values were reported.

4.2 Cell Based Ligand Blocking FACS

The activities of the anti-CTLA4 antibodies of the dis-closure to block human CTLA4-Fc protein binding to cell surface CD80/CD86 was evaluated with Flow Cytometry (FACS), using a cell line Daudi (ATCC® CCL-213) expressing cell-surface human CD80 and human CD86.

The anti-CTLA4 antibodies of the disclosure, the bench-mark or negative control hIgG (human immunoglobulin (pH4) for intravenous injection, Hualan Biological Engi-neering Inc.) were diluted with human CTLA4-Fc solution (Acro biosystems, Cat #CT4-H5255, 1 µg/mL in FACS buffer), 2-fold serial dilution starting at 33.33 nM, and incubated at room temperature for 30 minutes. Daudi cells were harvested from cell culture flasks at the log phase, washed twice and re-suspended in PBS containing 2% v/v Fetal Bovine Serum (FACS buffer). Daudi cells, $1\times10^5$ cells per well, were incubated in 96 well-plates with 100 μl/well the antibody/CTLA4-Fc mixtures for 40 minutes at 4° C. The plates were washed twice with FACS buffer, and then added and incubated for 40 minutes at 4° C. in dark with 100 μl/well R-Phycoerythrin AffiniPure Goat Anti-Human IgG, Fcγ fragment specific (1:1000 dilution in FACS buffer, Jackson Immunoresearch, Cat #109-115-098). Cells were washed twice and re-suspended in FACS buffer. Fluorescence was measured using a Becton Dickinson FACS Canto II-HTS equipment. Data was analyzed using Graphpad Prism software and $IC_{50}$ values were reported.

The results were shown in FIGS. 2A-2B and 3A-3B.

Figure 2A:
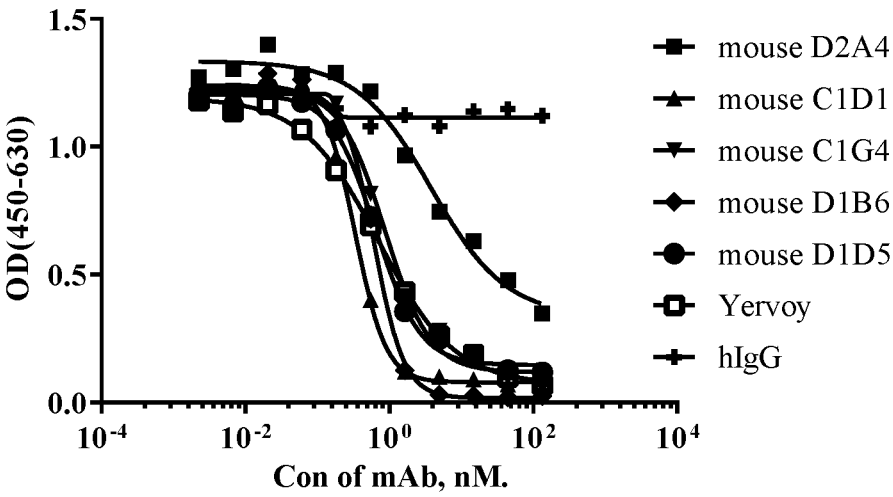
FIGS. 2A and 2B show the abilities of mouse antibodies D2A4, C1D1, C1G4, D1B6 and D1D5 (A), D1H3, D1A7, D1G6, D1H4, and D1B8 (B) to block benchmark binding to human CTLA4 in a competitive ELISA.
Figure 2B:
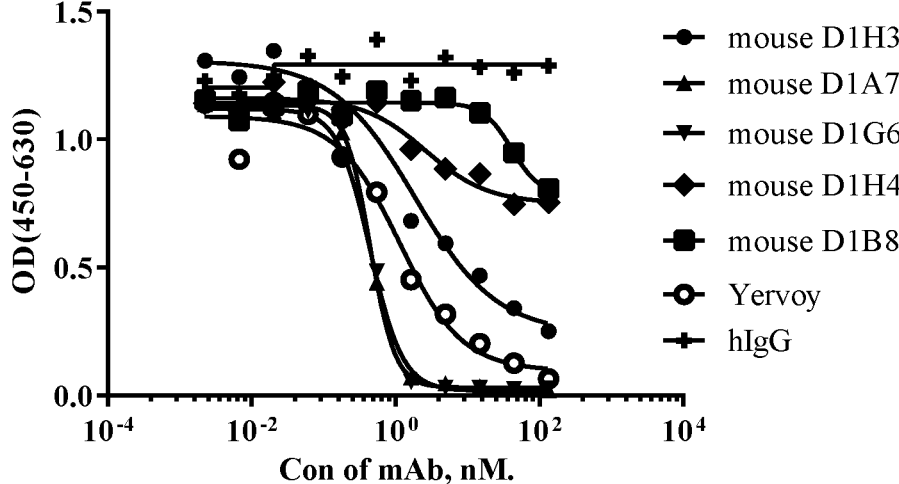

It can be seen from FIGS. 2A-2B that most antibodies of the disclosure were able to block human CTLA4-benchmark binding, suggesting that these antibodies of the disclosure bound to the same or similar epitopes as the benchmark did. The antibodies D2A4, D1B8 and D1H4 were unable to block human CTLA4 binding to benchmark, suggesting that D2A4, D1B8 and D1H4 might bind to different epitopes.

Figure 3A:
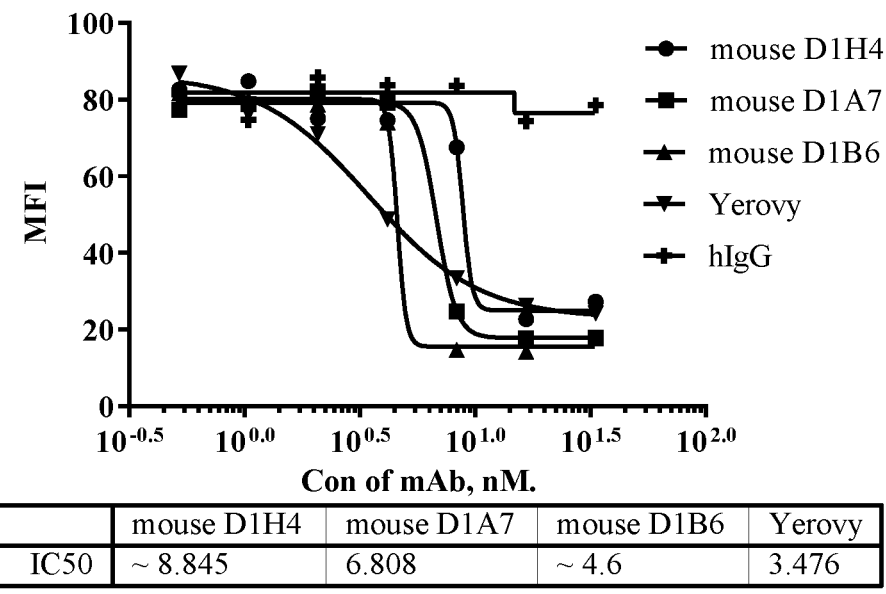
FIGS. 3A and 3B show the abilities of mouse antibodies D1H4, D1A7 and D1B6 (A), C1G4, D1H3, D1B8, D1D5, D2A4, C1D1 and D1G6 (B) to block CTLA4 binding to cell surface CD80/CD86 in a cell based blocking FACS assay.
Figure 3B:
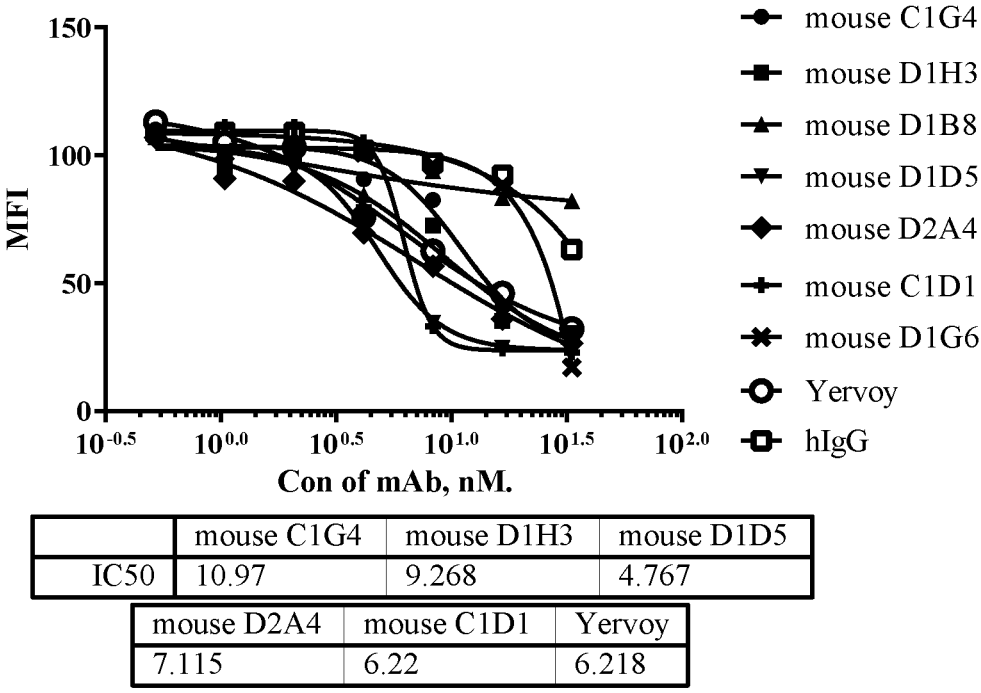

FIGS. 3A-3B showed that most antibodies of the disclosure were capable of blocking CTLA4 binding to cell surface CD80/CD86, with a comparable or higher activity than the benchmark.

Example 5 Cell Based Functional Assay of Mouse Anti-CTLA-4 Antibodies

The anti-CTLA4 antibodies of the disclosure were tested for their activities of promoting T cell response.

Briefly, $4\times10^4$ GS-J1 cells (immortalized human T lymphocytes expressing CD28, GenScript, Cat #M00611) in 20 μL RPMI1640 medium (Gibco, Cat #11875-093) supplemented with 10% FBS (Gibco, Cat #10099-141) and 5 μg/mL PHA (Sigma, Cat #L1668-5M) were plated into each well of 384 well-plates (Corning, Cat #3707). Human CTLA4-Fc (Acro biosystems, Cat #CT4-H5255) was diluted to 8 μg/mL in RPMI1640 medium supplemented with 10% FBS, and 20 μL CTLA4-Fc was added to each well of the plates. Then, each well of the plates was added with $2\times10^4$ GS-C1/CD80 cells (immortalized antigen presenting cells expressing cell-surface CD80, GenScript, Cat #M00614) in 20 μL RPMI1640 medium supplemented with 10% FBS, followed by 20 μL serially diluted anti-CTLA4 antibodies (starting at 333.33 nM with a 2.5-fold serial dilution) in RPMI1640 medium supplemented with 10% FBS. The plates were put in a 5% $CO_2$ incubator at 37'C for 24 h. The plates were centrifuged and the IL2 level in the supernatant was measured in 384-well low volume microplates (Greiner, Cat #784075) using human IL-2 HTRF kit (Cisbio, Cat #62HIL02PEG). Data was analyzed using Graphpad Prism software and $EC_{50}$ values were reported.

Figure 4:
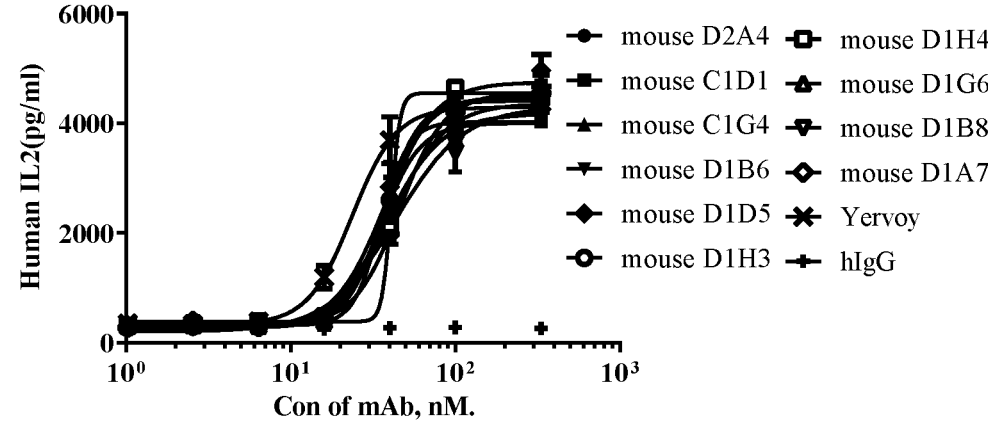
FIG. 4 shows that mouse antibodies D2A4, C1D1, C1G4, D1B6, D1D5, D1H3, D1H4, D1G6, D1B8 and D1A7 blocked CTLA4-CD80 binding and induced IL-2 release in a cell based functional assay.
Figure 5A:
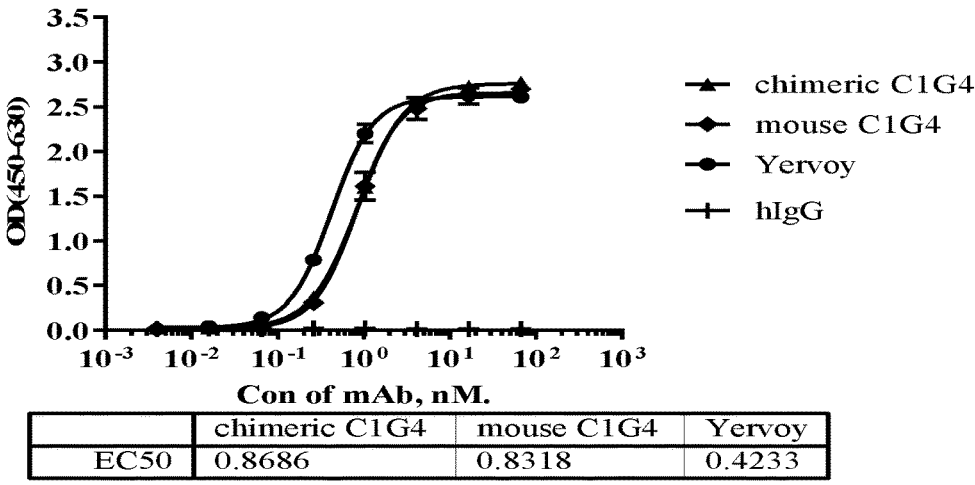
FIGS. 5A to 5E show the binding capacities of chimeric antibodies C1G4 (A), D1B6 (B), C1D1(C), D1D5 (D) and D1B8 (E) to human CTLA4 in a capture ELISA.
Figure 5B:
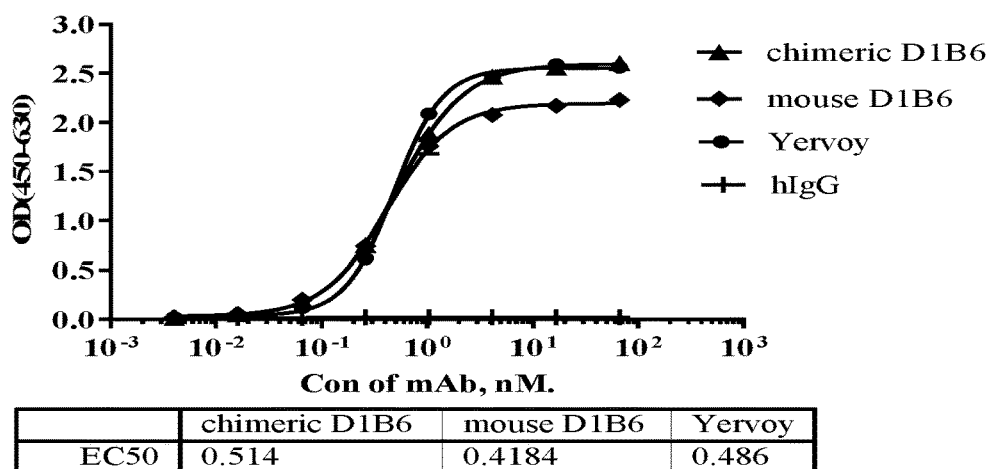
Figure 5C:
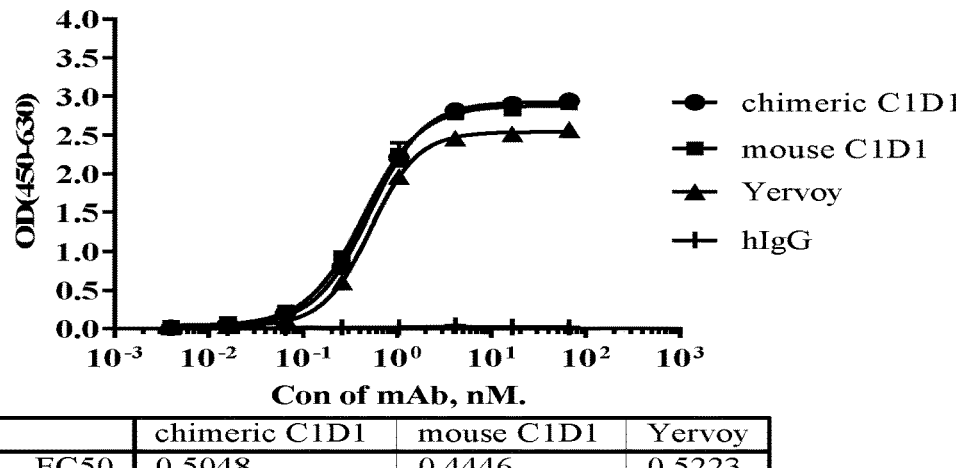
Figure 5D:
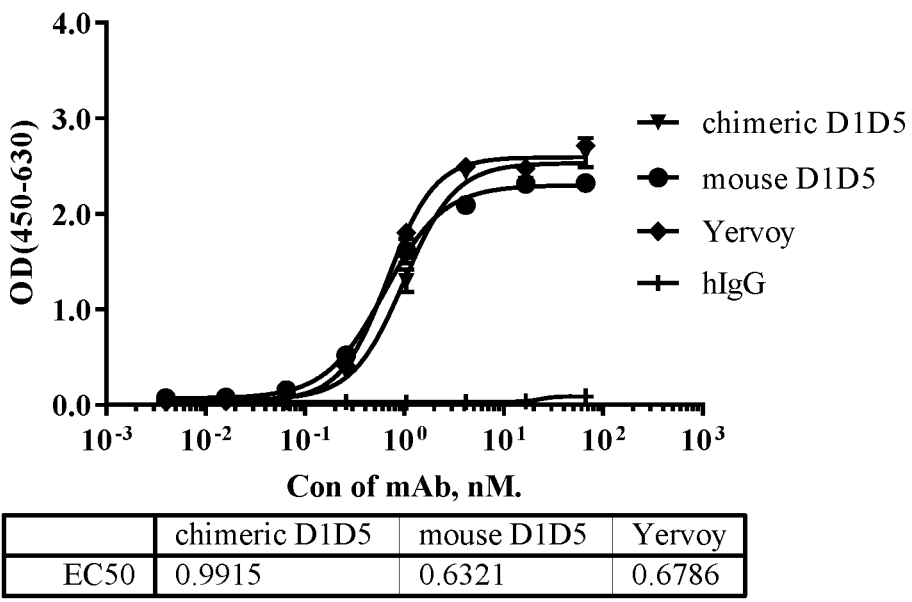
Figure 5E:
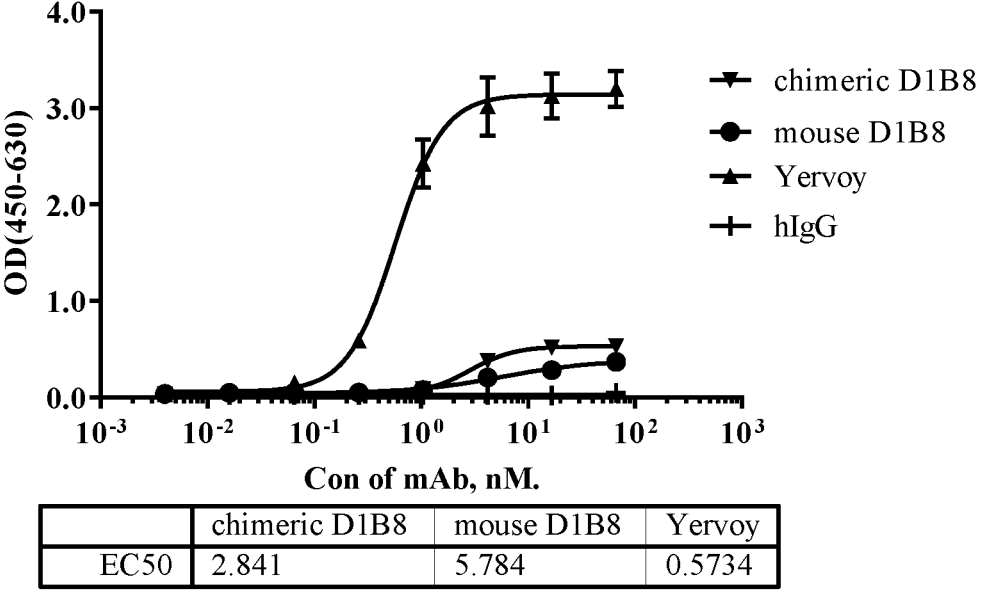
Figure 6A:
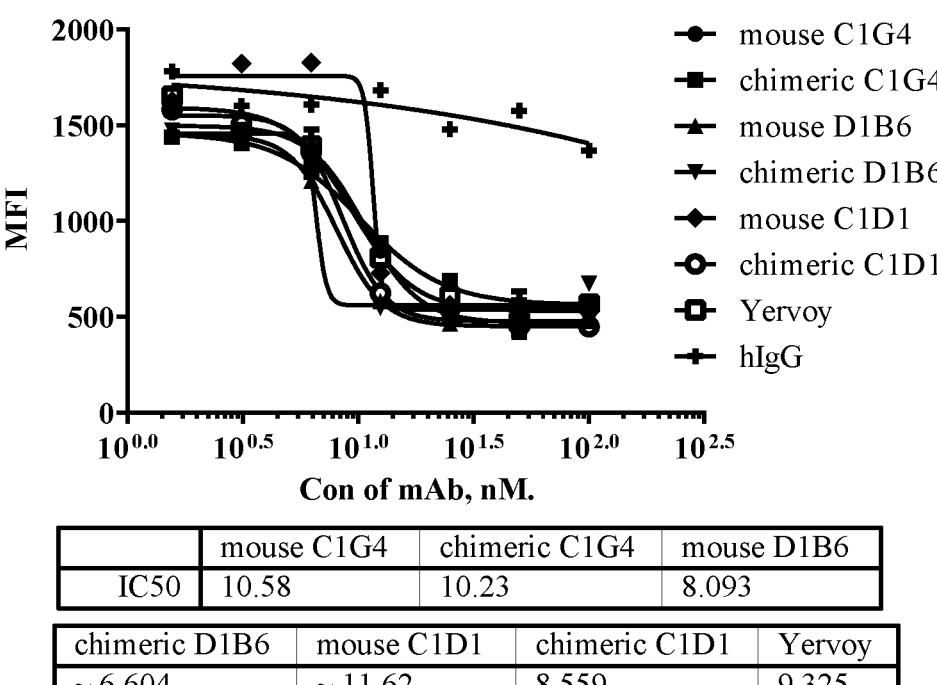
FIGS. 6A and 6B show the abilities of chimeric antibodies C1G4, D1B6 and C1D1 (A), D1D5 and D1B8 (B) to block CTLA4 binding to cell surface CD80/CD86 in a cell based blocking FACS assay.
Figure 6B:
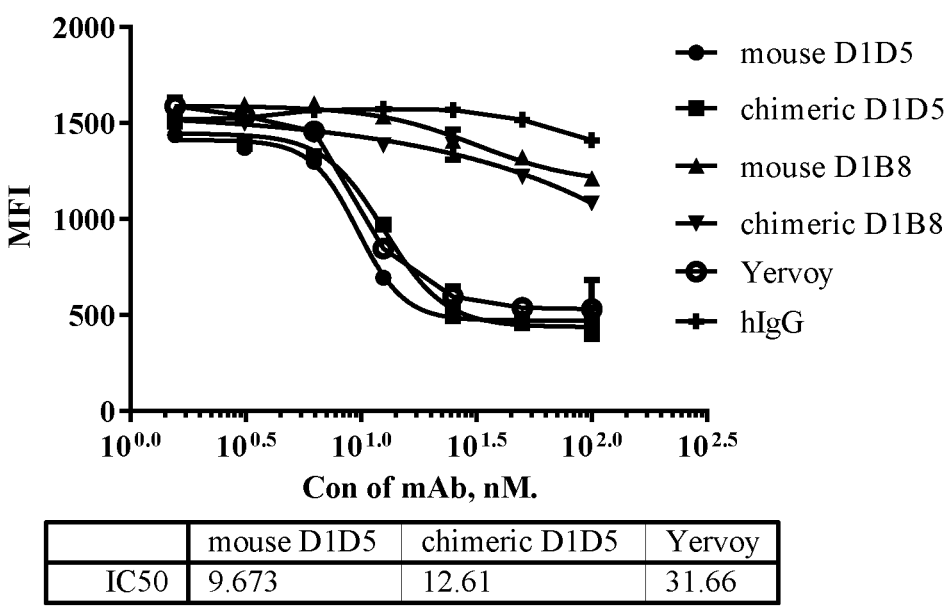
Figure 7A:
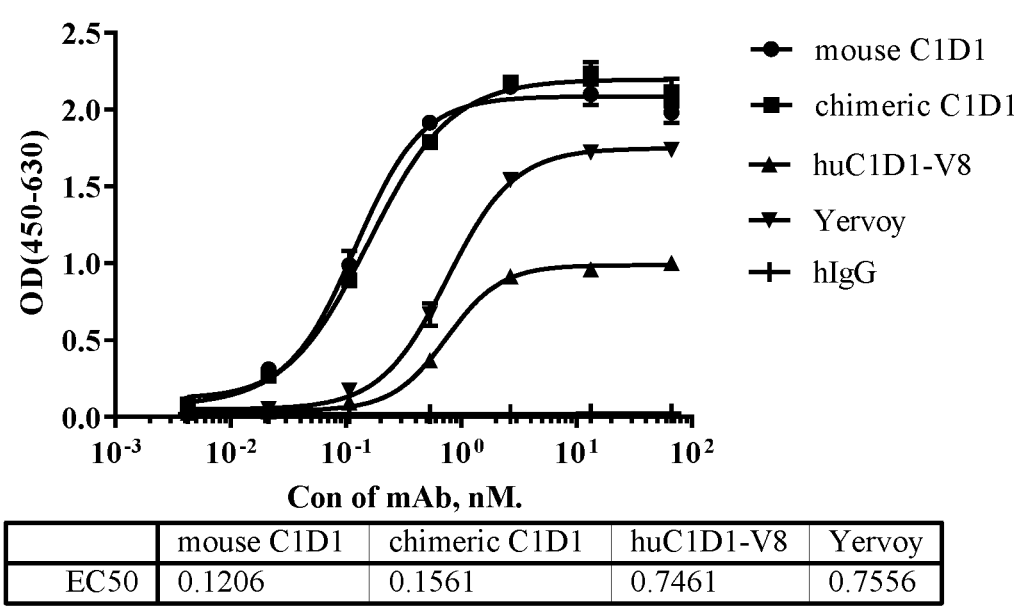
FIGS. 7A and 7B show the binding capacities of humanized antibodies huC1D1-V8 (A) and huD1D5-V9 (B) to human CTLA4 in a capture ELISA.
Figure 7B:
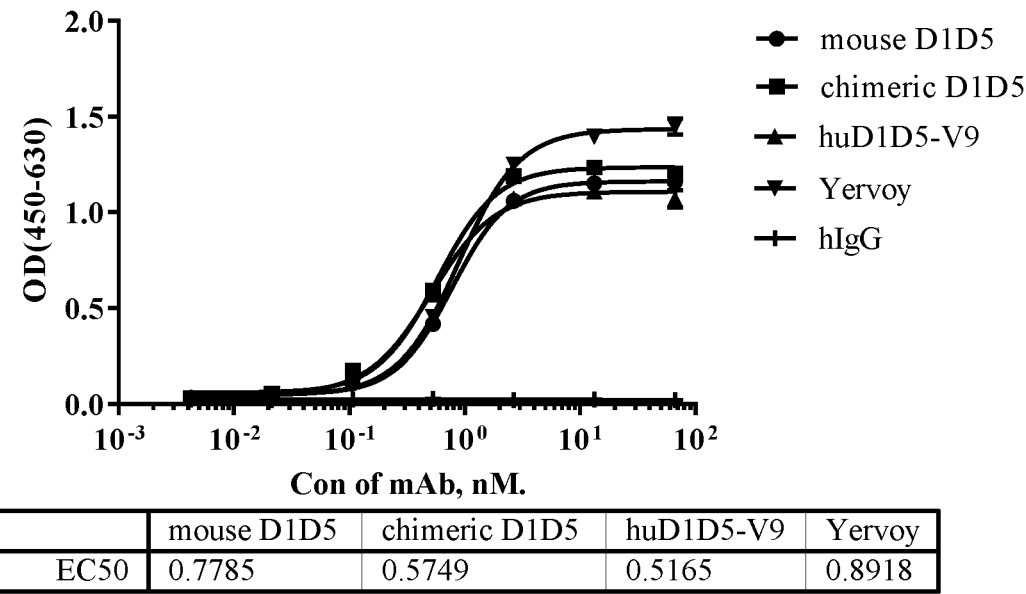

The assay results were shown in FIG. 4.

It can be seen that all the antibodies of the disclosure were capable of promoting T cell response, with a bit higher $EC_{50}$ but similar maximum IL2 release level compared to the benchmark.

Example 6 Generation and Characterization of Chimeric Antibodies

The heavy and light chain variable domains of the anti-CTLA4 mouse mAbs were sequenced, and the sequence ID numbers were summarized in Table 1.

The heavy and light chain variable domains of the anti-CTLA4 mouse mAbs CIG4, D1B6, C1D1, D1D5, and D1B8 were cloned in frame to human IgG4 heavy-chain (SEQ ID NO.: 78) and human kappa light-chain constant regions (SEQ ID NO.: 79), respectively, wherein the C terminus of variable region was linked to the N terminus of the respective constant region.

The vectors each containing a nucleotide encoding a heavy chain variable region linked to human IgG4 heavy-chain constant region (SEQ ID NO: 78), and the vectors each containing a nucleotide encoding a light chain variable region linked to human kappa light-chain constant region (SEQ ID NO: 79) were transiently transfected into 200 ml of 293F suspension cell cultures in a ratio of 1.1:1 light to heavy chain construct, with 1 mg/mL PEI.

Cell supernatants containing chimeric antibodies were harvested after six days in shaking flasks, and then chimeric antibodies were purified from cell supernatants as described above. The purified chimeric antibodies were tested in capture ELISA, Octet affinity test and cell based ligand blocking FACS following the protocols in the foregoing Examples with or without modifications and protocols described below.

The purified anti-CTLA4 chimeric antibodies were characterized for binding affinity and binding kinetics by Octet system (Fortebio, Octet RED 96). Briefly, AHC biosensors (anti-human IgG Fc capture, from ForteBio) were presoaked with 10 mM glycine (pH 1.5) for 3 seconds, and then dipped in a well with running buffer (0.5% w/v BSA in PBST) for 3 seconds, the soaking and dipping steps were repeated for three times. Then, the sensors were dipped in a well with the chimeric anti-CTLA4 antibodies in HBS-EP$^+$ at 5 μg/ml or the benchmark in HBS-EP$^+$ at 5 μg/ml for 100 seconds, and then immersed in a well with running buffer for 5 min. A new baseline was run for 180 seconds in another well with running buffer. Then the sensors were dipped in a well with serially diluted human CTLA4-his proteins (Acro biosystems, Cat #CT4-H5229, starting at 80 nM with a two-fold serial dilution) in running buffer for 100 seconds, and then immersed in a baseline well for 10 min. Finally, sensors were presoaked with 10 mM glycine (pH 1.5) for 3 seconds, and then were dipped in a well with running buffer for 3 seconds, the soaking and dipping steps repeated for three times. The association and dissociation curves were fit to a 1:1 Langmuir binding model using ForteBio Data Analysis 8.1. The $K_a$, $K_d$ and $K_D$ values were determined and summarized in Table 3 below.

For the capture ELISA, AffiniPure Goat Anti-Human IgG, Fcγ fragment specific (Jackson Immuno Research, Cat #109-005-008) was used instead of AffiniPure Goat Anti-Mouse IgG, F(ab')$_2$ fragment specific, 100 μl/well.

The results were shown in Table 3 and FIGS. 5A-5E and 6A-6B.

As shown in Table 3, the chimeric C1G4, C1D1 and D1D5 anti-CTLA4 antibodies specifically bound to human CTLA4 with higher binding affinities than the benchmark.

As shown in FIGS. 5A-5E and 6A-6B, the chimeric anti-CTLA4 antibodies had similar binding capacities and ligand blocking activities to their parental mouse mAbs. The chimeric D1B6, C1D1 and DID5 anti-CTLA4 antibodies had a bit better blocking activities than Yervoy® in the cell-based ligand blocking FACS.

TABLE 3

Binding affinities of Chimeric Antibodies to human CTLA4

| | Kinetics on Biacore Human CTLA4-his | | |
|---|---|---|---|
| Clone ID# | $K_a$ $(M^{-1}s^{-1})$ | $K_d$ $(M^{-1}s^{-1})$ | $K_D$ $(M^{-1}s^{-1})$ |
| C1G4 | 6.76E+05 | 6.79E−04 | 1.00E−09 |
| D1B6 | 5.14E+03 | 7.60E−04 | 1.48E−07 |
| C1D1 | 8.84E+05 | 2.96E−04 | 3.35E−10 |
| D1D5 | 3.12E+05 | 1.66E−03 | 5.32E−09 |
| Yervoy ® | 6.21E+04 | 1.73E−03 | 2.79E−08 |

*D1B8 not tested.

Example 7 Humanization of Anti-CTLA4 Mouse Monoclonal Antibodies C1D1 and D1D5

Mouse anti-CTLA4 antibodies C1D1 and D1D5 were selected for humanization and further investigations. Humanization of the mouse antibodies were conducted using the well-established CDR-grafting method as described in detail below.

To select acceptor frameworks for humanization of mouse antibodies C1D1 and D1D5, the light and heavy chain variable region sequences of each mouse antibody were blasted against the human immunoglobulin gene database. The human germlines with the highest homology were selected as the acceptor frameworks for humanization. The mouse antibody heavy/light chain variable region CDRs were inserted into the selected frameworks, and the residue(s) in the frameworks was/were further back mutated to obtain more candidate heavy chain/light chain variable regions. A total of 12 humanized C1D1 antibodies, namely huC1D1-V1 to huC1D1-V12, and 12 humanized D1D5 antibodies, namely huD1D5-V1 to huD1D5-V12, were obtained whose heavy/light chain variable region sequence ID numbers were in Table 1.

The vectors each containing a nucleotide encoding a humanized heavy chain variable region linked to human IgG4 heavy-chain constant region (SEQ ID NO: 78), and the vectors each containing a nucleotide encoding a humanized light chain variable region linked to human kappa light-chain constant region (SEQ ID NO: 79) were transiently transfected into 200 ml of 293F suspension cell cultures in a ratio of 1.1:1 light to heavy chain construct, with 1 mg/mL PEI.

Example 8 Characterization of Humanized Antibodies

Cell supernatants containing humanized antibodies were harvested after six days in shaking flasks and tested for binding affinities to human CTLA4 by Octet following the protocol described above, along with the chimeric antibodies and the benchmark in HBS-EP$^+$ at 5 μg/ml concentration. The $K_a$, $K_d$ and $K_D$ values were determined and summarized in Table 4 and 5 below.

TABLE 4

Binding Affinity of Humanized C1D1 mAbs

| | Kinetics on Octet Human CTLA4 | | |
|---|---|---|---|
| Clone ID | $K_a$ $(M-1s-1)$ | $K_d$ $(s-1)$ | $K_D$ $(M)$ |
| huCTLA4 C1D1-V1 | 2.50E+05 | 4.61E−05 | 1.84E−10 |
| hu CTLA4 C1D1-V2 | 2.67E+05 | 1.49E−04 | 5.59E−10 |

TABLE 4-continued

Binding Affinity of Humanized C1D1 mAbs

| | Kinetics on Octet Human CTLA4 | | |
|---|---|---|---|
| Clone ID | $K_a$ $(M-1s-1)$ | $K_d$ $(s-1)$ | $K_D$ $(M)$ |
| hu CTLA4 C1D1-V3 | 2.24E+05 | 2.59E−04 | 1.16E−09 |
| hu CTLA4 C1D1-V4 | 2.40E+05 | 2.29E−04 | 9.52E−10 |
| hu CTLA4 C1D1-V5 | 2.29E+05 | 4.76E−04 | 2.08E−09 |
| hu CTLA4 C1D1-V6 | 3.49E+05 | 2.87E−04 | 8.21E−10 |
| hu CTLA4 C1D1-V7 | 4.66E+05 | 1.69E−04 | 3.62E−10 |
| hu CTLA4 C1D1-V8 | 3.09E+05 | 1.90E−04 | 6.14E−10 |
| hu CTLA4 C1D1-V9 | 3.10E+05 | 2.28E−04 | 7.36E−10 |
| hu CTLA4 C1D1-V10 | 3.22E+05 | 3.04E−04 | 9.43E−10 |
| hu CTLA4 C1D1-V11 | 3.65E+05 | 4.57E−04 | 1.25E−09 |
| hu CTLA4 C1D1-V12 | 3.06E+05 | 3.04E−04 | 9.95E−10 |
| Chimeric C1D1 | 5.25E+05 | <1.0E−07 | <1.0E−12 |
| Yervoy ® | 2.25E+05 | 7.14E−04 | 3.17E−09 |

TABLE 5

Binding Affinity of Humanized D1D5 mAbs

| | Kinetics on Octet Human CTLA4 | | |
|---|---|---|---|
| Clone ID | $K_a$ $(M-1s-1)$ | $K_d$ $(s-1)$ | $K_D$ $(M)$ |
| huCTLA4 D1D5-V1 | 8.20E+04 | <1.0E−07 | <1.0E−12 |
| hu CTLA4 D1D5-V2 | 8.68E+04 | 6.25E−05 | 7.20E−10 |
| hu CTLA4 D1D5-V3 | 1.15E+05 | <1.0E−07 | <1.0E−12 |
| hu CTLA4 D1D5-V4 | 9.35E+04 | 4.08E−04 | 4.36E−09 |
| hu CTLA4 D1D5-V5 | 1.04E+05 | 1.80E−04 | 1.73E−09 |
| hu CTLA4 D1D5-V6 | 6.09E+04 | 1.57E−03 | 2.58E−08 |
| hu CTLA4 D1D5-V7 | 8.39E+04 | 8.57E−04 | 1.02E−08 |
| hu CTLA4 D1D5-V8 | 2.88E+04 | 1.96E−03 | 6.81E−08 |
| hu CTLA4 D1D5-V9 | 1.08E+05 | 4.71E−04 | 4.37E−09 |
| hu CTLA4 D1D5-V10 | 4.93E+04 | 1.63E−03 | 3.30E−08 |
| hu CTLA4 D1D5-V11 | 7.75E+04 | 5.38E−04 | 6.94E−09 |
| hu CTLA4 D1D5-V12 | 3.55E+04 | 1.33E−03 | 3.74E−08 |
| Chimeric D1D5 | 1.32E+05 | <1.0E−07 | <1.0E−12 |
| Yervoy ® | 1.70E+05 | 4.59E−04 | 2.70E−09 |

The data indicated that all cell supernatants containing humanized C1D1 antibodies showed higher binding affinity to human CTLA4 than the benchmark, and cell supernatants containing huCTLA4 D1D5-V1 to huCTLA4 D1D5-V3 showed higher binding affinity to human CTLA4 than the benchmark.

The humanized antibodies huC1D1-V8 and huD1D5-V9 were purified as described above and tested in Biacore, capture ELISA, benchmark blocking ELISA, cell-based ligand-blocking FACS and cell-based T cell response promotion tests, following the protocols in foregoing Examples with minor modifications. In the capture ELISA assay, the 96-well micro plates were coated with 2 μg/ml goat anti-human IgG (AffiniPure Goat Anti-Human IgG, F(ab')₂ fragment specific, Jackson Immunoresearch, Cat #109-005-097) instead of the goat anti-mouse IgG F(ab')₂ fragment, 100 μl/well. In the Biacore test, goat anti-human IgG (GE healthcare, Cat #BR100839, Human Antibody Capture Kit) was covalently linked to a CM5 chip instead of goat anti-mouse IgG, a CM5 chip was used for the benchmark instead of a Protein G chip.

The purified antibodies were also tested in the thermal stability assay to determine Tm (melting temperature) using a GloMelt™ Thermal Shift Protein Stability Kit (Biotium, Cat #33022-T). Briefly, the GloMelt™ dye was allowed to thaw and reach room temperature. The vial containing the dye was vortexed and centrifuged. Then, 10× dye was prepared by adding 5 µL 200× dye to 95 µL PBS. 2 µL 10× dye and 10 µg humanized antibodies were added, and PBS was added to a total reaction volume of 20 µL. The tubes containing the dye and antibodies were briefly spun and placed in real-time PCR thermocycler (Roche, LightCycler 480 II) set up with a melt curve program having the parameters in Table 6.

TABLE 6

Parameters for Melt Curve Program

| Profile step | Temperature | Ramp rate | Holding Time |
|---|---|---|---|
| 1nitial hold | 25° C. | NA | 30 s |
| Melt curve | 25-99° C. | 0.1° C./s | NA |

The results were shown in Table 7 and FIGS. 7A-7B, 8A-8B, 9A-9B, 10 and 11A-11B.

TABLE 7

Binding Affinity of Humanized antibodies huC1D1-V8 and huD1D5-V9

| | Kinetics on Biacore | | | | | |
|---|---|---|---|---|---|---|
| | Human CTLA4-his | | | Cynomolgus CTLA4-his | | |
| Clone ID# | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| chimeric C1D1 | 6.70E+05 | 4.22E−04 | 6.29E−10 | 1.64E+06 | 3.98E−04 | 2.43E−10 |
| huC1D1-V8 | 7.19E+04 | 8.60E−04 | 1.2 E−08 | 1.50E+05 | 0.001119 | 7.49E−09 |
| Chimeric D1D5 | 2.09E+05 | 4.04E−04 | 1.93E−09 | 5.21E+05 | 5.05E−04 | 9.68E−10 |
| huD1D5-V9 | 1.72E+05 | 5.19E−04 | 3.02E−09 | 2.71E+05 | 5.76E−04 | 2.13E−09 |
| Yervoy ® | 3.08E+05 | 0.001212 | 3.93E−09 | 3.11E+05 | 6.85E−04 | 2.2E−09 |

Figure 9A:
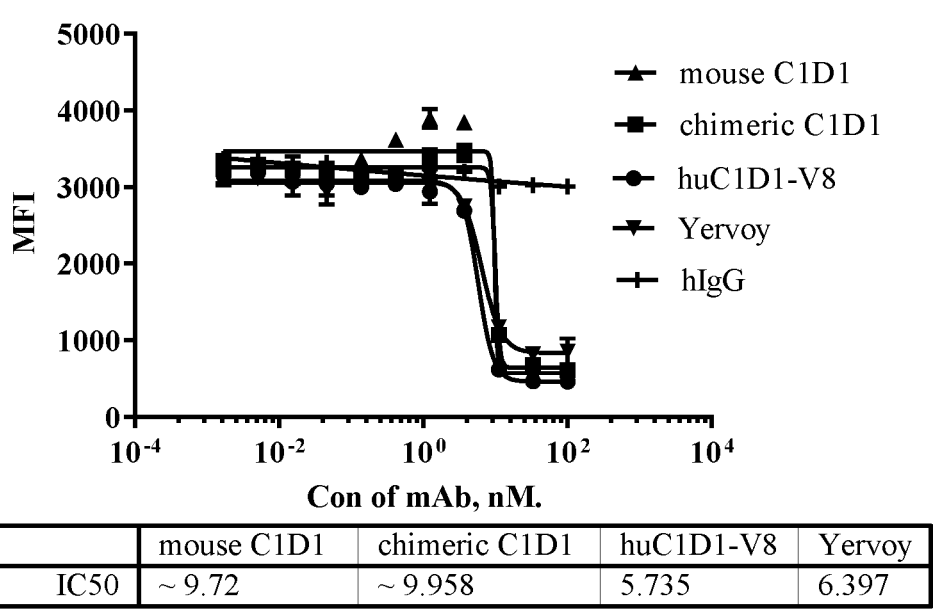
FIGS. 9A and 9B show the abilities of humanized antibodies huC1D1-V8 (A) and huD1D5-V9 (B) to block CTLA4 binding to cell surface CD80/CD86 in a cell based blocking FACS assay.

It can be seen from Table 7 that the antibody huC1D1-V8 showed lower binding affinity to human CTLA4 and cynomolgus monkey CTLA4 than the parent antibody or the benchmark. FIG. 9A showed that this antibody effectively blocked CTLA4 binding to cell surface CD80/CD86, and the blocking activity was comparable when compared to the benchmark.

Figure 9B:
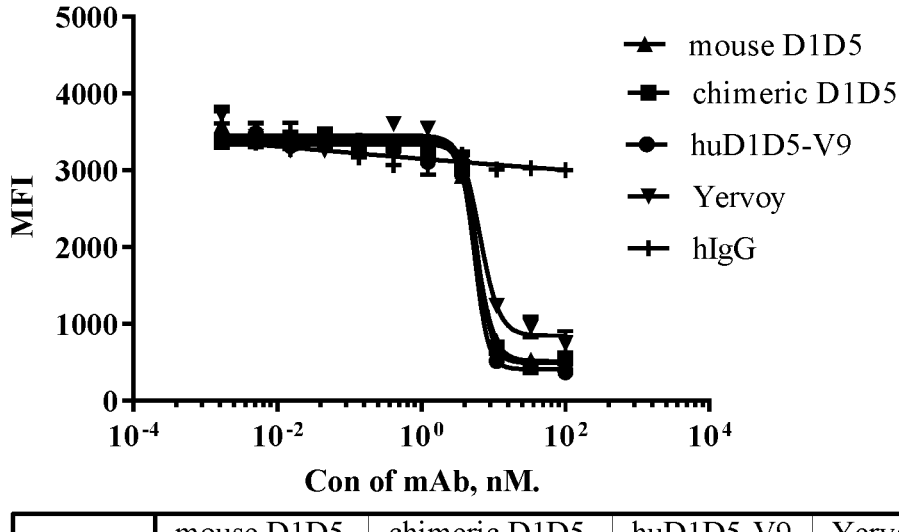

It also can be seen from Table 7 that the antibody huD1D5-V9 had comparable binding affinity to human CTLA4 and cynomolgus monkey CTLA4. FIG. 9B showed that this antibody effectively blocked CTLA4 binding to cell surface CD80/CD86 with a bit higher blocking capacity when compared to the benchmark.

Figure 8A:
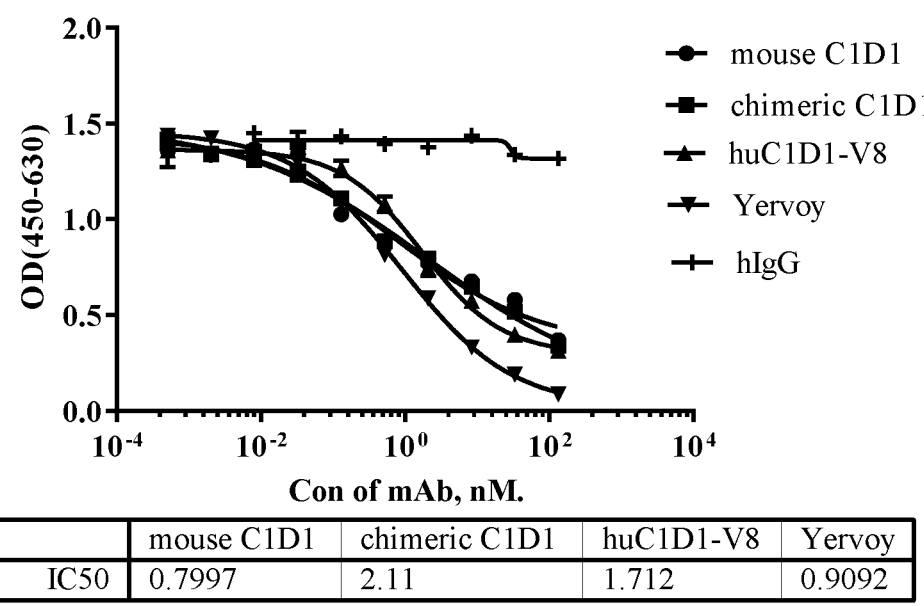
FIGS. 8A and 8B show the abilities of humanized antibodies huC1D1-V8 (A) and huD1D5-V9 (B) to block benchmark-human CTLA4 binding in a competitive ELISA.
Figure 8B:
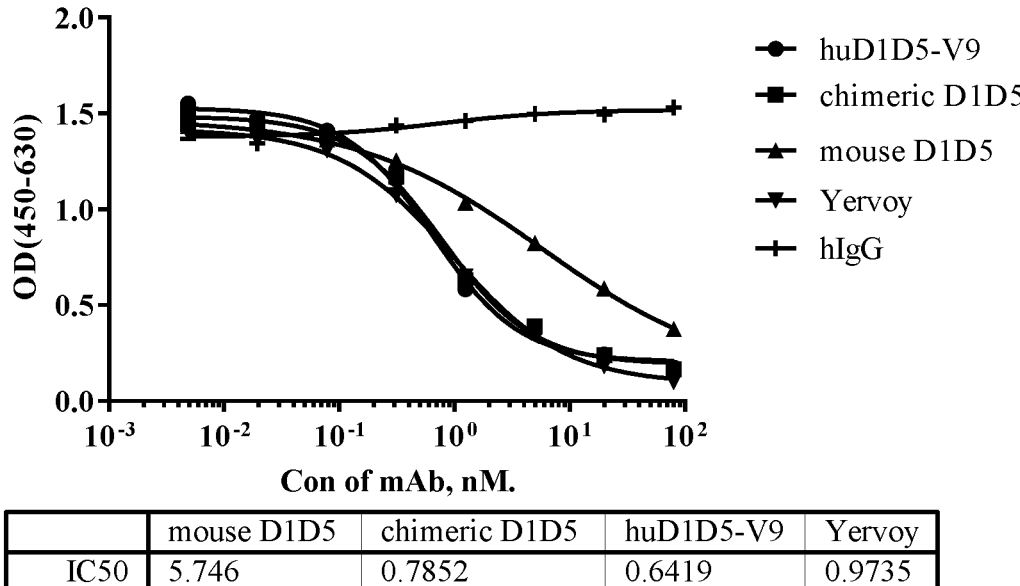

According to FIGS. 8A-8B, the humanized antibodies huC1D1-V8 and huD1D5-V9 of the disclosure were able to block human CTLA4-BM binding, suggesting that the anti-bodies huC1D1-V8 and huD1D5-V9 of the disclosure might bind to a similar epitope as BM did.

Figure 10:
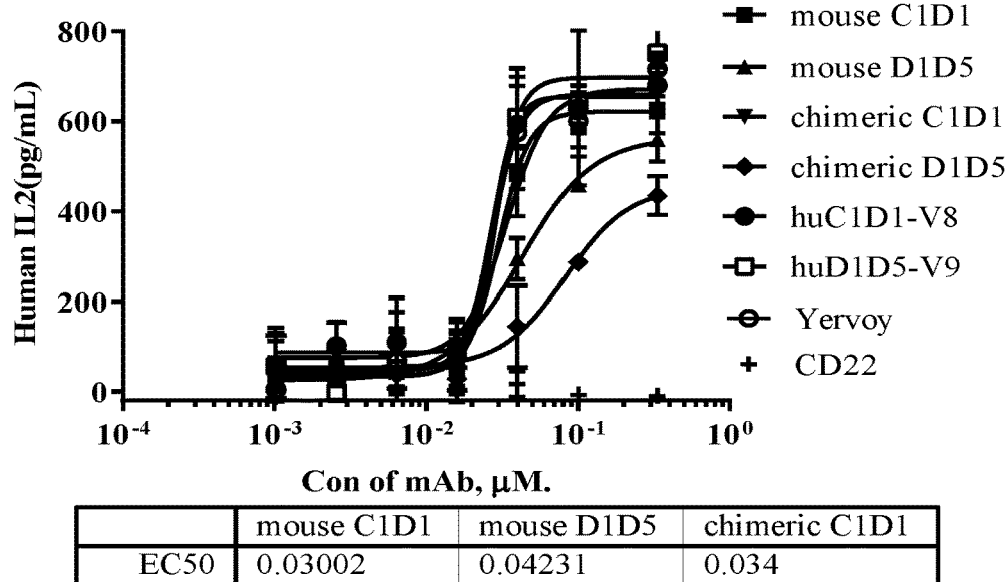
FIG. 10 shows that humanized antibodies huC1D1-V8 and huD1D5-V9 blocked CTLA4-CD80 binding and induced IL-2 release in a cell based functional assay.
Figure 11A:
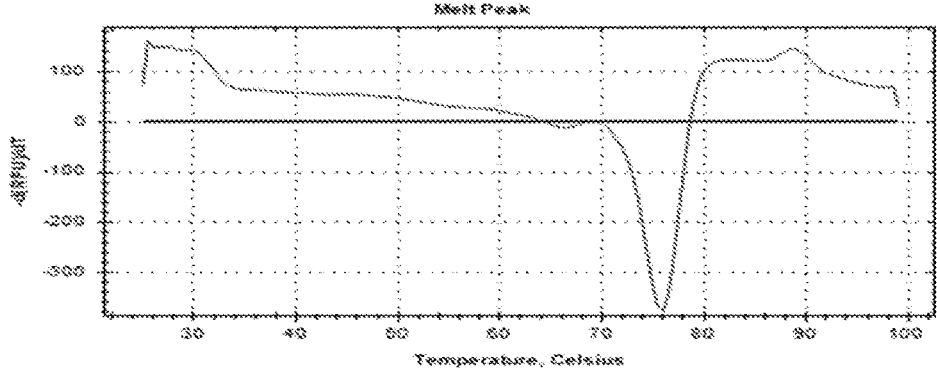
FIGS. 11A and 11B show the protein thermal shift assay results of humanized antibodies huC1D1-V8 (A) and huD1D5-V9 (B).
Figure 11B:
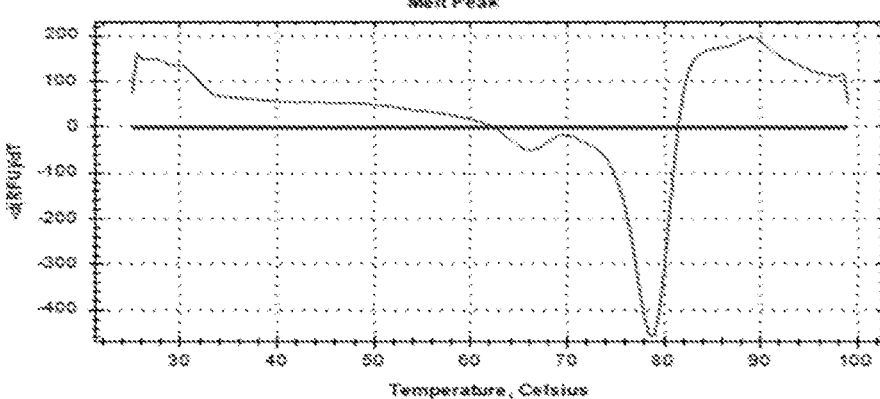

As shown in FIG. 10, the humanized antibodies huC1D1-V8 and huD1D5-V9 of the disclosure had comparable activities of promoting T cell response when compared to the BM.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

Description/Sequence/SEQ ID NO.

VH CDR1 for mouse, chimeric and humanized C1D1
DNWMN (SEQ ID NO: 1)

VH CDR2 for mouse, chimeric and humanized C1D1
QIRNKPYNYETYYSDSVKG (SEQ ID NO: 2)

VH CDR3 for mouse, chimeric and humanized C1D1
GMDY (SEQ ID NO: 3)

VL CDRI for mouse, chimeric and humanized C1D1
GASEIIYGALN (SEQ ID NO: 4)

VL CDR2 for mouse, chimeric and humanized C1D1
GATNLAD (SEQ ID NO: 5)

-continued

---
Description/Sequence/SEQ ID NO.
---

VL CDR3 for mouse, chimeric and humanized C1D1
QKILSPPPWT (SEQ ID NO: 6)

VH for mouse and chimeric C1D1

EVKLDETGGGLVQPGRPLKLSCVASGFTFSDNWMNWVRQSPEKGLEWVAQIRNKPYNYE
TYYSDSVKGRFTISRDDSKSSVYLQMNNLRVEDMGIYYCTGGMDYWGQGTSVTVSS
(SEQ ID NO: 54)

GAGGTGAAGCTGGATGAGACTGGAGGAGGCTTGGTGCAACCTGGGAGGCCCCTGAAA
CTCTCCTGTGTTGCCTCTGGATTCACTTTTAGTGACAACTGGATGAACTGGGTCCGCCA
GTCTCCAGAGAAAGGACTGGAGTGGGTAGCACAAATTAGAAACAAACCTTATAATTAT
GAAACATATTATTCAGATTCTGTGAAAGGCAGATTCACCATCTCAAGAGATGATTCCA
AAAGTAGTGTCTACCTGCAAATGAACAACTTAAGAGTTGAAGACATGGGTATCTATTA
CTGTACAGGCGGGATGGACTACTGGGGTCAAGGAACCTCAGTCACCGTCTCCTCA
(SEQ ID NO: 80)

GAGGTGAAGCTGGACGAGACCGGCGGCGGCCTGGTGCAACCAGGAAGACCCCTGAAG
CTGTCCTGCGTGGCCAGCGGCTTCACATTCAGCGACAATTGGATGAACTGGGTGAGGC
AGAGCCCTGAGAAGGGCCTGGAGTGGGTGGCCCAGATCAGAAATAAGCCTTACAACT
ACGAGACCTACTACAGCGACTCCGTGAAGGGCAGGTTCACAATCAGCAGAGACGACA
GCAAGTCCAGCGTGTACCTGCAGATGAACAATCTGAGAGTGGAGGACATGGGCATCTA
CTACTGTACCGGCGGCATGGATTACTGGGGCCAGGGCACAAGCGTGACCGTGTCCAGC
(SEQ ID NO: 81)

VH for huC1D1-V1, huC1D1-V5 and huC1D1-V9
EVQLVESGGGLVQPGRSLRLSCTASGFTFSDNWMNWVRQAPGKGLEWVX1QIRNKPYNY
ETYYSDSVKGRFTISRDDSKSIX2YLQMNSLKTEDTAVYYCTGGMDYWGQGTTVTVSS
(SEQ ID NO: 55) X1 = A, X2 = V
EVQLVESGGGLVQPGRSLRLSCTASGFTFSDNWMNWVRQAPGKGLEWVAQIRNKPYNYE
TYYSDSVKGRFTISRDDSKSIVYLQMNSLKTEDTAVYYCTGGMDYWGQGTTVTVSS VH for huC1D1-V2, huC1D1-V6 and huC1D1-V10
EVQLVESGGGLVQPGRSLRLSCTASGFTFSDNWMNWVRQAPGKGLEWVXIQIRNKPYNY
ETYYSDSVKGRFTISRDDSKSIX2YLQMNSLKTEDTAVYYCTGGMDYWGQGTTVTVSS
(SEQ ID NO: 55) X1 = A, X2 = A
EVQLVESGGGLVQPGRSLRLSCTASGFTFSDNWMNWVRQAPGKGLEWVAQIRNKPYNYE
TYYSDSVKGRFTISRDDSKSIAYLQMNSLKTEDTAVYYCTGGMDYWGQGTTVTVSS VH for huC1D1-V3, huC1D1-V7 and huC1D1-V11
EVQLVESGGGLVQPGRSLRLSCTASGFTFSDNWMNWVRQAPGKGLEWVX1QIRNKPYNY
ETYYSDSVKGRFTISRDDSKSIX2YLQMNSLKTEDTAVYYCTGGMDYWGQGTTVTVSS
(SEQ ID NO: 55) X1 = G, X2 = V
EVQLVESGGGLVQPGRSLRLSCTASGFTFSDNWMNWVRQAPGKGLEWVGQIRNKPYNYE
TYYSDSVKGRFTISRDDSKSIVYLQMNSLKTEDTAVYYCTGGMDYWGQGTTVTVSS VH for huC1D1-V4, huC1D1-V8 and huC1D1-V12
EVQLVESGGGLVQPGRSLRLSCTASGFTFSDNWMNWVRQAPGKGLEWVX1QIRNKPYNY
ETYYSDSVKGRFTISRDDSKSIX2YLQMNSLKTEDTAVYYCTGGMDYWGQGTTVTVSS
(SEQ ID NO: 55) X1 = G, X2 = A
EVQLVESGGGLVQPGRSLRLSCTASGFTFSDNWMNWVRQAPGKGLEWVGQIRNKPYNY
TYYSDSVKGRFTISRDDSKSIAYLQMNSLKTEDTAVYYCTGGMDYWGQGTTVTVSS
GAGGTGCAGCTGGTGGAGTCCGGCGGCGGACTGGTGCAGCCTGGAAGAAGCCTGAGA
CTGTCCTGTACCGCCAGCGGCTTCACCTTCTCCGACAACTGGATGAATTGGGTGAGGC
AGGCCCCTGGCAAGGGCCTGGAGTGGGTGGGACAGATCAGAAATAAGCCCTACAATT
ACGAGACATACTACTCCGATTCCGTGAAGGGCAGATTCACCATCTCCAGGGATGATAG
CAAGAGCATCGCCTACCTGCAGATGAATTCCCTGAAGACCGAGGACACCGCCGTGTAC
TACTGTACCGGCGGCATGGACTACTGGGGCCAGGGCACCACAGTGACAGTGTCCAGC
(SEQ ID NO: 82)

VL for mouse and chimeric C1D1
DIQMTQSPASLSASVGETVTITCGASEIIYGALNWYQQKQGKSPQLLIYGATNLADGMSSR
FSGSGSGRQYSLKISSLHPDDAATYYCQKILSPPPWTFGGGTKLEIK (SEQ ID NO: 56)
GACATTCAGATGACTCAGTCTCCAGCTTCACTGTCTGCATCTGTGGGAGAAACTGTCAC
CATCACATGTGGAGCAAGTGAGATTATTTACGGTGCTTTAAATTGGTATCAGCAGAAA
CAGGGAAAATCTCCTCAGCTCCTGATCTATGGTGCAACCAACTTGGCAGATGGCATGT
CATCGAGGTTCAGTGGCAGTGGATCTGGTAGACAATATTCTCTCAAGATCAGTAGCCT
GCATCCTGACGATGCTGCAACATATTACTGTCAAAAAATATTAAGTCCTCCTCCGTGGA
CGTTCGGTGGAGGCACCAAGCTGGAGATCAAA (SEQ ID NO: 83)
GACATCCAGATGACACAGAGCCCCGCCAGCCTGTCCGCCAGCGTTGGAGAGACCGTG
ACAATCACATGTGGCGCCTCCGAGATCATCTACGGCGCCCTGAATTGGTATCAACAGA
AGCAGGGCAAGAGCCCCCAGCTGCTGATCTACGGCGCTACCAATCTGGCCGACGGCAT
GAGCTCCAGGTTCTCCGGCAGCGGCAGCGGCAGGCAGTACAGCCTGAAGATCTCCAGC
CTGCACCCCGACGACGCCGCCACATACTACTGCCAGAAGATCCTGTCCCCCCCTCCTTG
GACATTCGGCGGCGGCACCAAGCTGGAGATCAAG (SEQ ID NO: 84)

-continued

| Description/Sequence/SEQ ID NO. |
|---|

VL for huC1D1-V1 - huC1D1-V4
DIQMTQSPSSLSASVGDRVTITCGASEIIYGALNWYQQKPGKX1PKLLIYGATNLADGX2PS
RFSGSGSGX3DX4TLTISSLQPEDVATYYCQKILSPPPWTFGGGTKVEIK (SEQ ID NO: 57)
X1 = S, X2 = M, X3 = R, X4 = Y
DIQMTQSPSSLSASVGDRVTITCGASEIIYGALNWYQQKPGKSPKLLIYGATNLADGMPSRF
SGSGSGRDYTLTISSLQPEDVATYYCQKILSPPPWTFGGGTKVEIK VL for huC1D1-V5 - huC1D1-V8
DIQMTQSPSSLSASVGDRVTITCGASEIIYGALNWYQQKPGKX1PKLLIYGATNLADGX2PS
RFSGSGSGX3DX4TLTISSLQPEDVATYYCQKILSPPPWTFGGGTKVEIK (SEQ ID NO: 57)
X1 = S, X2 = V, X3-T, X4 = F
DIQMTQSPSSLSASVGDRVTITCGASEIIYGALNWYQQKPGKSPKLLIYGATNLADGVPSRF
SGSGSGTDFTLTISSLQPEDVATYYCQKILSPPPWTFGGGTKVEIK
GATATCCAGATGACACAGTCCCCCTCCTCCCTGAGCGCCTCCGTGGGAGACAGAGTGA
CCATCACCTGTGGCGCCTCCGAGATCATCTACGGCGCCCTGAATTGGTATCAACAGAA
GCCCGGCAAGAGCCCCAAGCTGCTGATCTACGGCGCTACAAACCTGGCCGATGGCGTG
CCTTCCAGGTTTAGCGGCTCCGGCTCGGCACCGACTTCACCCTGACCATCTCCTCCCT
GCAGCCCGAGGATGTGGCCACATACTACTGTCAGAAGATCCTGAGCCCCCCCCCTTGG
ACCTTCGGCGGAGGAACAAAGGTGGAGATCAAG (SEQ ID NO: 85)

VL for huC1D1-V9 - huC1D1-V12
DIQMTQSPSSLSASVGDRVTITCGASEIIYGALNWYQQKPGKX1PKLLIYGATNLADGX2PS
RFSGSGSGX3DX4TLTISSLQPEDVATYYCQKILSPPPWTFGGGTKVEIK (SEQ ID NO: 57)
X1 = V, X2 = V, X3 = T, X4 = F
DIQMTQSPSSLSASVGDRVTITCGASEIIYGALNWYQQKPGKVPKLLIYGATNLADGVPSRF
SGSGSGTDFTLTISSLQPEDVATYYCQKILSPPPWTFGGGTKVEIK VH CDR1 for mouse, chimeric and humanized D1D5
DYGMA (SEQ ID NO: 7)

VH CDR2 for mouse, chimeric and humanized D1D5
FISNLAYSVYYADTETG (SEQ ID NO: 8)

VH CDR3 for mouse, chimeric and humanized D1D5
SGLPYAMDY (SEQ ID NO: 9)

VL CDR1 for mouse, chimeric and humanized D1D5
RASQDISNYLN (SEQ ID NO: 10)

VL CDR2 for mouse, chimeric and humanized D1D5
YISRLHS (SEQ ID NO: 11)

VL CDR3 for mouse, chimeric and humanized D1D5
QQGRMLPWT (SEQ ID NO: 12)

VH for mouse and chimeric D1D5
EVKLVESGGGLVKPGGSLKLSCAASGFTFSDYGMAWVRQAPGKGPEWVAFISNLAYSVY
YADTETGRFTISREDAKNTLYLEMSSLRSEDTAMYYCARSGLPYAMDYWGQGTSVTVSS
(SEQ ID NO: 58)
GAGGTGAAGCTGGTGGAGTCTGGGGGAGGCTTAGTGAAGCCTGGAGGGTCCCTGAAA
CTCTCCTGTGCAGCCTCTGGATTCACTTTCAGTGACTACGGAATGGCGTGGGTTCGACA
GGCTCCAGGGAAGGGGCCTGAGTGGGTAGCATTCATTAGTAATTTGGCATATAGTGTC
TACTATGCAGACACTGAGACGGGCCGATTCACCATCTCTAGAGAGGATGCCAAGAACA
CCCTGTACTTGGAAATGAGCAGTCTGAGGTCTGAGGACACAGCCATGTATTACTGTGC
AAGAAGTGGACTACCCTATGCTATGGACTACTGGGGTCAAGGAACCTCAGTCACCGTC
TCCTCA (SEQ ID NO: 86)
GAGGTGAAGCTGGTGGAGTCCGGCGGCGGCCTGGTGAAGCCAGGAGGAAGCCTGAAG
CTGTCCTGCGCCGCCTCCGGCTTCACATTCTCCGACTACGGCATGGCCTGGGTGAGGCA
GGCCCCTGGAAAGGGCCCTGAGTGGGTGGCCTTCATCTCCAATCTGGCCTACAGCGTG
TACTACGCCGATACCGAGACAGGCAGGTTCACCATCTCCAGAGAGGACGCCAAGAAT
ACACTGTACCTGGAGATGAGCAGCCTGAGATCCGAGGACACAGCCATGTACTACTGCG
CCAGGAGCGGCCTGCCTTACGCCATGGATTACTGGGGCCAGGGCACAAGCGTGACCGT
GAGCTCC (SEQ ID NO: 87)

VH for huD1D5-V1, huD1D5-V5 and huD1D5-V9
EVQLVESGGGLVKPGGSLRLSCAASGFTFSDYGMAWVRQAPGKGX1EWVX2FISNLAYSV
YYADTETGRFTISRDX3AKNSLYLQMNSLRAEDTAVYYCARSGLPYAMDYWGQGTTVTV
SS (SEQ ID NO: 59) X1-P, X2 = A, X3 = D
EVQLVESGGGLVKPGGSLRLSCAASGFTFSDYGMAWVRQAPGKGPEWVAFISNLAYSVY
YADTETGRFTISRDDAKNSLYLQMNSLRAEDTAVYYCARSGLPYAMDYWGQGTTVTVSS
GAGGTGCAGCTGGTGGAGTCCGGCGGCGGACTGGTGAAGCCTGGCGGATCCCTGAGG
CTGTCCTGTGCCGCCTCCGGCTTCACCTTCTCCGACTACGGCATGGCCTGGGTGAGGCA
GGCCCCTGGAAAGGGCCCCGAGTGGGTGGCTTTCATCTCCAATCTGGCCTACAGCGTG
TACTACGCCGATACAGAGACAGGCAGGTTCACCAATCAGCAGGGATGACGCCAAGAAC
AGCCTGTACCTGCAGATGAACTCCCTGAGGGCCGAGGATACCGCCGTGTACTACTGTG
CCAGGTCCGGCCTGCCCTACGCCATGGATTACTGGGGCCAGGGCACAACAGTGACAGT
GAGCAGC (SEQ ID NO: 88)

-continued

---

Description/Sequence/SEQ ID NO.

---

VH for huD1D5-V2, huD1D5-V6 and huD1D5-V10
EVQLVESGGGLVKPGGSLRLSCAASGFTFSDYGMAWVRQAPGKGX1EWVX2FISNLAYSV
YYADTETGRFTISRDX3AKNSLYLQMNSLRAEDTAVYYCARSGLPYAMDYWGQGTTVTV
SS (SEQ ID NO: 59) X1 = L, X2 = A, X3 = N
EVQLVESGGGLVKPGGSLRLSCAASGFTFSDYGMAWVRQAPGKGLEWVAFISNLAYSVY
YADTETGRFTISRDNAKNSLYLQMNSLRAEDTAVYYCARSGLPYAMDYWGQGTTVTVSS VH for huD1D5-V3, huD1D5-V7 and huD1D5-V11
EVQLVESGGGLVKPGGSLRLSCAASGFTFSDYGMAWVRQAPGKGX1EWVX2FISNLAYSV
YYADTETGRFTISRDX3AKNSLYLQMNSLRAEDTAVYYCARSGLPYAMDYWGQGTTVTV
SS (SEQ ID NO: 59) X1 = L, X2 = A, X3 = D
EVQLVESGGGLVKPGGSLRLSCAASGFTFSDYGMAWVRQAPGKGLEWVAFISNLAYSVY
YADTETGRFTISRDDAKNSLYLQMNSLRAEDTAVYYCARSGLPYAMDYWGQGTTVTVSS VH for huD1D5-V4, huD1D5-V8 and huD1D5-V12
EVQLVESGGGLVKPGGSLRLSCAASGFTFSDYGMAWVRQAPGKGX1EWVX2FISNLAYSV
YYADTETGRFTISRDX3AKNSLYLQMNSLRAEDTAVYYCARSGLPYAMDYWGQGTTVTV
SS (SEQ ID NO: 59) X1 = L, X2 = S, X3 = N
EVQLVESGGGLVKPGGSLRLSCAASGFTFSDYGMAWVRQAPGKGLEWVSFISNLAYSVY
YADTETGRFTISRDNAKNSLYLQMNSLRAEDTAVYYCARSGLPYAMDYWGQGTTVTVSS VL for mouse and chimeric D1D5
DIQMTQTTSSLSASLGDRVTISCRASQDISNYLNWYQQKPDGTVKLLIYYISRLHSGVPSRF
SGSGSGTDFSLTISNLEQEDIATYFCQQGRMLPWTFGGGTRLEIK (SEQ ID NO: 60)
GATATCCAGATGACACAGACTACATCCTCCCTGTCTGCCTCGCTGGGAGACAGAGTCA
CCATCAGTTGCAGGGCCAGTCAGGACATTAGCAATTATTTAAACTGGTATCAGCAGAA
ACCAGATGGAACTGTTAAACTCCTGATCTACTACATATCAAGATTACACTCAGGAGTC
CCATCAAGGTTCAGTGGCAGTGGGTCTGGGACAGATTTTTCTCTCACCATTAGCAACCT
GGAACAAGAAGATATTGCCACTTACTTTTGCCAACAGGGTCGTATGCTTCCGTGGACG
TTCGGTGGAGGCACCAGGCTGGAAATCAAA (SEQ ID NO: 89)
GATATCCAGATGACCCAGACAACAAGCAGCCTGAGCGCCTCCCTGGGCGATAGAGTG
ACAATCTCCTGCAGGGCCAGCCAGGATATCAGCAACTACCTGAATTGGTATCAACAGA
AGCCTGATGGCACCGTGAAGCTGCTGATCTACTACATCTCCAGACTGCACAGCGGCGT
GCCCAGCAGATTCTCCGGCAGCGGCAGCGGCACCGACTTCTCCCTGACCATCTCCAAT
CTGGAGCAGGAGGATATCGCCACATACTTCTGCCAGCAGGGCAGAATGCTGCCTTGGA
CATTCGGCGGCGGCACCAGACTGGAGATCAAG (SEQ ID NO: 90)

VL for huD1D5-V1 - huD1D5-V4
DIQMTQSPSSLSASVGDRVTITCRASQDISNYLNWYQQKPGKX1X2KLLIYYISRLHSGVPS
RFSGSGSGTDFTLTISSLQPEDVATYX3CQQGRMLPWTFGGGTKVEIK (SEQ ID NO: 61)
X1 = T, X2 = V, X3 = F
DIQMTQSPSSLSASVGDRVTITCRASQDISNYLNWYQQKPGKTVKLLIYYISRLHSGVPSRF
SGSGSGTDFTLTISSLQPEDVATYFCQQGRMLPWTFGGGTKVEIK VL for huD1D5-V5 - huD1D5-V8
DIQMTQSPSSLSASVGDRVTITCRASQDISNYLNWYQQKPGKX1X2KLLIYYISRLHSGVPS
RFSGSGSGTDFTLTISSLQPEDVATYX3CQQGRMLPWTFGGGTKVEIK (SEQ ID NO: 61)
X1 = V, X2 = P, X3 = F
DIQMTQSPSSLSASVGDRVTITCRASQDISNYLNWYQQKPGKVPKLLIYYISRLHSGVPSRF
SGSGSGTDFTLTISSLQPEDVATYFCQQGRMLPWTFGGGTKVEIK VL for huD1D5-V9 - huD1D5-V12
DIQMTQSPSSLSASVGDRVTITCRASQDISNYLNWYQQKPGKX1X2KLLIYYISRLHSGVPS
RFSGSGSGTDFTLTISSLQPEDVATYX3CQQGRMLPWTFGGGTKVEIK (SEQ ID NO: 61)
X1 = V, X2 = P, X3 = Y
DIQMTQSPSSLSASVGDRVTITCRASQDISNYLNWYQQKPGKVPKLLIYYISRLHSGVPSRF
SGSGSGTDFTLTISSLQPEDVATYYCQQGRMLPWTFGGGTKVEIK
GACATCCAGATGACACAGTCCCCTAGCAGCCTGAGCGCCAGCGTGGGCGACAGGGTG
ACCATCACATGTAGAGCCAGCCAGGACATCTCCAATTACCTGAATTGGTATCAACAGA
AGCCCGGCAAGGTGCCTAAGCTGCTGATCTACTACATCAGCAGGCTGCACTCCGGCGT
GCCCTCCAGATTCAGCGGCAGCGGCTCCGGCACCGATTTTACCCTGACAATCTCCAGC
CTGCAGCCTGAGGACGTGGCCACATACTACTGCCAGCAGGGCAGGATGCTGCCTTGGA
CATTCGGCGGCGGCACAAAGGTGGAGATCAAG (SEQ ID NO: 91)

VH CDR1 for mouse C1G4
DNWMN (SEQ ID NO: 1)

VH CDR2 for mouse C1G4
QIRNKPYNYETYYSDSVKG (SEQ ID NO: 2)

VH CDR3 for mouse C1G4
GFTY (SEQ ID NO: 13)

VL CDR1 for mouse C1G4
GASENIYGGLN (SEQ ID NO: 14)

-continued

| Description/Sequence/SEQ ID NO. |
|---|

VL CDR2 for mouse C1G4
GATNLAD (SEQ ID NO: 5)

VL CDR3 for mouse C1G4
QNVLNTPYT (SEQ ID NO: 15)

VH for mouse C1G4
EVKLDETGGGLVQPGRPIKLSCVASGFTFSDNWMNWVRQSPEKGLEWVAQIRNKPYNYE
TYYSDSVKGRFTISRDDSKSSVYLQMNNLRTKDMGIYYCTGGFTYWGQGTLVTVSA (SEQ
ID NO: 62)

VL for mouse C1G4
DIQMTQSPPSLSASVGETVTITCGASENIYGGLNWYQRKQGKSPQLLIYGATNLADGMSSR
FSGSGSGRQYSLKISRLHPDDVATYYCQNVLNTPYTFGGGTKLEIK (SEQ ID NO: 63)

VH CDR1 for mouse D1A7
SSKLGVG (SEQ ID NO: 16)

VH CDR2 for mouse D1A7
HIWWNDDNYYVPSLKS (SEQ ID NO: 17)

VH CDR3 for mouse D1A7
VPYYTTQPWFAY (SEQ ID NO: 18)

VL CDR1 for mouse D1A7
RASGNIHNYLA (SEQ ID NO: 19)

VL CDR2 for mouse D1A7
NTETLAD (SEQ ID NO: 20)

VL CDR3 for mouse D1A7
QHLWSTPWT (SEQ ID NO: 21)

VH for mouse D1A7
QVTLKESGPGMLQPSQTLSLTCSFSGFSLSSSKLGVGWIRQPAGKGLEWLAHIWWNDDNY
YVPSLKSRLTISKDTSNNQVFLKITNVDAADTATYYCVQVPYYTTQPWFAYWGQGTLVTV
SA (SEQ ID NO: 64)

VL for mouse D1A7
DIQMTQSPASLSASVGETVTITCRASGNIHNYLAWYLQNQGRSPQLLVYNTETLADGVSSR
FSGSGSGTQYFLKISSLQPEDFGTYYCQHLWSTPWTFGGGTKLEIK (SEQ ID NO: 65)

VH CDR1 for mouse D1B6
TYVLN (SEQ ID NO: 22)

VH CDR2 for mouse D1B6
YFNPYNDGIKYNEKFKG (SEQ ID NO: 23)

VH CDR3 for mouse D1B6
FEGGGYAMDY (SEQ ID NO: 24)

VL CDR1 for mouse D1B6
RASQSVGTSRNTYIH (SEQ ID NO: 25)

VL CDR2 for mouse D1B6
YASDLES (SEQ ID NO: 26)

VL CDR3 for mouse D1B6
QHSWEIPYT (SEQ ID NO: 27)

VH for mouse D1B6
EVQLQQSGPELVKPGASVKLSCKASGNTFTTYVLNWVKQKPGQGLEWIGYFNPYNDGIK
YNEKFKGKATLTSDKSSNTAYMELSSLTSEDSAVYYCARFEGGGYAMDYWGQGTSVTVS
S (SEQ ID NO: 66)

VL for mouse D1B6
DIVLTQSPASLAVSLGQRATISCRASQSVGTSRNTYIHWYQQKLGQPPKLLIKYASDLESGV
PARFSGSGSGTDFTLNIHPVEEEDTATYYCQHSWEIPYTFGGGTKLEIK (SEQ ID NO: 67)

VH CDR1 for mouse D1B8
DYYIN (SEQ ID NO: 28)

VH CDR2 for mouse D1B8
WIYPGNNNTRYNEKFKG (SEQ ID NO: 29)

VH CDR3 for mouse D1B8
YYFDY (SEQ ID NO: 30)

-continued

| Description/Sequence/SEQ ID NO. |
| --- |

VL CDR1 for mouse D1B8
RASQEITGYLS (SEQ ID NO: 31)

VL CDR2 for mouse D1B8
AASTLDS (SEQ ID NO: 32)

VL CDR3 for mouse D1B8
LQYASYPRT (SEQ ID NO: 33)

VH for mouse D1B8
QIQLQQSGPELVKPGASVKISCKASGYTFTDYYINWVKQRPGQGLEWIGWIYPGNNNTRY
NEKFKGKATLTIDTSSSTAFMHLSSLTSEDSAVYFCARYYFDYWGQGTTLTVSS (SEQ ID
NO: 68)

VL for mouse D1B8
DIQMTQSPSSLSASLGERISLTCRASQEITGYLSWLQQKPDGTIKRLIYAASTLDSGVPQRFS
GSRSGSDYSLTISSLESEDFADYCLQYASYPRTFGGGTKLEIK (SEQ ID NO: 69)

VH CDR1 for mouse D1G6
TYVLN (SEQ ID NO: 22)

VH CDR2 for mouse D1G6
YFNPYNDAIKYNEKFKG (SEQ ID NO: 34)

VH CDR3 for mouse D1G6
FEGGGYAMDY (SEQ ID NO: 24)

VL CDR1 for mouse D1G6
RASQSVGTSSYSYIH (SEQ ID NO: 35)

VL CDR2 for mouse D1G6
YASDLES (SEQ ID NO: 26)

VL CDR3 for mouse D1G6
QHSWEIPYT (SEQ ID NO: 27)

VH for mouse D1G6
EVQLQQSGPELVKPGASVKLSCKASGNTFTTYVLNWVKQKPGQGLEWIGYFNPYNDAIK
YNEKFKGKATLTSDKSSSTAYMELSSLTSEDSAVYYCARFEGGGYAMDYWGQGTSVTVS
S (SEQ ID NO: 70)

VL for mouse D1G6
DIVLTQSPASLAVSLGQRATISCRASQSVGTSSYSYIHWYQQKPGQPPKLLIKYASDLESGV
PARFSGSGSGTDFTLNIHPVEEEDTATYYCQHSWEIPYTFGGGTKLEIK (SEQ ID NO: 71)

VH CDR1 for mouse D1H3
SYWLH (SEQ ID NO: 36)

VH CDR2 for mouse D1H3
RIDPNRGTIYYNEKFNN (SEQ ID NO: 37)

VH CDR3 for mouse D1H3
GGSNFYAMDY (SEQ ID NO: 38)

VL CDR1 for mouse D1H3
RTSENIYSYLA (SEQ ID NO: 39)

VL CDR2 for mouse D1H3
NAKTLAE (SEQ ID NO: 40)

VL CDR3 for mouse D1H3
QNHDGIPFT (SEQ ID NO: 41)

VH for mouse D1H3
QVQLQQPGAELVNPGASVKLSCKASGYTFTSYWLHWVKQRPGRGLEWIGRIDPNRGTIYY
NEKFNNKATVTVDKPSNTAYMQLSRLTLEDSAVYYCARGGSNFYAMDYWGQGTSVTVS
S (SEQ ID NO: 72)

VL for mouse D1H3
DIQMTQSPASLSASVGETVTITCRTSENIYSYLAWYQQKQGESPQLLVYNAKTLAEGVPSR
FSGSGSGTQFSLKINSLQPEDFGSYYCQNHDGIPFTFGSGTKLEIK (SEQ ID NO: 73)

VH CDR1 for mouse D1H4
DYYMN (SEQ ID NO: 42)

-continued

---

Description/Sequence/SEQ ID NO.

---

VH CDR2 for mouse D1H4
AINPDHGGSSYNQKFKG (SEQ ID NO: 43)

VH CDR3 for mouse D1H4
DGSIHYVMDD (SEQ ID NO: 44)

VL CDR1 for mouse D1H4
KSSQSLLHSGNQKNYLA (SEQ ID NO: 45)

VL CDR2 for mouse D1H4
GASTRES (SEQ ID NO: 46)

VL CDR3 for mouse D1H4
QNDYGYPYT (SEQ ID NO: 47)

VH for mouse D1H4
EVQLQQSGPVLVKPGASVKMSCKASGYTFTDYYMNWVKQSHGKSLEWIGAINPDHGGSS
YNQKFKGKATLTVDKSSSTAYMELNSLTSEDSAVYYCARDGSIHYVMDDWGQGTSVTVS
S (SEQ ID NO: 74)

VL for mouse D1H4
DIVMSQSPSSLTVSAGDKVTMSCKSSQSLLHSGNQKNYLAWYQQKPWQPPKLLIYGASTR
ESGVPDRFTGSGSGTDFTLTISSVQAEDLAVYYCONDYGYPYTFGGGTKLEIK (SEQ ID NO:
75)

VH CDR1 for mouse D2A4
SYWVH (SEQ ID NO: 48)

VH CDR2 for mouse D2A4
RIDPNRGGTYYNENFKT (SEQ ID NO: 49)

VH CDR3 for mouse D2A4
GGLNYYALDY (SEQ ID NO: 50)

VL CDR1 for mouse D2A4
RASENIYSYLA (SEQ ID NO: 51)

VL CDR2 for mouse D2A4
NANTLTE (SEQ ID NO: 52)

VL CDR3 for mouse D2A4
QHHYGIPFT (SEQ ID NO: 53)

VH for mouse D2A4
QVQLQQPGAELVKPGSSVNLSCKASGYTFTSYWVHWVKQGPGRGLEWIGRIDPNRGGTY
YNENFKTKAALTVDSPSSTAYMHLSSLTSEDSAVYYCARGGLNYYALDYWGQGTSVTVS
S (SEQ ID NO: 76)

VL for mouse D2A4
DIQMTQSPASLFASLGETVTITCRASENIYSYLAWYQQKQGKSPQLLVYNANTLTEGVPSS
FSGSGSGTQFSLKINTLQPEDFGTYYCQHHYGIPFTFGSGTKLEIK (SEQ ID NO: 77)

Heavy chain constant region
ASTKGPSVFPLAPCSRSTSESTAALGCLVKDYFPEPVTVSWNSGALTSGVHTFPAVLQSSGL
YSLSSVVTVPSSSLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSC
SVMHEALHNHYTQKSLSLSLGK (SEQ ID NO: 78)
GCCAGCACAAAGGGCCCTTCCGTGTTCCCCTGGCCCCCTGCAGCAGGAGCACCTCTG
AGTCCACCGCCGCCCTGGGCTGTCTGGTGAAGGACTACTTTCCCGAGCCCGTGACCGT
GAGCTGGAATTCCGGCGCCCTGACATCCGGCGTGCACACCTTCCCCGCCGTGCTGCAG
TCCTCCGGCCTGTACAGCCTGAGCTCCGTGGTGACAGTGCCTTCCTCCTCCCTGGGCAC
CAAGACCTACACATGTAATGTGGATCACAAGCCCAGCAACACAAAGGTGGATAAGAG
AGTGGAGTCCAAGTACGGCCCTCCTTGCCCTCCCTGTCCTGCCCCAGAGTTCCTGGGCG
GCCCCTCTGTGTTCCTGTTCCCCCCTAAGCCCAAGGACACACTGATGATCTCCAGGACC
CCTGAGGTGACCTGCGTGGTGGTGGACGTGAGCCAGGAGGACCCTGAGGTGCAGTTCA
ATTGGTACGTGGATGGCGTGGAGGTGCACAATGCCAAGACAAAGCCCAGAGAGGAGC
AGTTTAATTCCACATACAGGGTGGTGTCCGTGCTGACCGTGCTGCACCAGGATTGGCT
GAACGGCAAGGAGTACAAGTGTAAGGTGAGCAACAAGGGCCTGCCTTCCTCCATCGA
GAAGACAATCAGCAAGGCCAAGGGCCAGCCTAGGGAGCCCCAGGTGTACACACTGCC
TCCCAGCCAGGAGGAGATGACCAAGAACCAGGTGAGCCTGACCTGCCTGGTGAAGGG
CTTCTACCCTAGCGACATCGCCGTGGAGTGGGAGTCCAACGGCCAGCCCGAGAATAAC
TACAAGACAACACCCCCCGTGCTGGATTCCGATGGCAGCTTCTTTCTGTACTCCAGGCT
GACCGTGGATAAGAGCAGGTGGCAGGAGGGCAATGTGTTCAGCTGCTCCGTGATGCAC
GAGGCCCTGCACAATCACTACACCCAGAAGAGCCTGTCCCTGAGCCTGGGCAAGTGA -continued

| Description/Sequence/SEQ ID NO. |
|---|

(SEQ ID NO: 92)

Light chain constant region
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO: 79)
CGTACGGTGGCGGCGCCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAGC
AGGACAGCAAGGACAGCACCTACAGCCTCAGCAGCACCCTGACGCTGAGCAAAGCAG
ACTACGAGAAACACAAAGTCTACGCCTGCGAAGTCACCCATCAGGGCCTGAGCTCGCC
CGTCACAAAGAGCTTCAACAGGGGAGAGTGTTGA (SEQ ID NO: 93)

15

Having thus described in detail preferred embodiments of the present invention, it is to be understood that the invention defined by the above paragraphs is not to be limited by particular details set forth in the above description as many apparent variations thereof are possible without departing from the spirit or scope of the present invention.

We claim:

1. An isolated monoclonal antibody or an antigen-binding portion thereof, capable of binding to cytotoxic T-lymphocyte-associated antigen 4 (CTLA4), comprising i) a heavy chain variable region comprising a VH CDR1 region, a VH CDR2 region, and a VH CDR3 region, and ii) a light chain variable region comprising a VL CDR1 region, a VL CDR2 region and a VL CDR3 region, wherein the VH CDR1 region, the VH CDR2 region, the VH CDR3 region, the VL CDR1 region, the VL CDR2 region, and the VL CDR3 region comprise amino acid sequences of (1) SEQ ID NOs: 7, 8, 9, 10, 11 and 12, respectively; (2) SEQ ID NOs: 1, 2, 3, 4, 5 and 6, respectively; (3) SEQ ID NOs: 1, 2, 13, 14, 5 and 15, respectively; (4) SEQ ID NOs: 16, 17, 18, 19, 20 and 21, respectively; (5) SEQ ID NOs: 22, 23, 24, 25, 26 and 27, respectively; (6) SEQ ID NOs: 28, 29, 30, 31, 32 and 33, respectively; (7) SEQ ID NOs: 22, 34, 24, 35, 26 and 27, respectively; (8) SEQ ID NOs: 36, 37, 38, 39, 40 and 41, respectively; (9) SEQ ID NOs: 42, 43, 44, 45, 46 and 47, respectively; or (10) SEQ ID NOs: 48, 49, 50, 51, 52 and 53, respectively.

2. The isolated monoclonal antibody or the antigen-binding portion thereof of claim 1, wherein the heavy chain variable region comprises an amino acid sequence having at least 85%, 86%, 87%, 88%, 89%, 900%, 91%, 92%, 93%, 94%, 95%, %%, 97%, 98%, 99% or 100% identity to SEQ ID NOs: 58, 59, 54, 55, 62, 64, 66, 68, 70, 72, 74 or 76, wherein the $45^{th}$, $49^{th}$, and $74^{th}$ amino acid residues in the heavy chain variable region amino acid sequence having sequence identity to SEO ID NO: 59 are P, A, and D respectively; L, A, and N respectively; L, A, and D respectively; or L, S, and N respectively, and wherein the $49^{th}$ and $81^{st}$ amino acid residues in the heavy chain variable region amino acid sequence having sequence identity to SEO ID NO: 55 are A and V respectively; A and A respectively; G and V respectively; or G and A respectively.

3. The isolated monoclonal antibody or the antigen-binding portion thereof of claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 60, 61, 56, 57, 63, 65, 67, 69, 71, 73, 75 or 77, wherein the $43^{rd}$, $44^{th}$, and $87^{th}$ amino acid residues in the light chain variable region amino acid sequence having sequence identity to SEQ ID NO: 61 are T, V, and F respectively; V, P, and F respectively; V, P, and Y respectively, wherein the $43^{rd}$, $58^{th}$, $69^{th}$, and $71^{st}$ amino acid residues in the light chain variable region amino acid sequence having sequence identity to SEQ ID NO: 57 are S, M, R, and Y respectively; S, V, T, and F respectively; or V, V, T, and F respectively.

4. The isolated monoclonal antibody or the antigen-binding portion thereof of claim 1, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 58 and 60, respectively;

(2) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are P, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are T, V, and F respectively;

(3) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and N respectively, and wherein the $43^{rd}$, $44^{th}$, and $87^{th}$ amino acid residues in the heavy chain variable region and the light chain variable region amino acid sequence having sequence identity to SEQ ID NO: 61 are T, V, and F respectively;

(4) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are T, V, and F respectively;

(5) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, S, and N respectively, and wherein the $43^{rd}$, $44^{th}$, and $87^{th}$ amino acid residues in SEQ ID NO: 61 are T, V, and F respectively;

(6) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are P, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and F respectively;

(7) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and N respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and F respectively;

(8) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and F respectively;

(9) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, S, and N respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and F respectively;

(10) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are P, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and Y respectively;

(11) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and N respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and Y respectively;

(12) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, A, and D respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and Y respectively;

(13) SEQ ID NOs: 59 and 61, respectively, wherein the $45^{th}$, $49^{th}$, and $74^{th}$ amino acid residues in the heavy chain variable region and the light chain variable region amino acid sequence having sequence identity to SEQ ID NO: 59 are L, S, and N respectively, and wherein the $43^{rd}$, $44^{th}$, and $87^{th}$ amino acid residues in the heavy chain variable region and the light chain variable region amino acid sequence having sequence identity to SEQ ID NO: 61 are V, P, and Y respectively;

(14) SEQ ID NOs: 54 and 56, respectively;

(15) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, M, R, and Y respectively;

(16) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, M, R, and Y respectively;

(17) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, M, R, and Y respectively;

(18) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, M, R, and Y respectively;

(19) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, V, T, and F respectively;

(20) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, V, T, and F respectively;

(21) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, V, T, and F respectively;

(22) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are S, V, T, and F respectively;

(23) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are V, V, T, and F respectively;

(24) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are A and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are V, V, T, and F respectively;

(25) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and V respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are V, V, T, and F respectively;

(26) SEQ ID NOs: 55 and 57, respectively, wherein the $49^{th}$ and $81^{st}$ amino acid residues in the heavy chain variable region and the light chain variable region amino acid sequence having sequence identity to SEQ ID NO: 55 are G and A respectively, and wherein the $43^{rd}$, $58^{th}$, $69^{th}$, and $71^{st}$ amino acid residues in the heavy chain variable region and the light chain variable region amino acid sequence having sequence identity to SEQ ID NO: 57 are V, V, T, and F respectively;

(27) SEQ ID NOs: 62 and 63, respectively;
(28) SEQ ID NOs: 64 and 65, respectively;
(29) SEQ ID NOs: 66 and 67, respectively;
(30) SEQ ID NOs: 68 and 69, respectively;
(31) SEQ ID NOs: 70 and 71, respectively;
(32) SEQ ID NOs: 72 and 73, respectively;
(33) SEQ ID NOs: 74 and 75, respectively; or
(34) SEQ ID NOs: 76 and 77, respectively.

5. The isolated monoclonal antibody or the antigen-binding portion thereof of claim 1, comprising a heavy chain constant region having the amino acid sequence of SEQ ID NO: 78, linked to the heavy chain variable region, and a light chain constant region having the amino acid sequence of SEQ ID NO: 79, linked to the light chain variable region.

6. The isolated monoclonal antibody or the antigen-binding portion thereof of claim 1, which is able to (a) bind human CTLA4; (b) bind monkey CTLA4; (c) block CTLA4-CD80/CD86 interaction; and/or (d) promote T cell responses.

7. The isolated monoclonal antibody or the antigen-binding portion thereof of claim 1, which is mouse, chimeric or humanized.

8. The isolated monoclonal antibody or the antigen-binding portion thereof, of claim 1, which is an IgG1, IgG2 or IgG4 isotype.

9. A nucleic acid molecule encoding the isolated monoclonal antibody or the antigen-binding portion thereof of claim 1.

10. An expression vector comprising the nucleic acid molecule of claim 9.

11. A host cell comprising the nucleic acid molecule of claim 9.

12. A pharmaceutical composition comprising the isolated monoclonal antibody or antigen-binding portion thereof of claim 1, and a pharmaceutically acceptable carrier.

13. The pharmaceutical composition of claim 12, further comprising an anti-tumor agent.

14. The pharmaceutical composition of claim 12, further comprising an anti-infectious agent.

15. A method for inhibiting tumor growth in a subject in need thereof, comprising administering to the subject a therapeutically effective amount of the pharmaceutical composition of claim 12.

16. The method of claim 15, wherein the tumor is melanoma, colorectal cancer, hepatocellular carcinoma, pleural mesothelioma, lung cancer, renal cell carcinoma, cervical cancer, angiosarcoma, malignant pleural mesothelioma, metastatic transitional urothelial tract cancer, ureter cancer; urethral cancer, urinary tract cancer, head and neck cancer squamous cell carcinoma, transitional urothelial cell cancer, esophageal cancer, gastric cancer, gastroesophageal (GE) junction carcinomas, adenocarcinoma of the gastroesophageal junction, anal cancer, bile duct cancer, dysgerminoma, endometrial cancer, fallopian tube cancer, germ cell tumors, myelodysplastic syndrome, neuroblastoma, non-hodgkin lymphoma, osteosarcoma, ovarian cancer, peritoneal cancer, prostate cancer, salivary gland cancer, sarcomas, triple-negative breast cancer (TNBC), or muscle-invasive bladder cancer.

17. A method for treating or alleviating an infectious disease in a subject in need thereof, comprising administering to the subject a therapeutically effective amount of the pharmaceutical composition of claim 12.

18. The method of claim 17, wherein the infectious disease is caused by chronic HIV infection or HHV-4 infection.

19. A host cell comprising the expression vector of claim 10.

* * * * *